(12) United States Patent
Chang et al.

(10) Patent No.: US 10,577,612 B1
(45) Date of Patent: Mar. 3, 2020

(54) COMPOSITIONS AND METHODS RELATING TO GENOMIC MODIFICATIONS IN AVIAN PRIMORDIAL GERM CELLS

(71) Applicant: Alexion Pharmaceuticals, Inc., New Haven, CT (US)

(72) Inventors: Hao-Ming Chang, Arlington, MA (US); Markley C. Leavitt, Lexington, MA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 15/672,789

(22) Filed: Aug. 9, 2017

Related U.S. Application Data

(60) Provisional application No. 62/372,600, filed on Aug. 9, 2016.

(51) Int. Cl.
| | | |
|---|---|---|
| *C12N 15/66* | (2006.01) | |
| *C12N 9/22* | (2006.01) | |
| *C12N 15/85* | (2006.01) | |
| *C12N 15/67* | (2006.01) | |

(52) U.S. Cl.
CPC ............ *C12N 15/66* (2013.01); *C12N 15/67* (2013.01); *A01K 2217/05* (2013.01); *C12N 2015/8518* (2013.01)

(58) Field of Classification Search
None
See application file for complete search history.

(56) References Cited

U.S. PATENT DOCUMENTS

2019/0010515 A1* 1/2019 Oishi ................. A01K 67/027

FOREIGN PATENT DOCUMENTS

WO    WO 2017/111144    *  6/2017

OTHER PUBLICATIONS

Bai, Y. et al., Efficient Genome Editing in Chicken DF-1 Cells Using the CRISPR/Cas9 System, Genes/ Genomes/Genetics, 6: 917-923, Apr. 2016.
Dimitrov, L. et al., Germline Gene Editing in Chickens by Efficient CRISPR-Mediated Homologous Recombination in Primordial Germ Cells, PLOS One, pp. 1-10, Apr. 21, 2016.
Forsythe, R. et al., Egg White Proteins, I. Electrophoretic Studies on Whole White, Iowa Agricultural Experiment Station, Journal Paper No. J-1698: 377-383, Oct. 15, 1949.
Guerin-Dubiard, C. et al., Proteomic Analysis of Hen Egg White, Journal of Agricultural and Food Chemistry, 54: 3901-3910, 2006.
He, X. et al., Knock-in of large reporter genes in human cells via CRISPR/Cas9-induced homology-dependent and independent DNA repair, Nucleic Acids Research, 44(9): e85, pp. 1-14, 2016.
Mann, K., The chicken egg white proteome, Proteomics, 7: 3558-3568, 2007.
Mann, K. et al., In-depth analysis of the chicken egg white proteome using an LTQ Orbitrap Velos, Proteome Science, 9(7), pp. 1-6, 2011.
Oishi, I. et al., Targeted mutagenesis chicken using CRISPR/Cas9 system, Scientific Reports, pp. 1-10, Apr. 6, 2016.
Omana, D. et al., Proteomic analysis of egg white proteins during storage, Proteomics, 11: 144-153, 2011.

* cited by examiner

*Primary Examiner* — Channing S Mahatan
(74) *Attorney, Agent, or Firm* — Julie K. Staple; Dinsmore & Shohl LLP

(57) ABSTRACT

Methods of producing an exogenous protein in a bird egg are provided according to aspects of the present invention which include: providing transfected avian primordial germ cells by forming a complex of Cas protein and a guide nucleotide sequence in the avian primordial germ cells, whereby a donor DNA sequence is inserted into genomic DNA of the avian primordial germ cells under transcriptional control of a regulatory element that directs tissue-specific expression of the exogenous protein; introducing the transfected avian primordial germ cells into a population of recipient bird embryos and incubating the recipient bird embryos, generating germline chimera birds; obtaining a heterozygote and/or homozygote transgenic bird by breeding the germline chimera bird; and isolating the exogenous protein from an egg laid by a female transgenic bird.

17 Claims, 6 Drawing Sheets
Specification includes a Sequence Listing.

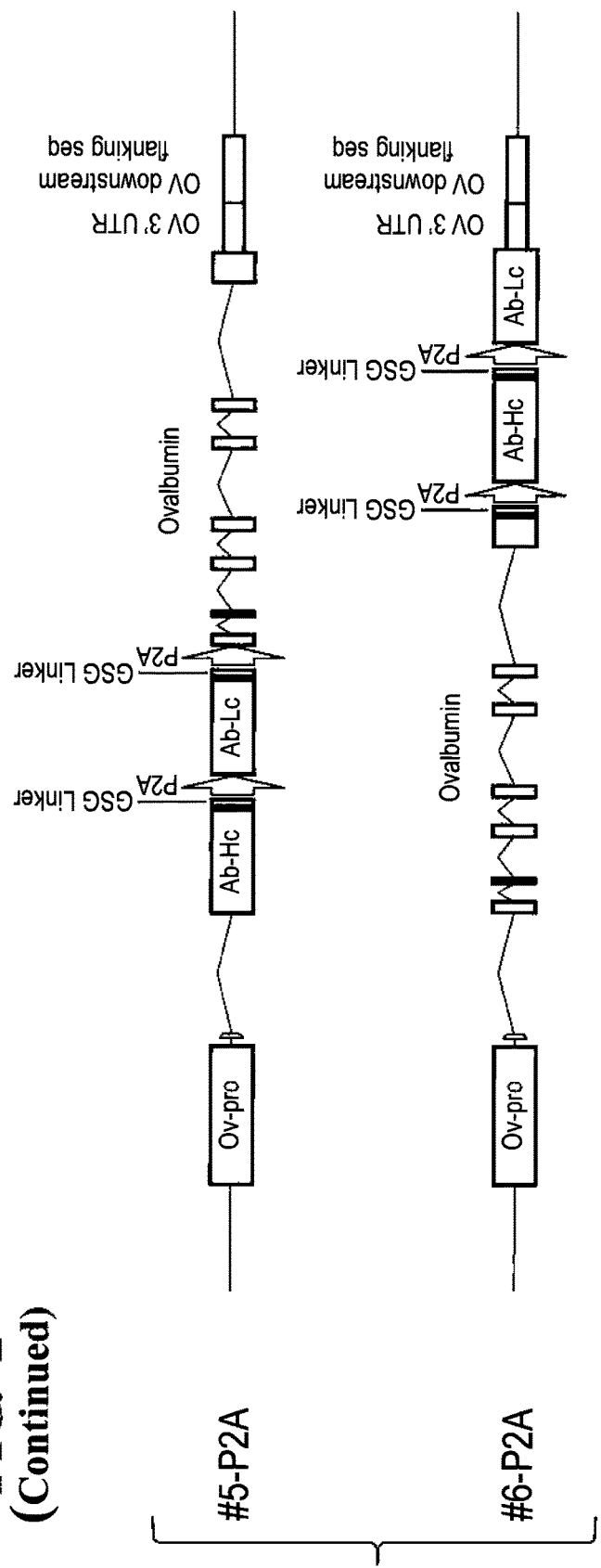
FIG. 2 (Continued)
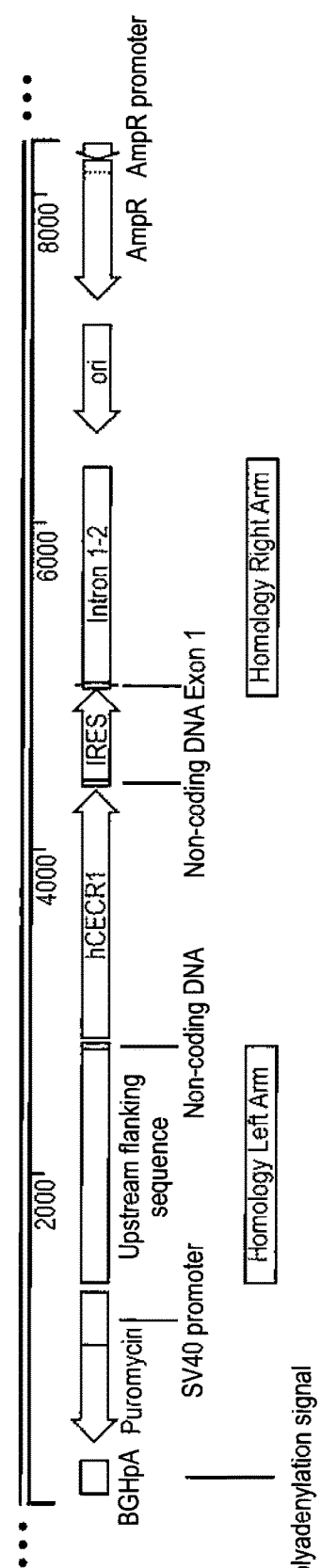
FIG. 3 OV Construct 1 hCECR1

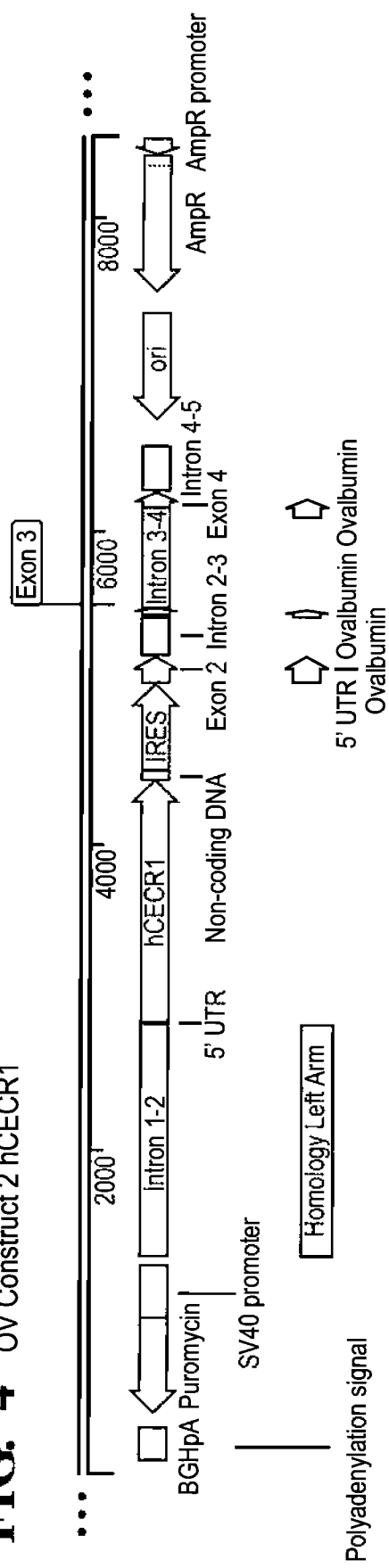
FIG. 4 OV Construct 2 hCECR1
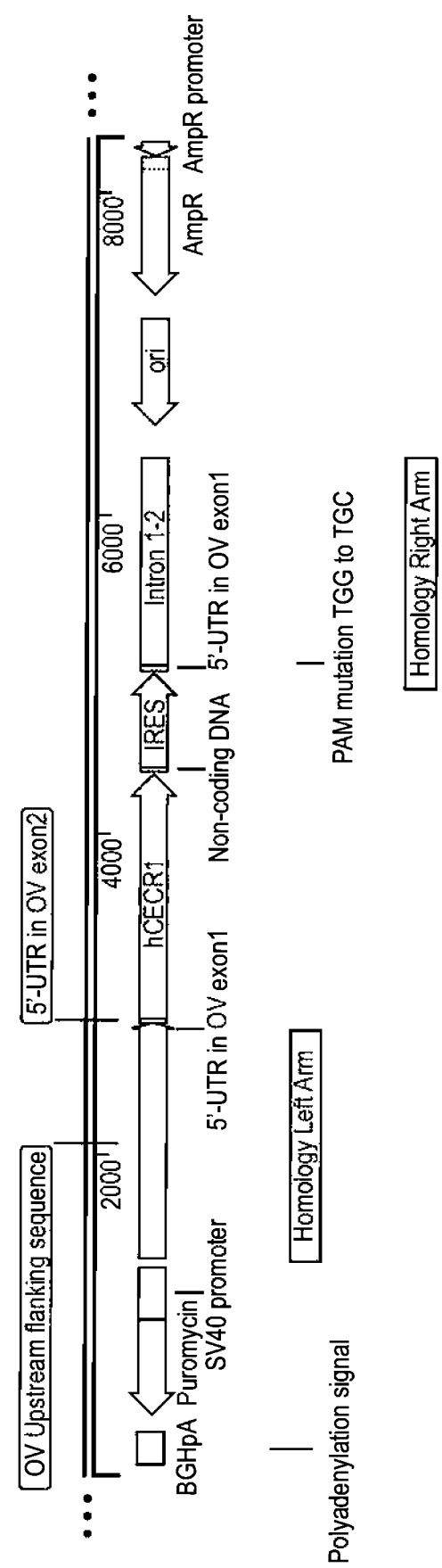
FIG. 5 OV Construct 3 hCECR1

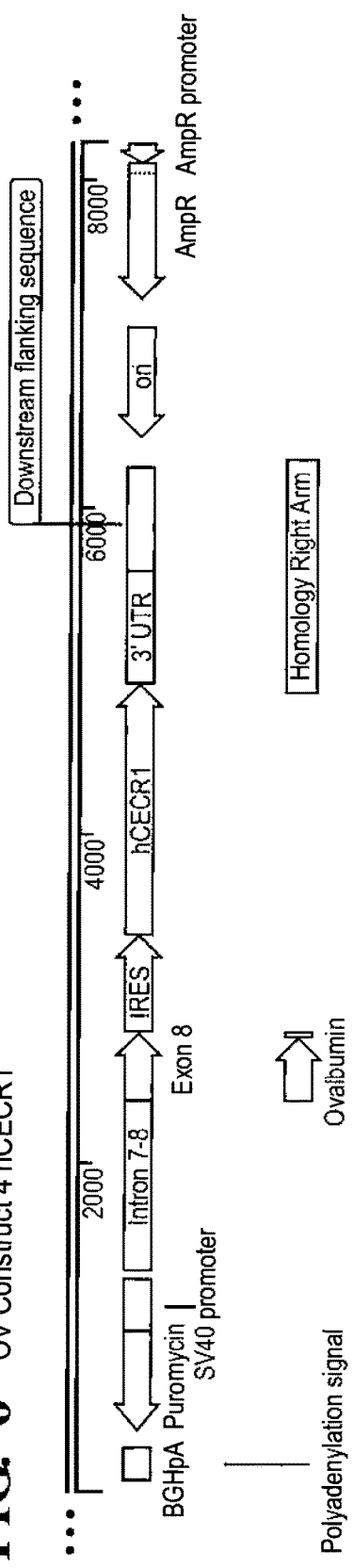
FIG. 6  OV Construct 4 hCECR1
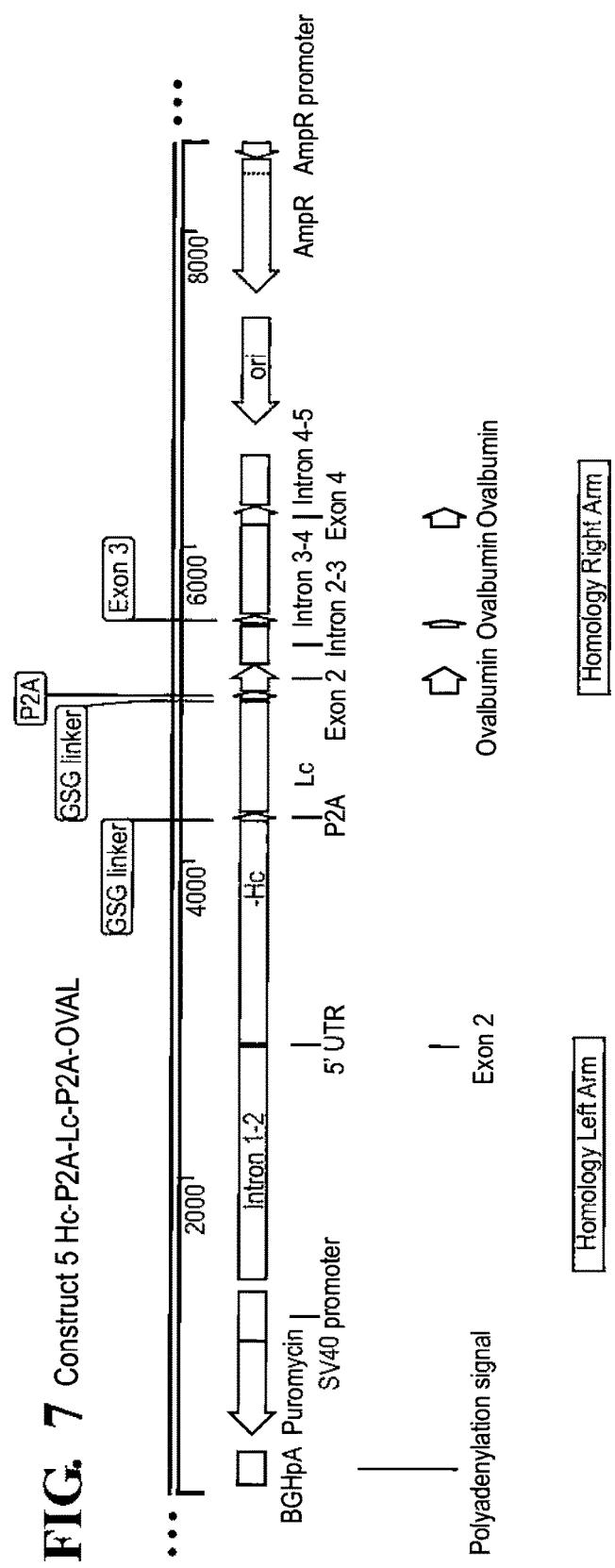
FIG. 7  Construct 5 Hc-P2A-Lc-P2A-OVAL

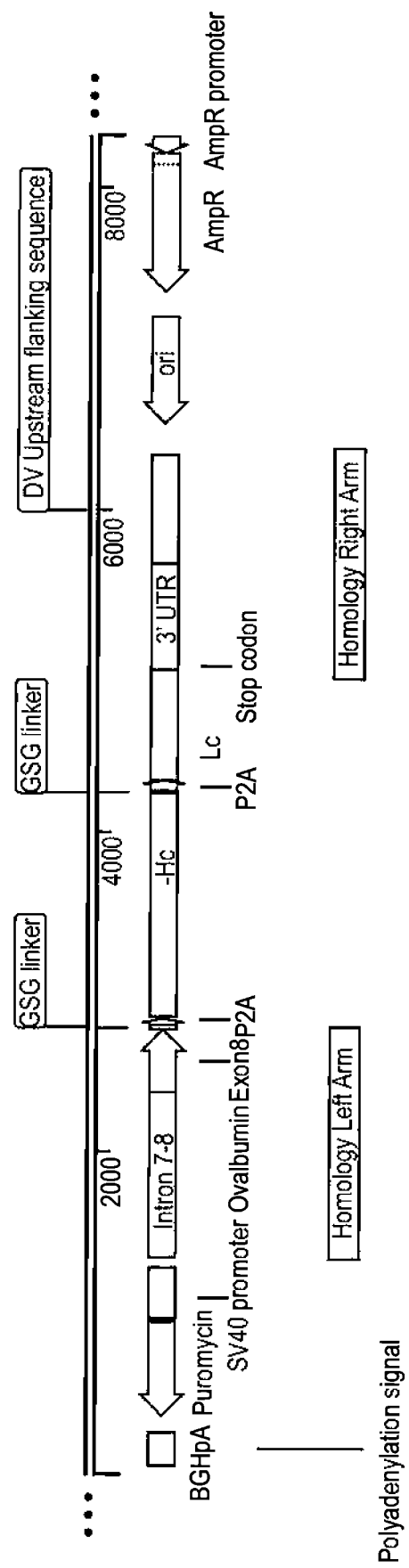
FIG. 8  Construct 6 OVAL-P2A-Hc-P2A-Lc

SEQUENCE LISTING

```
<160> NUMBER OF SEQ ID NOS: 53

<210> SEQ ID NO 1
<211> LENGTH: 18
<212> TYPE: PRT
<213> ORGANISM: Artificial Sequence
<220> FEATURE:
<223> OTHER INFORMATION: chicken lysozyme signal peptide

<400> SEQUENCE: 1

Met Arg Ser Leu Leu Ile Leu Val Leu Cys Phe Leu Pro Leu Ala Ala
1               5                   10                  15

Leu Gly

<210> SEQ ID NO 2
<211> LENGTH: 24
```

```
<212> TYPE: PRT
<213> ORGANISM: Artificial Sequence
<220> FEATURE:
<223> OTHER INFORMATION: chicken ovomucoid signal peptide

<400> SEQUENCE: 2

Met Ala Met Ala Gly Val Phe Val Leu Phe Ser Phe Val Leu Cys Gly
1               5                   10                  15

Phe Leu Pro Asp Ala Ala Phe Gly
            20

<210> SEQ ID NO 3
<211> LENGTH: 19
<212> TYPE: PRT
<213> ORGANISM: Artificial Sequence
<220> FEATURE:
<223> OTHER INFORMATION: chicken ovotransferrin signal peptide

<400> SEQUENCE: 3

Met Lys Leu Ile Leu Cys Thr Val Leu Ser Leu Gly Ile Ala Ala Val
1               5                   10                  15

Cys Phe Ala

<210> SEQ ID NO 4
<211> LENGTH: 20
<212> TYPE: DNA
<213> ORGANISM: Artificial Sequence
<220> FEATURE:
<223> OTHER INFORMATION: Sequence encoding Guide RNA

<400> SEQUENCE: 4
ctagctgtat gtacagacac                                            20

<210> SEQ ID NO 5
<211> LENGTH: 20
<212> TYPE: DNA
<213> ORGANISM: Artificial Sequence
<220> FEATURE:
<223> OTHER INFORMATION: Sequence encoding Guide RNA

<400> SEQUENCE: 5
gacaactcag agttcaccat                                            20

<210> SEQ ID NO 6
<211> LENGTH: 20
<212> TYPE: DNA
<213> ORGANISM: Artificial Sequence
<220> FEATURE:
<223> OTHER INFORMATION: Sequence encoding Guide RNA

<400> SEQUENCE: 6
tcaaaaggta agcaactctc                                            20

<210> SEQ ID NO 7
<211> LENGTH: 20
<212> TYPE: DNA
<213> ORGANISM: Artificial Sequence
<220> FEATURE:
<223> OTHER INFORMATION: Sequence encoding Guide RNA

<400> SEQUENCE: 7
gtgctctggg tcttgttgga                                            20

<210> SEQ ID NO 8
<211> LENGTH: 20
```

<212> TYPE: DNA
<213> ORGANISM: Artificial Sequence
<220> FEATURE:
<223> OTHER INFORMATION: PCR primer

<400> SEQUENCE: 8
agaacctccc tgtctggtaa                                               20

<210> SEQ ID NO 9
<211> LENGTH: 22
<212> TYPE: DNA
<213> ORGANISM: Artificial Sequence
<220> FEATURE:
<223> OTHER INFORMATION: PCR primer

<400> SEQUENCE: 9
gatagagcag agccgaagaa ag                                            22

<210> SEQ ID NO 10
<211> LENGTH: 21
<212> TYPE: DNA
<213> ORGANISM: Artificial Sequence
<220> FEATURE:
<223> OTHER INFORMATION: PCR primer

<400> SEQUENCE: 10
ccacgttgtg agttggatag t                                             21

<210> SEQ ID NO 11
<211> LENGTH: 22
<212> TYPE: DNA
<213> ORGANISM: Artificial Sequence
<220> FEATURE:
<223> OTHER INFORMATION: PCR primer

<400> SEQUENCE: 11
aagccagttg cctctacata tt                                            22

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
tctatggcgt caaaggtcaa a                                             21

<210> SEQ ID NO 13
<211> LENGTH: 20
<212> TYPE: DNA
<213> ORGANISM: Artificial Sequence
<220> FEATURE:
<223> OTHER INFORMATION: PCR primer

<400> SEQUENCE: 13
ggtagcaaac tgtcccagaa                                               20

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
ccctgtgctt cttgctgttg                                          20

<210> SEQ ID NO 15
<211> LENGTH: 23
<212> TYPE: DNA
<213> ORGANISM: Artificial Sequence
<220> FEATURE:
<223> OTHER INFORMATION: PCR primer

<400> SEQUENCE: 15
gcccgtgttt catctatgga tag                                      23

<210> SEQ ID NO 16
<211> LENGTH: 25
<212> TYPE: DNA
<213> ORGANISM: Artificial Sequence
<220> FEATURE:
<223> OTHER INFORMATION: probe directed against hCECR1

<400> SEQUENCE: 16
tggcaatgtc tttcttcggc tctgc                                    25

<210> SEQ ID NO 17
<211> LENGTH: 22
<212> TYPE: DNA
<213> ORGANISM: Artificial Sequence
<220> FEATURE:
<223> OTHER INFORMATION: PCR primer

<400> SEQUENCE: 17
gtggattctg ctggaggatt at                                       22

<210> SEQ ID NO 18
<211> LENGTH: 22
<212> TYPE: DNA
<213> ORGANISM: Artificial Sequence
<220> FEATURE:
<223> OTHER INFORMATION: PCR primer

<400> SEQUENCE: 18
gatgagacca gagatggtga ag                                       22

<210> SEQ ID NO 19
<211> LENGTH: 20
<212> TYPE: DNA
<213> ORGANISM: Artificial Sequence
<220> FEATURE:
<223> OTHER INFORMATION: PCR primer

<400> SEQUENCE: 19
cctggtctcg gaaacataag                                          20

<210> SEQ ID NO 20
<211> LENGTH: 20
<212> TYPE: DNA
<213> ORGANISM: Artificial Sequence
<220> FEATURE:
<223> OTHER INFORMATION: PCR primer

<400> SEQUENCE: 20
agtggtgcct tgagaatgac                                          20

<210> SEQ ID NO 21
<211> LENGTH: 21
<212> TYPE: DNA
<213> ORGANISM: Artificial Sequence

```
<220> FEATURE:
<223> OTHER INFORMATION: PCR primer

<400> SEQUENCE: 21
gaatggatgg tcagccctaa a                                              21

<210> SEQ ID NO 22
<211> LENGTH: 23
<212> TYPE: DNA
<213> ORGANISM: Artificial Sequence
<220> FEATURE:
<223> OTHER INFORMATION: PCR primer

<400> SEQUENCE: 22
ccatctctgg tctcatccat tac                                            23

<210> SEQ ID NO 23
<211> LENGTH: 22
<212> TYPE: DNA
<213> ORGANISM: Artificial Sequence
<220> FEATURE:
<223> OTHER INFORMATION: PCR primer

<400> SEQUENCE: 23
gcacattcac aagacccatt ac                                             22

<210> SEQ ID NO 24
<211> LENGTH: 204
<212> TYPE: DNA
<213> ORGANISM: Artificial Sequence
<220> FEATURE:
<223> OTHER INFORMATION: Bovine Growth Hormone Polyadenylation Signal
      (BGHpA)

<400> SEQUENCE: 24
catgcctgct attgtcttcc caatcctccc ccttgctgtc ctgccccacc ccacccccca    60
gaatagaatg acacctactc agacaatgcg atgcaatttc ctcattttat taggaaagga   120
cagtgggagt ggcaccttcc agggtcaagg aaggcacggg ggaggggcaa acaacagatg   180
gctggcaact agaaggcaca gtcg                                          204

<210> SEQ ID NO 25
<211> LENGTH: 600
<212> TYPE: DNA
<213> ORGANISM: Artificial Sequence
<220> FEATURE:
<223> OTHER INFORMATION: Puromycin Resistance sequence

<400> SEQUENCE: 25
tcaggcaccg ggcttgcggg tcatgcacca ggtgcgcggt ccttcgggca cctcgacgtc    60
ggcggtgacg gtgaagccga ccgctcgta gaaggggagg ttgcggggcg cggaggtctc   120
caggaaggcg gcaccccgg cgcgctcggc cgcctccact ccggggagca cgacggcgct   180
gcccagaccc ttgccctggt ggtcgggcga cgccgacg tggccagga accacgcggg    240 ctccttgggc cggtgcggcg ccaggaggcc ttccatctgt tgctgcgcgg ccagccggga   300
accgctcaac tcggccatgc gcgggccgat tcggcgaac accgccccg cttcgacgct    360 ctccggcgtg gtccagaccg ccaccgcggc gccgtcgtcc gcgacccaca ccttgccgat   420
gtcgagcccg acgcgcgtga ggaagagttc ttgcagctcg gtgacccgct cgatgtggcg   480
gtccgggtcg acggtgtggc gcgtggcggg gtagtcggcg aacgcggcgg cgagggtgcg   540
tacggcccgg gggacgtcgt cgcgggtggc gaggcgcacc gtgggcttgt actcggtcat   600
```

<210> SEQ ID NO 26
<211> LENGTH: 317
<212> TYPE: DNA
<213> ORGANISM: Artificial Sequence
<220> FEATURE:
<223> OTHER INFORMATION: SV40 promoter

<400> SEQUENCE: 26

```
tttgcaaaag cctaggcctc caaaaaagcc tcctcactac ttctggaata gctcagaggc      60
agaggcggcc tcggcctctg cataaataaa aaaaattagt cagccatggg gcggagaatg    120
ggcggaactg ggcggagtta ggggcgggat gggcggagtt aggggcggga ctatggttgc    180
tgactaattg agatgcatgc tttgcatact tctgcctgct ggggagcctg ggactttcc     240
acacctggtt gctgactaat tgagatgcat gctttgcata cttctgcctg ctggggagcc    300
tggggacttt ccacacc                                                    317
```

<210> SEQ ID NO 27
<211> LENGTH: 1292
<212> TYPE: DNA
<213> ORGANISM: Artificial Sequence
<220> FEATURE:
<223> OTHER INFORMATION: Chicken ovalbumin gene - Intron 1-2

<400> SEQUENCE: 27

```
gtaagcaact ctctggaatt accttctctc tatattagct cttacttgca cctaaacttt      60
aaaaaattaa caattattgt gttatgtgtt gtatctttaa gggtgaagta cctgcgtgat    120
acccccctata aaaacttctc acctgtgtat gcattctgca ctattttatt atgtgtaaaa   180
gctttgtgtt tgttttcagg aggcttattc tttgtgctta aaatatgttt ttaatttcag    240
aacatcttat cctgtcgttc actatctgat atgctttgca gtttgcttga ttaacttcta    300
gccctacaga gtgcacagag agcaaaatca tggtgttcag tgaattctgg ggagttattt    360
taatgtgaaa attctctaga agtttaattc ctgcaaagtg cagctgctga tcactacaca    420
agataaaaat gtgggggggtg cataaacgta tattcttaca ataatagata catgtgaact    480
tgtatacaga aaagaaaatg agaaaaatgt gtgtgcgtat actcacacac gtggtcagta    540
aaaacttttg aggggtttaa tacagaaaat ccaatcctga ggccccagca ctcagtacgc    600
atataaaggg ctgggctctg aaggacttct gactttcaca gattatataa atctcaggaa    660
agcaactaga ttcatgctgg ctccaaaagc tgtgctttat ataagcacac tggctataca    720
atagttgtac agttcagctc tttataatag aaacagacag aacaagtata atcttctat     780
tggtctatgt catgaacaag aattcattca gtggctctgt tttatagtaa acattgctat    840
tttatcatgt ctgcatttct cttctgtctg aatgtcacca ctaaaattta actccacaga    900
aagtttatac tacagtacac atgcatatct ttgagcaaag caaaccatac ctgaaagtgc    960
aatagagcag aatatgaatt acatgcgtgt ctttctccta gactcatga ccccatataa    1020
attacattcc ttatctattc tgccatcacc aaaacaaagg taaaaatact tttgaagatc   1080
tactcatagc aagtagtgtg caacaaacag atatttctct acatttattt ttagggaata   1140
aaaataagaa ataaaatagt cagcaagcct ctgcttctc atatatctgt ccaaacctaa    1200
agtttactga aatttgctct ttgaatttcc agttttgcaa gcctatcaga ttgtgtttta   1260
atcagaggta ctgaaaagta tcaatgaatt ct                                 1292
```

<210> SEQ ID NO 28

<211> LENGTH: 1483
<212> TYPE: DNA
<213> ORGANISM: Artificial Sequence
<220> FEATURE:
<223> OTHER INFORMATION: Chicken ovalbumin gene Intron 1-2, alternate sequence

<400> SEQUENCE: 28

```
agtacctgcg tgataccccc tataaaaact tctcacctgt gtatgcattc tgcactattt      60
tattatgtgt aaaagctttg tgtttgtttt caggaggctt attctttgtg cttaaaatat     120
gtttttaatt tcagaacatc ttatcctgtc gttcactatc tgatatgctt tgcagtttgc     180
ttgattaact tctagcccta cagagtgcac agagagcaaa atcatggtgt tcagtgaatt     240
ctggggagtt attttaatgt gaaaattctc tagaagttta attcctgcaa agtgcagctg     300
ctgatcacta cacaagataa aaatgtgggg ggtgcataaa cgtatattct tacaataata     360
gatacatgtg aacttgtata cagaaaagaa aatgagaaaa atgtgtgtgc gtatactcac     420
acacgtggtc agtaaaaact tttgaggggt ttaatacaga aaatccaatc ctgaggcccc     480
agcactcagt acgcatataa agggctgggc tctgaaggac ttctgacttt cacagattat     540
ataaatctca ggaaagcaac tagattcatg ctggctccaa aagctgtgct ttatataagc     600
acactggcta tacaatagtt gtacagttca gctctttata atagaaacag acagaacaag     660
tataaatctt ctattggtct atgtcatgaa caagaattca ttcagtggct ctgtttata      720
gtaaacattg ctattttatc atgtctgcat ttctcttctg tctgaatgtc accactaaaa     780
tttaactcca cagaaagttt atactacagt acacatgcat atctttgagc aaagcaaacc     840
atacctgaaa gtgcaataga gcagaatatg aattacatgc gtgtctttct cctagactac     900
atgaccccat ataaattaca ttccttatct attctgccat caccaaaaca aaggtaaaaa     960
tacttttgaa gatctactca tagcaagtag tgtgcaacaa acagatattt ctctacattt    1020
attttaggg aataaaaata agaaataaaa tagtcagcaa gcctctgctt tctcatatat    1080
ctgtccaaac ctaaagttta ctgaaatttg ctctttgaat ttccagtttt gcaagcctat    1140
cagattgtgt tttaatcaga ggtactgaaa agtatcaatg aattctagct ttcactgaac    1200
aaaaatatgt agaggcaact ggcttctggg acagtttgct acccaaaaga caactgaatg    1260
caaatacata aatagattta tgaatatggt tttgaacatg cacatgagag gtggatatag    1320
caacagacac attaccacag aattacttta aaactacttg ttaacattta attgcctaaa    1380
aactgctcgt aatttactgt tgtagcctac catagagtac cctgcatggt actatgtaca    1440
gcattccatc cttacatttt cactgttctg ctgtttgctc tag                      1483
```

<210> SEQ ID NO 29
<211> LENGTH: 1292
<212> TYPE: DNA
<213> ORGANISM: Artificial Sequence
<220> FEATURE:
<223> OTHER INFORMATION: Chicken ovalbumin gene Intron 1-2, alternate sequence

<400> SEQUENCE: 29

```
gtaagcaact ctctgcaatt accttctctc tatattagct cttacttgca cctaaacttt      60
aaaaaattaa caattattgt gttatgtgtt gtatctttaa gggtgaagta cctgcgtgat     120
accccctata aaacttctc acctgtgtat gcattctgca ctattttatt atgtgtaaaa     180
gctttgtgtt tgttttcagg aggcttattc tttgtgctta aaatatgttt ttaatttcag     240
aacatcttat cctgtcgttc actatctgat atgctttgca gtttgcttga ttaacttcta     300
```

```
gccctacaga gtgcacagag agcaaaatca tggtgttcag tgaattctgg ggagttattt      360
taatgtgaaa attctctaga agtttaattc ctgcaaagtg cagctgctga tcactacaca      420
agataaaaat gtggggggtg cataaacgta tattcttaca ataatagata catgtgaact      480
tgtatacaga aaagaaaatg agaaaaatgt gtgtgcgtat actcacacac gtggtcagta      540 aaaactttg aggggtttaa tacagaaaat ccaatcctga ggccccagca ctcagtacgc       600
atataaaggg ctgggctctg aaggacttct gactttcaca gattatataa atctcaggaa      660
agcaactaga ttcatgctgg ctccaaaagc tgtgctttat ataagcacac tggctataca      720
atagttgtac agttcagctc tttataatag aaacagacag aacaagtata aatcttctat      780
tggtctatgt catgaacaag aattcattca gtggctctgt tttatagtaa acattgctat      840
tttatcatgt ctgcatttct cttctgtctg aatgtcacca ctaaaattta actccacaga     900
aagtttatac tacagtacac atgcatatct ttgagcaaag caaaccatac ctgaaagtgc      960
aatagagcag aatatgaatt acatgcgtgt ctttctccta gactacatga ccccatataa     1020
attacattcc ttatctattc tgccatcacc aaaacaaagg taaaaatact tttgaagatc     1080
tactcatagc aagtagtgtg caacaaacag atatttctct acatttattt ttagggaata     1140
aaaataagaa ataaaatagt cagcaagcct ctgctttctc atatatctgt ccaaacctaa     1200
agtttactga aatttgctct ttgaatttcc agttttgcaa gcctatcaga ttgtgtttta     1260
atcagaggta ctgaaaagta tcaatgaatt ct                                   1292

<210> SEQ ID NO 30
<211> LENGTH: 1433
<212> TYPE: DNA
<213> ORGANISM: Artificial Sequence
<220> FEATURE:
<223> OTHER INFORMATION: Chicken ovalbumin gene OV upstream flanking
      sequence (containing OVAL promoter)

<400> SEQUENCE: 30
gatatctata cacaaattat tagtgtttga ttgacaccag atgacagaga agtgcatctg       60
agaaaaccta ttcccaatct cctttctctt tctgcagact gacatgcatt tcataggtag      120
agataacatt tactgggaag cacatctatc atcacaaaaa gcaggcaaga ttttcagact      180
ttcttagtgg ctgaaataga agcaaaagac gtgattaaaa acaaaatgaa acaaaaaaaa      240
tcagttgata cctgtggtgt agacatccag caaaaaaata ttatttgcac taccatcttg      300
tcttaagtcc tcagacttgg caaggagaat gtagatttcc acagtatata tgttttcaca      360
aaaggaagga gagaaacaaa agaaaatggc actgactaaa cttcagctag tggtatagga      420
aagtaattct gcttaacaga gattgcagtg atctctatgt atgtcctgaa gaattatgtt      480 gtacttttttt ccccatttt taaatcaaac agtgctttac agaggtcaga atggtttctt      540
tactgtttgt caattctatt atttcaatac agaacaatag cttctataac tgaaatatat      600
ttgctattgt atattatgat tgtccctcga accatgaaca ctcctccagc tgaatttcac      660
aattcctctg tcatctgcca ggccattaag ttattcatgg aagatctttg aggaacactg      720
caagttcata tcataaacac atttgaaatt gagtattgtt ttgcattgta tggagctatg      780
ttttgctgta tcctcagaaa aaagtttgt tataaagcat tcacacccat aaaaagatag      840
atttaaatat tccaactata ggaagagaag tgcgtctgct cttcactcta gtctcagttg      900
gctccttcac atgcacgctt ctttatttct cctatttgt caagaaaata ataggtcacg      960
tcttgttctc acttatgtcc tgcctagcat ggctcagatg cacgttgtac atacaagaag     1020
```

| gatcaaatga aacagacttc tggtctgtta ctacaaccat agtaataagc acactaacta | 1080 |
| ataattgcta attatgtttt ccatctccaa ggttcccaca ttttctgtt ttcttaaaga | 1140 |
| tcccattatc tggttgtaac tgaagctcaa tggaacatga gcaatatttc ccagtcttct | 1200 |
| ctcccatcca acagtcctga tggattagca gaacaggcag aaaacacatt gttacccaga | 1260 |
| attaaaaact aatatttgct ctccattcaa tccaaaatgg acctattgaa actaaaatct | 1320 |
| aacccaatcc cattaaatga tttctatggc gtcaaaggtc aaacttctga agggaacctg | 1380 |
| tgggtgggtc acaattcagg ctatatattc cccagggctc agccagtgtc tgt | 1433 |

```
<210> SEQ ID NO 31
<211> LENGTH: 1536
<212> TYPE: DNA
<213> ORGANISM: Homo sapiens

<400> SEQUENCE: 31
```

| atgttggtgg atggcccatc tgagcggcca gccctgtgct tcttgctgtt ggctgtggca | 60 |
| atgtctttct tcggctctgc tctatccata gatgaaacac gggcgcatct gttgttgaaa | 120 |
| gaaaagatga tgcggctggg ggggcggctg gtgctgaaca ccaaggagga gctggccaat | 180 |
| gagaggctca tgacgctcaa atcgctgag atgaaggagg ccatgaggac cctgatattc | 240 |
| ccacccagca tgcactttt ccaggccaag catctcattg agagaagtca agtgtttaat | 300 |
| attctaagga tgatgccaaa aggggctgcc ttgcacctcc atgacattgg catcgtgact | 360 |
| atggactggc tggtgaggaa tgtcacctac aggcctcact gccacatctg tttcacccca | 420 |
| agggggatca tgcagttcag atttgctcac ccaactcccc gtccatcaga aaaatgttcc | 480 |
| aagtggattc tgctgaggaa ttatcggaag cgggtgcaga acgtcactga gtttgatgac | 540 |
| agcttgctga ggaatttcac tctggtgacc cagcacccgg aggtgattta cacaaaccaa | 600 |
| aatgttgtct ggtcgaaatt tgaaaccatc ttcttcacca tctctggtct catccattac | 660 |
| gctccagtgt tcagagacta tgtcttccgg agcatgcagg agttctacga ggacaacgtg | 720 |
| ctctacatgg agatcagagc caggctgctg ccggtgtatg agctcagtgg agagcaccat | 780 |
| gacgaagagt ggtcagtgaa gacttatcag gaagtagctc agaagtttgt ggaaactcat | 840 |
| cctgagttta ttggaatcaa aatcattat tcggatcaca gatccaaaga tgtggctgtc | 900 |
| atcgcagaat ccatccgaat ggccatgggg ctccgaatca agttccccac ggtggtggca | 960 |
| gggtttgacc tggtggggca tgaggacact ggccactcct tgcatgacta caaggaagct | 1020 |
| ctgatgatcc ccgccaagga tggcgttaag ctgccttact tcttccacgc cggagaaaca | 1080 |
| gactggcagg gtacttccat agacaggaac attctggatg ctctgatgct gaacactacc | 1140 |
| agaatcggcc atggatttgc tttgagcaaa caccccgcag tcaggactta ttcctggaaa | 1200 |
| aaggacatcc ccatagaagt ctgtcccatc tctaaccagg tgctgaaact ggtgtctgac | 1260 |
| ttgaggaacc accctgtagc cactctgatg gccactgggc accccatggt gatcagctct | 1320 |
| gatgacccag ctatgtttgg tgccaaaggc ttgtcctatg atttctatga ggtcttcatg | 1380 |
| ggcattgggg ggatgaaggc tgatctgagg accctcaaac agctggccat gaactctatc | 1440 |
| aagtacagta ccctgttgga gagtgagaaa atactttca tggaaatatg gaagaagaga | 1500 |
| tgggataagt tcatagcaga tgtggctaca aagtga | 1536 |

```
<210> SEQ ID NO 32
<211> LENGTH: 588
<212> TYPE: DNA
```

<213> ORGANISM: Artificial Sequence
<220> FEATURE:
<223> OTHER INFORMATION: internal ribosome entry site (IRES)

<400> SEQUENCE: 32

```
gccgccctc tccctcccccc cccctaacg ttactggccg aagccgcttg gaataaggcc      60
ggtgtgcgtt tgtctatatg ttattttcca ccatattgcc gtcttttggc aatgtgaggg    120
cccggaaacc tggccctgtc ttcttgacga gcattcctag gggtcttttcc cctctcgcca   180
aaggaatgca aggtctgttg aatgtcgtga aggaagcagt tcctctggaa gcttcttgaa    240
gacaaacaac gtctgtagcg acccttttgca ggcagcggaa ccccccacct ggcgacaggt   300
gcctctgcgg ccaaaagcca cgtgtataag atacacctgc aaaggcggca caaccccagt   360
gccacgttgt gagttggata gttgtggaaa gagtcaaatg gctctcctca agcgtattca    420
acaaggggct gaaggatgcc cagaaggtac cccattgtat gggatctgat ctggggcctc   480
ggtacacatg ctttacatgt gtttagtcga ggttaaaaaa acgtctaggc cccccgaacc   540
acggggacgt ggttttcctt tgaaaaacac gatgataata tggccaca                588
```

<210> SEQ ID NO 33
<211> LENGTH: 47
<212> TYPE: DNA
<213> ORGANISM: Artificial Sequence
<220> FEATURE:
<223> OTHER INFORMATION: 5'-UTR from Chicken Ovalbumin gene Exon 1

<400> SEQUENCE: 33

```
acatacagct agaaagctgt attgccttta gcactcaagc tcaaaag                   47
```

<210> SEQ ID NO 34
<211> LENGTH: 17
<212> TYPE: DNA
<213> ORGANISM: Artificial Sequence
<220> FEATURE:
<223> OTHER INFORMATION: 5'-UTR from Chicken Ovalbumin gene Exon 2

<400> SEQUENCE: 34

```
acaactcaga gttcacc                                                   17
```

<210> SEQ ID NO 35
<211> LENGTH: 677
<212> TYPE: DNA
<213> ORGANISM: Artificial Sequence
<220> FEATURE:
<223> OTHER INFORMATION: ori (origin of replication)

<400> SEQUENCE: 35

```
atgtgagcaa aaggccagca aaaggccagg aaccgtaaaa aggccgcgtt gctggcgttt     60
ttccataggc tccgcccccc tgacgagcat cacaaaaatc gatgctcaag tcagaggtgg    120
cgaaacccga caggactata aagataccag gcgtttcccc ctggaagctc cctcgtgcgc    180
tctcctgttc cgaccctgcc gcttaccgga tacctgtccg cctttctccc ttcgggaagc    240
gtggcgcttt ctcatagctc acgctgtagg tatctcagtt cggtgtaggt cgttcgctcc    300
aagctgggct gtgtgcacga accccccgtt cagcccgacc gctgcgcctt atccggtaac   360
tatcgtcttg agtccaaccc ggtaagacac gacttatcgc cactggcagc agccactggt    420
aacaggatta gcagagcgag gtatgtaggc ggtgctacag agttcttgaa gtggtggcct    480
aactacggct acactagaag aacagtattt ggtatctgcg ctctgctgaa gccagttacc    540
ttcggaaaaa gagttggtag ctcttgatcc ggcaaacaaa ccaccgctgg tagcggtggt    600
```

```
tttttgttt gcaagcagca gattacgcgc agaaaaaaag gatctcaaga agatcctttg    660
atcttttcta cggggtc                                                 677

<210> SEQ ID NO 36
<211> LENGTH: 861
<212> TYPE: DNA
<213> ORGANISM: Artificial Sequence
<220> FEATURE:
<223> OTHER INFORMATION: Ampicillin resistance sequence (AmpR)

<400> SEQUENCE: 36
ttaccaatgc ttaatcagtg aggcacctat ctcagcgatc tgtctatttc gttcatccat    60
agttgcctga ctccccgtcg tgtagataac tacgatacgg gagggcttac catctggccc   120
cagtgctgca atgataccgc gagacccacg ctcaccggct ccagatttat cagcaataaa   180
ccagccagcc ggaagggccg agcgcagaag tggtcctgca actttatccg cctccatcca   240
gtctattaat tgttgccggg aagctagagt aagtagttcg ccagttaata gtttgcgcaa   300
cgttgttgcc attgctacag gcatcgtggt gtcacgctcg tcgtttggta tggcttcatt   360
cagctccggt tcccaacgat caaggcgagt tacatgatcc cccatgttgt gcaaaaaagc   420
ggttagctcc ttcggtcctc cgatcgttgt cagaagtaag ttggccgcag tgttatcact   480
catggttatg gcagcactgc ataattctct tactgtcatg ccatccgtaa gatgcttttc   540
tgtgactggt gagtactcaa ccaagtcatt ctgagaatag tgtatgcggc gaccgagttg   600
ctcttgcccg gcgtcaatac gggataatac cgcgccacat agcagaactt taaaagtgct   660
catcattgga aaacgttctt cggggcgaaa actctcaagg atcttaccgc tgttgagatc   720
cagttcgatg taacccactc gtgcacccaa ctgatcttca gcatctttta ctttcaccag   780
cgtttctggg tgagcaaaaa caggaaggca aaatgccgca aaaaagggaa taagggcgac   840
acggaaatgt tgaatactca t                                            861

<210> SEQ ID NO 37
<211> LENGTH: 105
<212> TYPE: DNA
<213> ORGANISM: Artificial Sequence
<220> FEATURE:
<223> OTHER INFORMATION: Promoter for AmpR

<400> SEQUENCE: 37
actcttcctt tttcaatatt attgaagcat ttatcagggt tattgtctca tgagcggata    60
catatttgaa tgtatttaga aaataaaca ataggggtt ccgcg                    105

<210> SEQ ID NO 38
<211> LENGTH: 1035
<212> TYPE: DNA
<213> ORGANISM: Artificial Sequence
<220> FEATURE:
<223> OTHER INFORMATION: Chicken ovalbumin gene Intron 7-8

<400> SEQUENCE: 38
tgtaataaat gagaattcat tgaaatgtta gtatgctaac tcaatctaaa ttataaagat    60
aaagaggcat taatcacag ctagatttcc atcacttgtg acagacaggc atatgaatga   120
ttatgtacag ctctaggaaa aaaagtatgt aggaaaacta gtacattttg attagaaagt   180
ctgaaaatga ggtgccttga tccaagagaa tacgtgtgtt tgagaaaaaa aaagtttgga   240
tagaggtggt aagagagaat atattgaaat ggtgtttcta caaactgcca tggccagatt   300
```

| | |
|---|---|
| tgtgtaagag acattcagta agtaggcaag gaaagaaata ttactaggta caaagcaaca | 360 |
| ttagtaatac caaaagaaac caattattcc agatgccaat ctcgtaatag ggttaagaga | 420 |
| tttccacccc tctagtggtc accagtgcaa ccagtaactt tgctaattta cattttcttt | 480 |
| ttttaaatgg cagatatagc tttgaactga gtgatcatga actggtactg tgtaaataag | 540 |
| atggaagcat acttggcagc taaacttcta gttttttaaaa actcaaattc tcttgaaaga | 600 |
| tcagttccca gtctagtaac agctgatagt ttaagtatca gtaattggct accattaaca | 660 |
| actggctcct gagaggtctt aaatgtagag acagctttaa actcaaaagc acagagtgat | 720 |
| ttttagaata gacttcccaa gcaaagaaaa taaacaggga ggagctttaa gggagtagcc | 780 |
| atctcattat tattattatt taaagaaatg gcagcaagcc tacaaaagaa aaataagaca | 840 |
| gagcagagaa gaaagagtca tggtatgctt ttctatctta gcaaaattaa tctctacatg | 900 |
| cctaggaaaa agccatgaca agagcaatca gttcaaaagg tgtatgcaaa aaaccacata | 960 |
| atagtaacta gtactgcatt gccaggaagg aagttatgtc gccattccat ggatctcatt | 1020 |
| ctcatttcct tgcag | 1035 |

<210> SEQ ID NO 39
<211> LENGTH: 1031
<212> TYPE: DNA
<213> ORGANISM: Artificial Sequence
<220> FEATURE:
<223> OTHER INFORMATION: Chicken ovalbumin gene alternate sequence Intron 7-8

<400> SEQUENCE: 39

| | |
|---|---|
| ataaatgaga attcattgaa atgttagtat gctaactcaa tctaaattat aaagataaag | 60 |
| aggcatttaa tcacagctag atttccatca cttgtgacag acaggcatat gaatgattat | 120 |
| gtacagctct aggaaaaaaa gtatgtagga aaactagtac attttgatta gaaagtctga | 180 |
| aaatgaggtg ccttgatcca agagaatacg tgtgtttgag aaaaaaaaag tttggataga | 240 |
| ggtggtaaga gagaatatat tgaaatggtg tttctacaaa ctgccatggc cagatttgtg | 300 |
| taagagacat tcagtaagta ggcaaggaaa gaaatattac taggtacaaa gcaacattag | 360 |
| taataccaaa agaaaccaat tattccagat gccaatctcg taatagggtt aagagatttc | 420 |
| caccccctcta gtggtcacca gtgcaaccag taactttgct aatttacatt ttcttttttt | 480 |
| aaatggcaga tatagctttg aactgagtga tcatgaactg gtactgtgta ataagatgg | 540 |
| aagcatactt ggcagctaaa cttctagttt ttaaaaactc aaattctctt gaaagatcag | 600 |
| ttcccagtct agtaacagct gatagttaa gtatcagtaa ttggctacca ttaacaactg | 660 |
| gctcctgaga ggtcttaaat gtagagacag ctttaaactc aaaagcacag agtgattttt | 720 |
| agaatagact tcccaagcaa agaaaataaa cagggaggag ctttaaggga gtagccatct | 780 |
| cattattatt attatttaaa gaaatggcag caagcctaca aagaaaaat aagacagagc | 840 |
| agagaagaaa gagtcatggt atgcttttct atcttagcaa aattaatctc tacatgccta | 900 |
| ggaaaaagcc atgacaagag caatcagttc aaaaggtgta tgcaaaaaac cacataatag | 960 |
| taactagtac tgcattgcca ggaaggaagt tatgtcgcca ttccatggat ctcattctca | 1020 |
| tttccttgca g | 1031 |

<210> SEQ ID NO 40
<211> LENGTH: 396
<212> TYPE: DNA
<213> ORGANISM: Artificial Sequence
<220> FEATURE:

<223> OTHER INFORMATION: Chicken ovalbumin gene Exon 8

<400> SEQUENCE: 40

```
cttgagagta taatcaactt tgaaaaactg actgaatgga ccagttctaa tgttatggaa      60
gagaggaaga tcaaagtgta cttacctcgc atgaagatgg aggaaaaata caacctcaca     120
tctgtcttaa tggctatggg cattactgac gtgtttagct cttcagccaa tctgtctggc     180
atctcctcag cagagagcct gaagatatct caagctgtcc atgcagcaca tgcagaaatc     240
aatgaagcag cagagaggt ggtagggtca gcagaggctg gagtggatgc tgcaagcgtc      300
tctgaagaat ttagggctga ccatccattc ctcttctgta tcaagcacat cgcaaccaac     360
gccgttctct tctttggcag atgtgtttcc ccttaa                                396
```

<210> SEQ ID NO 41
<211> LENGTH: 20
<212> TYPE: DNA
<213> ORGANISM: Artificial Sequence
<220> FEATURE:
<223> OTHER INFORMATION: 3'-UTR from Chicken Ovalbumin gene Exon 8

<400> SEQUENCE: 41

```
aaagaagaaa gctgaaaaac                                                  20
```

<210> SEQ ID NO 42
<211> LENGTH: 627
<212> TYPE: DNA
<213> ORGANISM: Artificial Sequence
<220> FEATURE:
<223> OTHER INFORMATION: 3'-UTR from Chicken Ovalbumin gene  Exon 8

<400> SEQUENCE: 42

```
tctgtccctt ccaacaagac ccagagcact gtagtatcag gggtaaaatg aaaagtatgt      60
tatctgctgc atccagactt cataaaagct ggagcttaat ctagaaaaaa aatcagaaag     120
aaattacact gtgagaacag gtgcaattca cttttccttt acacagagta atactggtaa     180
ctcatggatg aaggcttaag ggaatgaaat tggactcaca gtactgagtc atcacactga     240
aaaatgcaac ctgatacatc agcagaaggt ttatggggga aaaatgcagc cttccaatta     300
agccagatat ctgtatgacc aagctgctcc agaattagtc actcaaaatc tctcagatta     360
aattatcaac tgtcaccaac cattcctatg ctgacaaggc aattgcttgt tctctgtgtt     420
cctgatacta caaggctctt cctgacttcc taaagatgca ttataaaaat cttataattc     480
acatttctcc ctaaactttg actcaatcat ggtatgttgg caaatatggt atattactat     540
tcaaattgtt ttccttgtac ccatatgtaa tgggtcttgt gaatgtgctc ttttgttcct     600
ttaatcataa taaaaacatg tttaagc                                         627
```

<210> SEQ ID NO 43
<211> LENGTH: 647
<212> TYPE: DNA
<213> ORGANISM: Artificial Sequence
<220> FEATURE:
<223> OTHER INFORMATION: 3'-UTR from Chicken Ovalbumin gene Exon 8

<400> SEQUENCE: 43

```
aaagaagaaa gctgaaaaac tctgtccctt ccaacaagac ccagagcact gtagtatcag      60
gggtaaaatg aaaagtatgt tctctgctgc atccagactt cataaaagct ggagcttaat     120
ctagaaaaaa aatcagaaag aaattacact gtgagaacag gtgcaattca cttttccttt     180
acacagagta atactggtaa ctcatggatg aaggcttaag ggaatgaaat tggactcaca     240
```

```
gtactgagtc atcacactga aaaatgcaac ctgatacatc agcagaaggt ttatggggga    300
aaaatgcagc cttccaatta agccagatat ctgtatgacc aagctcctcc agaattagtc    360
actcaaaatc tctcagatta aattatcaac tgtcaccaac tattcctatg ctgacaaggc    420
aattgcttgt tctctgtgtt cctgatacta caaggctctt cctgacttcc taaagatgca    480
ttataaaaat cttataattc acatttctcc ctaaactttg actcaatcat ggtatgttgg    540
caaatatggt atattactat tcaaattgtt ttccttgtac ccatatgtaa tgggtcttgt    600
gaatgtgctc ttttgttcct ttaatcataa taaaaacatg tttaagc                  647
```

```
<210> SEQ ID NO 44
<211> LENGTH: 687
<212> TYPE: DNA
<213> ORGANISM: Artificial Sequence
<220> FEATURE:
<223> OTHER INFORMATION: Chicken Ovalbumin gene downstream flanking
      sequence

<400> SEQUENCE: 44
```

```
aaacactttt cacttgtagt atttgaagta cagcaaggtt gtgtagcagg gaaagaatga    60
catgcagagg aataagtatg gacacacagg ctagcagcga ctgtagaaca agtactaatg    120
ggtgagaagt tgaacaagag tccCctacag caacttaatc taataagcta gtggtctaca    180
tcagctaaaa gagcatagtg agggatgaaa ttggttctcc tttctaagca tcacctggga    240
caactcatct ggagcagtgt gtccaatctg ccgctgccct gatcctggct ggggtgatgg    300
gacagacctt ggctgccact gagacatctg agacactgag atctgtctca actcagattt    360
acccaagaac agatcattgc caacagaaca aaatctcaaa cttatggcta gtgatgacag    420
cagtcagttg tcccatctgt gacccaccaa ggctggcatg ctggaatgag caggctttgg    480
tggcttgtag ttactggaca gcaccactga catgggcagg ggaaaaactg agcatggtgt    540
aaatcactgc ctcaaagcca cttctctgtg cctgcaccat gcttgaaagc tcttctacag    600
gagctgggtt tgttcaagaa agcttctgtt tctcccatct gcttcttgta ccttcacagg    660
gacagagtta gaagggtaca gccatgg                                         687
```

```
<210> SEQ ID NO 45
<211> LENGTH: 36
<212> TYPE: DNA
<213> ORGANISM: Artificial Sequence
<220> FEATURE:
<223> OTHER INFORMATION: GSG linker

<400> SEQUENCE: 45
ttggatccct accggtgctg cggccgcgca gttaac                               36
```

```
<210> SEQ ID NO 46
<211> LENGTH: 57
<212> TYPE: DNA
<213> ORGANISM: Artificial Sequence
<220> FEATURE:
<223> OTHER INFORMATION: P2A sequence

<400> SEQUENCE: 46
gctactaact tcagcctgct gaagcaggct ggagacgtgg aggagaaccc tggacct        57
```

```
<210> SEQ ID NO 47
<211> LENGTH: 8332
<212> TYPE: DNA
<213> ORGANISM: Artificial Sequence
```

```
<220> FEATURE:
<223> OTHER INFORMATION: Ovalbumin gene OV Construct 1hCECR1

<400> SEQUENCE: 47
aaagtgccac ctgacgtcga cggttatcca cagaatcagg ggataacgca ggaaagaaca      60
tgtgcgcatg cctgctattg tcttcccaat cctcccccct gctgtcctgc cccaccccac     120
cccccagaat agaatgacac ctactcagac aatgcgatgc aatttcctca ttttattagg     180
aaaggacagt gggagtggca ccttccaggg tcaaggaagg cacgggggag gggcaaacaa     240
cagatggctg gcaactagaa ggcacagtcg aggctgatca gcgagctcta gcatttaggt     300
gacactatag aatagggccc tctagcgaat taattcaggt tgttaacaac aacaattttc     360
gaaggtacct caggcaccgg gcttgcgggt catgcaccag gtgcgcggtc cttcgggcac     420
ctcgacgtcg gcggtgacgg tgaagccgag ccgctcgtag aaggggaggt tgcggggcgc     480
ggaggtctcc aggaaggcgg gcaccccggc gcgctcggcc gcctccactc cggggagcac     540
gacggcgctg cccagaccct tgccctggtg gtcgggcgag acgccgacgg tggccaggaa     600
ccacgcgggc tccttgggcc ggtgcggcgc caggaggcct tccatctgtt gctgcgcggc     660
cagccgggaa ccgctcaact cggccatgcg cgggccgatc tcggcgaaca ccgcccccgc     720
ttcgacgctc tccggcgtgg tccagaccgc caccgcggcg ccgtcgtccg cgacccacac     780
cttgccgatg tcgagcccga cgcgcgtgag gaagagttct gcagctcgg tgacccgctc      840
gatgtggcgg tccgggtcga cggtgtggcg cgtggcgggg tagtcggcga acgcggcggc     900
gagggtgcgt acggcccggg ggacgtcgtc gcgggtggcg aggcgcaccg tgggcttgta     960
ctcggtcatg gtaccagctt tttgcaaaag cctaggcctc caaaaaagcc tcctcactac    1020
ttctggaata gctcagaggc agaggcggcc tcggcctctg cataaataaa aaaaattagt    1080
cagccatggg gcggagaatg ggcggaactg ggcggagtta ggggcgggat gggcggagtt    1140
aggggcggga ctatggttgc tgactaattg agatgcatgc tttgcatact tctgcctgct    1200
ggggagcctg gggactttcc acacctggtt gctgactaat tgagatgcat gctttgcata    1260
cttctgcctg ctggggagcc tggggacttt ccacacccta actgacacac attccacaga    1320
catgtgagca aaaggccagc aaaaggacta gttattgata tctatacaca aattattagt    1380
gtttgattga caccagatga cagagaagtg catctgagaa aacctattcc caatctcctt    1440
tctctttctg cagactgaca tgcatttcat aggtagagat aacatttact gggaagcaca    1500
tctatcatca caaaaagcag gcaagatttt cagactttct tagtggctga aatagaagca    1560
aaagacgtga ttaaaaacaa aatgaaacaa aaaaaatcag ttgatacctg tggtgtagac    1620
atccagcaaa aaatatattat ttgcactacc atcttgtctt aagtcctcag acttggcaag    1680
gagaatgtag atttccacag tatatatgtt ttcacaaaag gaaggagaga aacaaaagaa    1740
aatggcactg actaaacttc agctagtggt ataggaaagt aattctgctt aacagagatt    1800
gcagtgatct ctatgtatgt cctgaagaat tatgttgtac ttttttcccc cattttttaaa    1860
tcaaacagtg ctttacagag gtcagaatgg tttctttact gtttgtcaat tctattatttt   1920
caatacagaa caatagcttc tataactgaa atatatttgc tatttgtatat tatgattgtc    1980
cctcgaacca tgaacactcc tccagctgaa tttcacaatt cctctgtcat ctgccaggcc    2040
attaagttat tcatggaaga tctttgagga acactgcaag ttcatatcat aaacacattt    2100
gaaattgagt attgttttgc attgtatgga gctatgtttt gctgtatcct cagaaaaaaa    2160
gtttgttata aagcattcac acccataaaa agatagattt aaatattcca actataggaa    2220
```

```
agaaagtgcg tctgctcttc actctagtct cagttggctc cttcacatgc acgcttcttt    2280
atttctccta ttttgtcaag aaaataatag gtcacgtctt gttctcactt atgtcctgcc    2340
tagcatggct cagatgcacg ttgtacatac aagaaggatc aaatgaaaca gacttctggt    2400
ctgttactac aaccatagta ataagcacac taactaataa ttgctaatta tgttttccat    2460
ctccaaggtt cccacatttt tctgttttct aaagatccc  attatctggt tgtaactgaa    2520
gctcaatgga acatgagcaa tatttcccag tcttctctcc catccaacag tcctgatgga    2580
ttagcagaac aggcagaaaa cacattgtta cccagaatta aaaactaata tttgctctcc    2640
attcaatcca aaatggacct attgaaacta aaatctaacc caatcccatt aaatgatttc    2700
tatggcgtca aaggtcaaac ttctgaaggg aacctgtggg tgggtcacaa ttcaggctat    2760
atattcccca gggctcagcc agtgtctgtt tggatcccta ccggtgctgc ggccgcgcag    2820
ttaacgaatt cgccaccatg ttggtggatg cccatctga gcggccagcc ctgtgcttct    2880
tgctgttggc tgtggcaatg tctttcttcg gctctgctct atccatagat gaaacacggg    2940
cgcatctgtt gttgaaagaa aagatgatgc ggctggggg gcggctggtg ctgaacacca    3000
aggaggagct ggccaatgag aggctcatga cgctcaaaat cgctgagatg aaggaggcca    3060
tgaggaccct gatattccca cccagcatgc acttttttcca ggccaagcat ctcattgaga    3120
gaagtcaagt gtttaatatt ctaaggatga tgccaaaagg ggctgccttg cacctccatg    3180
acattggcat cgtgactatg gactggctgg tgaggaatgt cacctacagg cctcactgcc    3240
acatctgttt caccccaagg gggatcatgc agttcagatt tgctcaccca actcccgtc    3300 catcagaaaa atgttccaag tggattctgc tggaggatta tcggaagcgg gtgcagaacg    3360
tcactgagtt tgatgacagc ttgctgagga atttcactct ggtgacccag cacccggagg    3420 tgatttcac  aaaccaaaat gttgtctggt cgaaatttga aaccatcttc ttcaccatct    3480
ctggtctcat ccattacgct ccagtgttca gagactatgt cttccggagc atgcaggagt    3540
tctacgagga caacgtgctc tacatggaga tcagagccag gctgctgccg gtgtatgagc    3600
tcagtggaga gcaccatgac gaagagtggt cagtgaagac ttatcaggaa gtagctcaga    3660
agtttgtgga aactcatcct gagtttattg gaatcaaaat catttattcg gatcacagat    3720
ccaaagatgt ggctgtcatc gcagaatcca tccgaatggc catggggctc cgaatcaagt    3780
tccccacggt ggtggcaggg tttgacctgg tggggcatga ggacactggc cactccttgc    3840
atgactacaa ggaagctctg atgatcccg  ccaaggatgg cgttaagctg ccttacttct    3900
tccacgccgg agaaacagac tggcagggta cttccataga caggaacatt ctggatgctc    3960
tgatgctgaa cactaccaga atcggccatg gatttgcttt gagcaaacac cccgcagtca    4020
ggacttattc ctggaaaaag gacatcccca tagaagtctg tcccatctct aaccaggtgc    4080
tgaaactggt gtctgacttg aggaaccacc ctgtagccac tctgatggcc actgggcacc    4140
ccatggtgat cagctctgat gacccagcta tgtttggtgc caaaggcttg tcctatgatt    4200
tctatgaggt cttcatgggc attggggga tgaaggctga tctgaggacc ctcaaacagc    4260
tggccatgaa ctctatcaag tacagtaccc tgttggagag tgagaaaaat actttcatgg    4320
aaatatggaa gaagagatgg gataagttca tagcagatgt ggctacaaag tgaagatctt    4380
tggatcccta ccggtgctgc ggccgcgcag ttaacgccgc ccctctccct ccccccccc     4440 taacgttact ggccgaagcc gcttggaata aggccggtgt gcgtttgtct atatgttatt    4500
ttccaccata ttgccgtctt ttggcaatgt gagggcccgg aaacctggcc ctgtcttctt    4560
gacgagcatt cctaggggtc tttcccctct cgccaaagga atgcaaggtc tgttgaatgt    4620
```

```
cgtgaaggaa gcagttcctc tggaagcttc ttgaagacaa acaacgtctg tagcgaccct   4680
ttgcaggcag cggaaccccc cacctggcga caggtgcctc tgcggccaaa agccacgtgt   4740
ataagataca cctgcaaagg cggcacaacc ccagtgccac gttgtgagtt ggatagttgt   4800
ggaaagagtc aaatggctct cctcaagcgt attcaacaag gggctgaagg atgcccagaa   4860
ggtaccccat tgtatgggat ctgatctggg gcctcggtac acatgcttta catgtgttta   4920
gtcgaggtta aaaaaacgtc taggccccc gaaccacggg gacgtggttt tcctttgaaa     4980
aacacgatga taatatggcc acaacataca gctagaaagc tgtattgcct ttagcactca   5040
agctcaaaag gtaagcaact ctctggaatt accttctctc tatattagct cttacttgca   5100
cctaaacttt aaaaaattaa caattattgt gttatgtgtt gtatctttaa gggtgaagta   5160
cctgcgtgat accccctata aaacttctc acctgtgtat gcattctgca ctatttatt    5220 atgtgtaaaa gctttgtgtt tgttttcagg aggcttattc tttgtgctta aatatgttt    5280 ttaatttcag aacatcttat cctgtcgttc actatctgat atgctttgca gtttgcttga   5340
ttaacttcta gccctacaga gtgcacagag agcaaaatca tggtgttcag tgaattctgg   5400
ggagttattt taatgtgaaa attctctaga agtttaattc ctgcaaagtg cagctgctga   5460
tcactacaca agataaaaat gtgggggggtg cataaacgta tattcttaca ataatagata   5520
catgtgaact tgtatacaga aaagaaaatg agaaaaatgt gtgtgcgtat actcacacac   5580
gtggtcagta aaaacttttg aggggtttaa tacagaaaat ccaatcctga ggccccagca   5640
ctcagtacgc atataaaggg ctgggctctg aaggacttct gactttcaca gattatataa   5700
atctcaggaa agcaactaga ttcatgctgg ctccaaaagc tgtgctttat ataagcacac   5760
tggctataca atagttgtac agttcagctc tttataatag aaacagacag aacaagtata   5820
aatcttctat tggtctatgt catgaacaag aattcattca gtggctctgt tttatagtaa   5880
acattgctat tttatcatgt ctgcatttct cttctgtctg aatgtcacca ctaaaattta   5940
actccacaga aagtttatac tacagtacac atgcatatct ttgagcaaag caaaccatac   6000
ctgaaagtgc aatagagcag aatatgaatt acatgcgtgt cttctcccta gactacatga   6060
ccccatataa attcattcc ttatctattc tgccatcacc aaaacaaagg taaaaatact     6120
tttgaagatc tactcatagc aagtagtgtg caacaaacag atatttctct acatttattt   6180
ttagggaata aaaataagaa ataaaatagt cagcaagcct ctgctttctc atatatctgt   6240
ccaaacctaa agtttactga aatttgctct ttgaatttcc agttttgcaa gcctatcaga   6300
ttgtgtttta atcagaggta ctgaaaagta tcaatgaatt ctgatatcgt cgtgccagct   6360
gcattaatga atcggccaac gcgcggggag aggcggtttg cgtattgggc gctcttccgc   6420
ttcctcgctc actgactcgc tgcgctcggt cgttcggctg cggcgagcgg tatcagctca   6480
ctcaaaggcg gtaatacggt tatccacaga atcagggat aacgcaggaa agaacatgtg     6540
agcaaaaggc cagcaaaagg ccaggaaccg taaaaaggcc gcgttgctgg cgttttccca   6600
taggctccgc cccctgacg agcatcacaa aaatcgatgc tcaagtcaga ggtggcgaaa    6660
cccgacagga ctataaagat accaggcgtt tccccctgga agctccctcg tgcgctctcc   6720
tgttccgacc ctgccgctta ccggatacct gtccgccttt ctcccttcgg gaagcgtggc   6780
gctttctcat agctcacgct gtaggtatct cagttcggtg taggtcgttc gctccaagct   6840
gggctgtgtg cacgaacccc ccgttcagcc cgaccgctgc gccttatccg gtaactatcg   6900
tcttgagtcc aacccggtaa gacacgactt atcgccactg gcagcagcca ctggtaacag   6960
```

```
gattagcaga gcgaggtatg taggcggtgc tacagagttc ttgaagtggt ggcctaacta   7020
cggctacact agaagaacag tatttggtat ctgcgctctg ctgaagccag ttaccttcgg   7080
aaaaagagtt ggtagctctt gatccggcaa acaaaccacc gctggtagcg gtggttttt   7140 tgtttgcaag cagcagatta cgcgcagaaa aaaaggatct caagaagatc ctttgatctt   7200
ttctacgggg tctgacgctc agtggaacga aaactcacgt taagggattt tggtcatgag   7260
attatcaaaa aggatcttca cctagatcct tttaaattaa aaatgaagtt ttaaatcaat   7320
ctaaagtata tatgagtaaa cttggtctga cagttaccaa tgcttaatca gtgaggcacc   7380
tatctcagcg atctgtctat ttcgttcatc catagttgcc tgactccccg tcgtgtagat   7440
aactacgata cgggagggct taccatctgg ccccagtgct gcaatgatac cgcgagaccc   7500
acgctcaccg gctccagatt tatcagcaat aaaccagcca gccggaaggg ccgagcgcag   7560
aagtggtcct gcaactttat ccgcctccat ccagtctatt aattgttgcc gggaagctag   7620
agtaagtagt tcgccagtta atagtttgcg caacgttgtt gccattgcta caggcatcgt   7680
ggtgtcacgc tcgtcgtttg gtatggcttc attcagctcc ggttcccaac gatcaaggcg   7740
agttacatga tcccccatgt tgtgcaaaaa agcggttagc tccttcggtc ctccgatcgt   7800
tgtcagaagt aagttggccg cagtgttatc actcatggtt atggcagcac tgcataattc   7860
tcttactgtc atgccatccg taagatgctt ttctgtgact ggtgagtact caaccaagtc   7920
attctgagaa tagtgtatgc ggcgaccgag ttgctcttgc ccggcgtcaa tacgggataa   7980
taccgcgcca catagcagaa ctttaaaagt gctcatcatt ggaaaacgtt cttcggggcg   8040
aaaactctca aggatcttac cgctgttgag atccagttcg atgtaaccca ctcgtgcacc   8100
caactgatct tcagcatctt ttactttcac cagcgtttct gggtgagcaa aaacaggaag   8160
gcaaaatgcc gcaaaaaagg gaataagggc gacacgaaaa tgttgaatac tcatactctt   8220 ccttttcaa tattattgaa gcatttatca gggttattgt ctcatgagcg gatacatatt   8280
tgaatgtatt tagaaaaata aacaaatagg ggttccgcgc acatttcccc ga            8332
```

<210> SEQ ID NO 48
<211> LENGTH: 8518
<212> TYPE: DNA
<213> ORGANISM: Artificial Sequence
<220> FEATURE:
<223> OTHER INFORMATION: Ovalbumin gene  OV Construct 2 hCECR1

<400> SEQUENCE: 48

```
aaagtgccac ctgacgtcga cggttatcca cagaatcagg ggataacgca ggaaagaaca     60
tgtgcgcatg cctgctattg tcttcccaat cctccccctt gctgtcctgc cccacccac    120 cccccagaat agaatgacac ctactcagac aatgcgatgc aatttcctca ttttattagg    180
aaaggacagt gggagtggca ccttccaggg tcaaggaagg cacggggag gggcaaacaa     240 cagatggctg gcaactagaa ggcacagtcg aggctgatca gcgagctcta gcatttaggt    300
gacactatag aatagggccc tctagcgaat taattcaggt tgttaacaac aacaattttc    360
gaaggtacct caggcaccgg gcttgcgggt catgcaccag gtgcgcggtc cttcgggcac    420
ctcgacgtcg gcggtgacgg tgaagccgag ccgctcgtag aagggaggt tgcggggcgc    480 ggaggtctcc aggaaggcgg gcaccccggc gcgctcggcc gcctccactc cggggagcac    540
gacggcgctg cccagaccct tgccctggtg gtcgggcgag acgccgacgg tggccaggaa    600
ccacgcgggc tccttgggcc ggtgcggcgc caggaggcct tccatctgtt gctgcgcggc    660
cagccgggaa ccgctcaact cggccatgcg cgggccgatc tcggcgaaca ccgcccccgc    720
```

```
ttcgacgctc tccggcgtgg tccagaccgc caccgcggcg ccgtcgtccg cgacccacac    780
cttgccgatg tcgagcccga cgcgcgtgag gaagagttct tgcagctcgg tgacccgctc    840
gatgtggcgg tccgggtcga cggtgtggcg cgtggcgggg tagtcggcga acgcggcggc    900
gagggtgcgt acggcccggg ggacgtcgtc gcgggtggcg aggcgcaccg tgggcttgta    960
ctcggtcatg gtaccagctt tttgcaaaag cctaggcctc caaaaaagcc tcctcactac   1020
ttctggaata gctcagaggc agaggcgcc tcggcctctg cataaataaa aaaaattagt    1080
cagccatggg gcggagaatg ggcggaactg ggcggagtta ggggcgggat gggcggagtt   1140
aggggcggga ctatggttgc tgactaattg agatgcatgc tttgcatact tctgcctgct   1200
ggggagcctg gggactttcc acacctggtt gctgactaat tgagatgcat gctttgcata   1260
cttctgcctg ctggggagcc tggggacttt ccacaccta actgacacac attccacaga    1320
catgtgagca aaaggccagc aaaaggacta gttattgata tcagtacctg cgtgataccc   1380
cctataaaaa cttctcacct gtgtatgcat tctgcactat tttattatgt gtaaaagctt   1440
tgtgtttgtt ttcaggaggc ttattctttg tgcttaaaat atgttttaa tttcagaaca    1500 tcttatcctg tcgttcacta tctgatatgc tttgcagttt gcttgattaa cttctagccc   1560
tacagagtgc acagagagca aaatcatggt gttcagtgaa ttctggggag ttattttaat   1620
gtgaaaattc tctagaagtt taattcctgc aaagtgcagc tgctgatcac tacacaagat   1680
aaaaatgtgg ggggtgcata acgtatatt cttacaataa tagatacatg tgaacttgta    1740
tacagaaaag aaaatgagaa aaatgtgtgt gcgtatactc acacacgtgg tcagtaaaaa   1800
cttttgaggg gtttaataca gaaaatccaa tcctgaggcc ccagcactca gtacgcatat   1860
aaagggctgg gctctgaagg acttctgact ttcacagatt atataaatct caggaaagca   1920
actagattca tgctggctcc aaaagctgtg ctttatataa gcacactggc tatacaatag   1980
ttgtacagtt cagctctta taatagaaac agacagaaca agtataaatc ttctattggt    2040
ctatgtcatg aacaagaatt cattcagtgg ctctgttta tagtaaacat tgctatttta    2100
tcatgtctgc atttctcttc tgtctgaatg tcaccactaa aatttaactc cacagaaagt   2160
ttatactaca gtacacatgc atatctttga gcaaagcaaa ccatacctga aagtgcaata   2220
gagcagaata tgaattacat gcgtgtcttt ctcctagact acatgacccc atataaatta   2280
cattccttat ctattctgcc atcaccaaaa caaaggtaaa aatactttg aagatctact    2340 catagcaagt agtgtgcaac aaacagatat ttctctacat ttattttag ggaataaaaa    2400 taagaaataa aatagtcagc aagcctctgc tttctcatat atctgtccaa acctaaagtt   2460
tactgaaatt tgctctttga atttccagtt ttgcaagcct atcagattgt gttttaatca   2520
gaggtactga aaagtatcaa tgaattctag ctttcactga acaaaaatat gtagaggcaa   2580
ctggcttctg ggacagtttg ctacccaaaa gacaactgaa tgcaaataca taaatagatt   2640
tatgaatatg gttttgaaca tgcacatgag aggtggatat agcaacagac acattaccac   2700
agaattactt taaaactact tgttaacatt taattgccta aaaactgctc gtaatttact   2760
gttgtagcct accatagagt accctgcatg gtactatgta cagcattcca tccttacatt   2820
ttcactgttc tgctgtttgc tctagacaac tcagagttca ccatgttggt ggatggccca   2880
tctgagcggc cagccctgtg cttcttgctg ttggctgtgg caatgtcttt cttcggctct   2940
gctctatcca tagatgaaac acgggcgcat ctgttgttga agaaaagat gatgcggctg    3000 gggggcggc tggtgctgaa caccaaggag gagctggcca atgagaggct catgacgctc   3060
```

| | |
|---|---|
| aaaatcgctg agatgaagga ggccatgagg accctgatat tcccacccag catgcacttt | 3120 |
| ttccaggcca agcatctcat tgagagaagt caagtgttta atattctaag gatgatgcca | 3180 |
| aaagggctg ccttgcacct ccatgacatt ggcatcgtga ctatggactg gctggtgagg | 3240 |
| aatgtcacct acaggcctca ctgccacatc tgtttcaccc caaggggat catgcagttc | 3300 |
| agatttgctc acccaactcc ccgtccatca gaaaaatgtt ccaagtggat tctgctggag | 3360 |
| gattatcgga agcgggtgca gaacgtcact gagtttgatg acagcttgct gaggaatttc | 3420 |
| actctggtga cccagcaccc ggaggtgatt tacacaaacc aaaatgttgt ctggtcgaaa | 3480 |
| tttgaaacca tcttcttcac catctctggt ctcatccatt acgctccagt gttcagagac | 3540 |
| tatgtcttcc ggagcatgca ggagttctac gaggacaacg tgctctacat ggagatcaga | 3600 |
| gccaggctgc tgccggtgta tgagctcagt ggagagcacc atgacgaaga gtggtcagtg | 3660 |
| aagacttatc aggaagtagc tcagaagttt gtggaaactc atcctgagtt tattggaatc | 3720 |
| aaaatcattt attcggatca cagatccaaa gatgtggctg tcatcgcaga atccatccga | 3780 |
| atggccatgg ggctccgaat caagttcccc acgtggtgg cagggtttga cctggtgggg | 3840 |
| catgaggaca ctggccactc cttgcatgac tacaaggaag ctctgatgat ccccgccaag | 3900 |
| gatggcgtta agctgcctta cttcttccac gccggagaaa cagactggca gggtacttcc | 3960 |
| atagacagga acattctgga tgctctgatg ctgaacacta ccagaatcgg ccatggattt | 4020 |
| gctttgagca aacaccccgc agtcaggact tattcctgga aaaggacat ccccatagaa | 4080 |
| gtctgtccca tctctaacca ggtgctgaaa ctggtgtctg acttgaggaa ccaccctgta | 4140 |
| gccactctga tggccactgg gcaccccatg gtgatcagct ctgatgaccc agctatgttt | 4200 |
| ggtgccaaag gcttgtccta tgatttctat gaggtcttca tgggcattgg ggggatgaag | 4260 |
| gctgatctga ggaccctcaa acagctggcc atgaactcta tcaagtacag taccctgttg | 4320 |
| gagagtgaga aaaatacttt catggaaata tggaagaaga gatgggataa gttcatagca | 4380 |
| gatgtggcta caaagtgaag atctttggat ccctaccggt gctgcggccg cgcagttaac | 4440 |
| gccgcccctc tccctccccc cccctaacg ttactggccg aagccgcttg gaataaggcc | 4500 |
| ggtgtgcgtt tgtctatatg ttattttcca ccatattgcc gtcttttggc aatgtgaggg | 4560 |
| cccggaaacc tggccctgtc ttcttgacga gcattcctag gggtcttttcc cctctcgcca | 4620 |
| aaggaatgca aggtctgttg aatgtcgtga aggaagcagt tcctctggaa gcttcttgaa | 4680 |
| gacaaacaac gtctgtagcg accctttgca ggcagcggaa ccccccacct ggcgacaggt | 4740 |
| gcctctgcgg ccaaaagcca cgtgtataag atacacctgc aaaggcggca aaccccagt | 4800 |
| gccacgttgt gagttggata gttgtggaaa gagtcaaatg gctctcctca gcgtattca | 4860 |
| acaagggct gaaggatgcc cagaaggtac cccattgtat gggatctgat ctggggcctc | 4920 |
| ggtacacatg ctttacatgt gtttagtcga ggttaaaaaa acgtctaggc cccccgaacc | 4980 |
| acggggacgt ggttttcctt tgaaaaacac gatgataata tggccacatc agagttcacc | 5040 |
| atgggctcca tcggtgcagc aagcatggaa ttttgttttg atgtattcaa ggagctcaaa | 5100 |
| gtccaccatg ccaatgagaa catcttctac tgccccattg ccatcatgtc agctctagcc | 5160 |
| atggtatacc tgggtgcaaa agacagcacc aggacacaaa taataaggt gagcctacag | 5220 |
| ttaaagatta aacctttgc cctgctcaat ggagccacag cacttaattg tatgataatg | 5280 |
| tcccttggaa actgcatagc tcagaggctg aaaatctgaa accagagtta tctaaaagtg | 5340 |
| tggccacctc caactcccag agtgttaccc aaatgcacta gctagaaatc ttgaaactgg | 5400 |
| attgcataac ttcttttgt cataaccatt atttcagcta ctattatttt caattacagg | 5460 |

```
ttgttcgctt tgataaactt ccaggattcg gagacagtat tgaagctcag gtacagaaat    5520
aatttcacct ccttctctat gtcccttcc  tctggaagca aaatacagca gatgaagcaa    5580
tctcttagct gttccaagcc ctctctgatg agcagctagt gctctgcatc cagcagttgg    5640
gagaacactg ttcataagaa cagagaaaaa gaaggaagta acaggggatt cagaacaaac    5700
agaagataaa actcaggaca aaaataccgt gtgaatgagg aaacttgtgg atatttgtac    5760
gcttaagcaa gacagctaga tgattctgga taaatgggtc tggttggaaa agaaggaaag    5820
cctggctgat ctgctggagc tagattattg cagcaggtag gcaggagttc cctagagaaa    5880
agtatgaggg aattacagaa gaaaacagc  acaaaattgt aaatattgga aaaggaccac    5940
atcagtgtag ttactagcag taagacagac aggatgaaaa atagttttgt aaacagaagt    6000
atctaactac tttactctgt tcatacacta cgtaaaacct actaagtaat aaaactagaa    6060
taacaacatc tttctttctc tttgtattca gtgtggcaca tctgtaaacg ttcactcttc    6120
acttagagac atcctcaacc aaatcaccaa accaaatgat gtttattcgt tcagccttgc    6180
cagtagactt tatgctgaag agagataccc aatcctgcca gtaagttgct ctaaaatctg    6240
atctgagtgt atttccatgc caaagctcta ccattctgta atgcaaaaac agtcagagtt    6300
ccacatgttt cactaagaaa atttcttttt ctcttgtttt tacaaatgaa agagaggaca    6360
aataacattt ctctatcacc gacctgaaac tctacagtct tcagaatg   aatggcttgc    6420 taaaagaatg tcaaatctta ccatacagct atttcatatt acactactaa atacactata    6480
aggcatagca tgtagtaata cagtgtaaaa tagcttttta cactactaga tatcgtcgtg    6540
ccagctgcat taatgaatcg gccaacgcgc ggggagaggc ggtttgcgta ttgggcgctc    6600
ttccgcttcc tcgctcactg actcgctgcg ctcggtcgtt cggctgcggc gagcggtatc    6660
agctcactca aaggcggtaa tacggttatc cacagaatca ggggataacg caggaaagaa    6720
catgtgagca aaaggccagc aaaaggccag gaaccgtaaa aaggccgcgt tgctggcgtt    6780
tttccatagg ctccgccccc ctgacgagca tcacaaaaat cgatgctcaa gtcagaggtg    6840
gcgaaacccg acaggactat aaagatacca ggcgtttccc cctggaagct ccctcgtgcg    6900
ctctcctgtt ccgaccctgc cgcttaccgg atacctgtcc gcctttctcc cttcgggaag    6960
cgtggcgctt tctcatagct cacgctgtag gtatctcagt tcggtgtagg tcgttcgctc    7020
caagctgggc tgtgtgcacg aacccccgt  tcagcccgac cgctgcgcct tatccggtaa    7080
ctatcgtctt gagtccaacc cggtaagaca cgacttatcg ccactggcag cagccactgg    7140
taacaggatt agcagagcga ggtatgtagg cggtgctaca gagttcttga agtggtggcc    7200
taactacggc tacactagaa gaacagtatt tggtatctgc gctctgctga agccagttac    7260
cttcggaaaa agagttggta gctcttgatc cggcaaacaa accaccgctg gtagcggtgg    7320
tttttttgtt tgcaagcagc agattacgcg cagaaaaaaa ggatctcaag aagatccttt    7380
gatcttttct acgggtctg  acgctcagtg gaacgaaaac tcacgttaag ggattttggt    7440
catgagatta tcaaaaagga tcttcaccta gatccttta  aattaaaaat gaagttttaa    7500
atcaatctaa agtatatatg agtaaacttg gtctgacagt taccaatgct taatcagtga    7560
ggcacctatc tcagcgatct gtctatttcg ttcatccata gttgcctgac tccccgtcgt    7620
gtagataact acgatacggg agggcttacc atctggcccc agtgctgcaa tgataccgcg    7680
agacccacgc tcaccggctc cagatttatc agcaataaac cagccagccg aagggccga   7740 gcgcagaagt ggtcctgcaa ctttatccgc ctccatccag tctattaatt gttgccggga    7800
```

| | |
|---|---|
| agctagagta agtagttcgc cagttaatag tttgcgcaac gttgttgcca ttgctacagg | 7860 |
| catcgtggtg tcacgctcgt cgtttggtat ggcttcattc agctccggtt cccaacgatc | 7920 |
| aaggcgagtt acatgatccc ccatgttgtg caaaaaagcg gttagctcct tcggtcctcc | 7980 |
| gatcgttgtc agaagtaagt tggccgcagt gttatcactc atggttatgg cagcactgca | 8040 |
| taattctctt actgtcatgc catccgtaag atgcttttct gtgactggtg agtactcaac | 8100 |
| caagtcattc tgagaatagt gtatgcggcg accgagttgc tcttgcccgg cgtcaatacg | 8160 |
| ggataatacc gcgccacata gcagaacttt aaaagtgctc atcattggaa aacgttcttc | 8220 |
| ggggcgaaaa ctctcaagga tcttaccgct gttgagatcc agttcgatgt aacccactcg | 8280 |
| tgcacccaac tgatcttcag catctttac tttcaccagc gtttctgggt gagcaaaaac | 8340 |
| aggaaggcaa aatgccgcaa aaaagggaat aagggcgaca cggaaatgtt gaatactcat | 8400 |
| actcttcctt tttcaatatt attgaagcat ttatcagggt tattgtctca tgagcggata | 8460 |
| catatttgaa tgtatttaga aaaataaaca aataggggtt ccgcgcacat ttccccga | 8518 |

<210> SEQ ID NO 49
<211> LENGTH: 8348
<212> TYPE: DNA
<213> ORGANISM: Artificial Sequence
<220> FEATURE:
<223> OTHER INFORMATION: Ovalbumin gene OV Construct 3 hCECR1

<400> SEQUENCE: 49

| | |
|---|---|
| aaagtgccac ctgacgtcga cggttatcca cagaatcagg ggataacgca ggaaagaaca | 60 |
| tgtgcgcatg cctgctattg tcttcccaat cctcccccTT gctgtcctgc ccacccccac | 120 |
| cccccagaat agaatgacac ctactcagac aatgcgatgc aatttcctca ttttattagg | 180 |
| aaaggacagt gggagtggca ccttccaggg tcaaggaagg cacggggggag gggcaaacaa | 240 |
| cagatggctg gcaactagaa ggcacagtcg aggctgatca gcgagctcta gcatttaggt | 300 |
| gacactatag aatagggccc tctagcgaat taattcaggt tgttaacaac aacaattttc | 360 |
| gaaggtacct caggcaccgg gcttgcgggt catgcaccag gtgcgcggtc cttcgggcac | 420 |
| ctcgacgtcg gcggtgacgg tgaagccgag ccgctcgtag aagggggaggt tgcggggcgc | 480 |
| ggaggtctcc aggaaggcgg gcaccccggc gcgctcggcc gcctccactc cggggagcac | 540 |
| gacgcgctg cccagaccct tgccctggtg gtcgggcgag acgccgacgg tggccaggaa | 600 |
| ccacgcgggc tccttgggcc ggtgcggcgc caggaggcct tccatctgtt gctgcgcggc | 660 |
| cagccgggaa ccgctcaact cggccatgcg cgggccgatc tcggcgaaca ccgccccgc | 720 |
| ttcgacgctc tccggcgtgg tccagaccgc caccgcggcg ccgtcgtccg cgacccacac | 780 |
| cttgccgatg tcgagcccga cgcgcgtgag gaagagttct tgcagctcgg tgacccgctc | 840 |
| gatgtggcgg tccgggtcga cggtgtggcg cgtggcgggg tagtcggcga acgcggcggc | 900 |
| gagggtgcgt acggcccggg ggacgtcgtc gcgggtggcg aggcgcaccg tgggcttgta | 960 |
| ctcggtcatg gtaccagctt tttgcaaaag cctaggcctc caaaaaagcc tcctcactac | 1020 |
| ttctggaata gctcagaggc agaggcggcc tcggcctctg cataaataaa aaaaattagt | 1080 |
| cagccatggg gcgagaatg gcggaactg ggcggagtta ggggcgggat gggcggagtt | 1140 |
| aggggcggga ctatggttgc tgactaattg agatgcatgc tttgcatact tctgcctgct | 1200 |
| ggggagcctg gggactttcc acacctggtt gctgactaat tgagatgcat gctttgcata | 1260 |
| cttctgcctg ctggggagcc tggggacttt ccacacccta actgacacac attccacaga | 1320 |
| catgtgagca aaaggccagc aaaaggacta gttattgata tctatacaca aattattagt | 1380 |

```
gtttgattga caccagatga cagagaagtg catctgagaa aacctattcc caatctcctt    1440
tctctttctg cagactgaca tgcatttcat aggtagagat aacatttact gggaagcaca    1500
tctatcatca caaaaagcag gcaagatttt cagactttct tagtggctga aatagaagca    1560
aaagacgtga ttaaaaacaa aatgaaacaa aaaaatcag ttgatacctg tggtgtagac     1620
atccagcaaa aaatattat ttgcactacc atcttgtctt aagtcctcag acttggcaag     1680
gagaatgtag atttccacag tatatatgtt ttcacaaaag gaaggagaga acaaaagaa     1740 aatggcactg actaaacttc agctagtggt ataggaaagt aattctgctt aacagagatt    1800
gcagtgatct ctatgtatgt cctgaagaat tatgttgtac ttttttcccc catttttaaa    1860
tcaaacagtg ctttacagag gtcagaatgg tttctttact gtttgtcaat tctattattt    1920
caatacagaa caatagcttc tataactgaa atatatttgc tattgtatat tatgattgtc    1980
cctcgaacca tgaacactcc tccagctgaa tttcacaatt cctctgtcat ctgccaggcc    2040
attaagttat tcatggaaga tctttgagga acactgcaag ttcatatcat aaacacattt    2100
gaaattgagt attgttttgc attgtatgga gctatgtttt gctgtatcct cagaaaaaaa    2160
gtttgttata aagcattcac acccataaaa agatagattt aaatattcca actataggaa    2220
agaaagtgcg tctgctcttc actctagtct cagttggctc cttcacatgc acgcttcttt    2280
atttctccta ttttgtcaag aaaataatag gtcacgtctt gttctcactt atgtcctgcc    2340
tagcatggct cagatgcacg ttgtacatac aagaaggatc aaatgaaaca gacttctggt    2400
ctgttactac aaccatagta ataagcacac taactaataa ttgctaatta tgttttccat    2460
ctccaaggtt cccacatttt tctgtttct taaagatccc attatctggt tgtaactgaa      2520
gctcaatgga acatgagcaa tatttcccag tcttctctcc catccaacag tcctgatgga    2580
ttagcagaac aggcagaaaa cacattgtta cccagaatta aaaactaata tttgctctcc    2640
attcaatcca aaatggacct attgaaacta aaatctaacc caatcccatt aaatgatttc    2700
tatggcgtca aaggtcaaac ttctgaaggg aacctgtggg tgggtcacaa ttcaggctat    2760
atattcccca gggctcagcc agtgtctgta catacagcta gaaagctgta ttgcctttag    2820
cactcaagct caaaagacaa ctcagagttc accatgttgg tggatggccc atctgagcgg    2880
ccagccctgt gcttcttgct gttggctgtg gcaatgtctt tcttcggctc tgctctatcc    2940
atagatgaaa cacgggcgca tctgttgttg aaagaaaaga tgatgcggct ggggggggcgg    3000 ctggtgctga acaccaagga ggagctggcc aatgagaggc tcatgacgct caaaatcgct    3060
gagatgaagg aggccatgag gaccctgata ttcccaccca gcatgcactt tttccaggcc    3120
aagcatctca ttgagagaag tcaagtgttt aatattctaa ggatgatgcc aaaagggct     3180 gccttgcacc tccatgacat tggcatcgtg actatggact ggctggtgag gaatgtcacc    3240
tacaggcctc actgccacat ctgtttcacc ccaaggggga tcatgcagtt cagatttgct    3300
cacccaactc cccgtccatc agaaaaatgt tccaagtgga ttctgctgga ggattatcgg    3360
aagcgggtgc agaacgtcac tgagtttgat gacagcttgc tgaggaattt cactctggtg    3420
acccagcacc cggaggtgat ttacacaaac caaaatgttg tctggtcgaa atttgaaacc    3480
atcttcttca ccatctctgg tctcatccat tacgctccag tgttcagaga ctatgtcttc    3540
cggagcatgc aggagttcta cgaggacaac gtgctctaca tggagatcag agccaggctg    3600
ctgccggtgt atgagctcag tggagagcac catgacgaag agtggcagt gaagacttat    3660 caggaagtag ctcagaagtt tgtggaaact catcctgagt ttattggaat caaaatcatt    3720
```

```
tattcggatc acagatccaa agatgtggct gtcatcgcag aatccatccg aatggccatg   3780
gggctccgaa tcaagttccc cacggtggtg gcagggtttg acctggtggg gcatgaggac   3840
actggccact ccttgcatga ctacaaggaa gctctgatga tccccgccaa ggatggcgtt   3900
aagctgcctt acttcttcca cgccggagaa acagactggc agggtacttc catagacagg   3960
aacattctgg atgctctgat gctgaacact accagaatcg gccatggatt tgctttgagc   4020
aaacaccccg cagtcaggac ttattcctgg aaaaaggaca tccccataga agtctgtccc   4080
atctctaacc aggtgctgaa actggtgtct gacttgagga accaccctgt agccactctg   4140
atggccactg gcacccccat ggtgatcagc tctgatgacc cagctatgtt tggtgccaaa   4200
ggcttgtcct atgatttcta tgaggtcttc atgggcattg gggggatgaa ggctgatctg   4260
aggaccctca acagctggc catgaactct atcaagtaca gtaccctgtt ggagagtgag   4320
aaaaatactt tcatggaaat atggaagaag agatgggata agttcatagc agatgtggct   4380
acaaagtgaa gatctttgga tccctaccgg tgctgcggcc gcgcagttaa cgccgcccct   4440
ctccctcccc cccccctaac gttactggcc gaagccgctt ggaataaggc cggtgtgcgt   4500
ttgtctatat gttatttcc accatattgc cgtcttttgg caatgtgagg gcccggaaac   4560
ctggccctgt cttcttgacg agcattccta ggggtctttc ccctctcgcc aaaggaatgc   4620
aaggtctgtt gaatgtcgtg aaggaagcag ttcctctgga agcttcttga agacaaacaa   4680
cgtctgtagc gacccttgc aggcagcgga acccccacc tggcgacagg tgcctctgcg   4740
gccaaaagcc acgtgtataa gatacacctg caaaggcggc acaaccccag tgccacgttg   4800
tgagttggat agttgtggaa agagtcaaat ggctctcctc aagcgtattc aacaaggggc   4860
tgaaggatgc ccagaaggta ccccattgta tgggatctga tctggggcct cggtacacat   4920
gctttacatg tgtttagtcg aggttaaaaa aacgtctagg ccccccgaac cacggggacg   4980
tggtttttcct ttgaaaaaca cgatgataat atggccacaa catacagcta gaaagctgta   5040
ttgcctttag cactcaagct caaaaggtaa gcaactctct gcaattacct tctctctata   5100
ttagctctta cttgcaccta aactttaaaa aattaacaat tattgtgtta tgtgttgtat   5160
ctttaagggt gaagtacctg cgtgataccc cctataaaaa cttctcacct gtgtatgcat   5220
tctgcactat tttattatgt gtaaaagctt tgtgtttgtt ttcaggaggc ttattctttg   5280
tgcttaaaat atgttttaa tttcagaaca tcttatcctg tcgttcacta tctgatatgc   5340
tttgcagttt gcttgattaa cttctagccc tacagagtgc acagagagca aaatcatggt   5400
gttcagtgaa ttctggggag ttattttaat gtgaaaattc tctagaagtt taattcctgc   5460
aaagtgcagc tgctgatcac tacacaagat aaaaatgtgg ggggtgcata aacgtatatt   5520
cttacaataa tagatacatg tgaacttgta tacagaaaag aaaatgagaa aatgtgtgt   5580
gcgtatactc acacacgtgg tcagtaaaaa cttttgaggg gtttaataca gaaaatccaa   5640
tcctgaggcc ccagcactca gtacgcatat aaagggctgg gctctgaagg acttctgact   5700
ttcacagatt atataaatct caggaaagca actagattca tgctggctcc aaaagctgtg   5760
ctttatataa gcacactggc tatacaatag ttgtacagtt cagctctta taatagaaac   5820
agacagaaca agtataaatc ttctattggt ctatgtcatg aacaagaatt cattcagtgg   5880
ctctgtttta tagtaaacat tgctatttta tcatgtctgc atttctcttc tgtctgaatg   5940
tcaccactaa aatttaactc cacagaaagt ttatactaca gtacatgc atatctttga   6000
gcaaagcaaa ccatacctga aagtgcaata gagcagaata tgaattacat gcgtgtcttt   6060
ctcctagact acatgacccc atataaatta cattccttat ctattctgcc atcaccaaaa   6120
```

```
caaaggtaaa aatacttttg aagatctact catagcaagt agtgtgcaac aaacagatat    6180
ttctctacat ttattttag ggaataaaaa taagaaataa aatagtcagc aagcctctgc     6240
tttctcatat atctgtccaa acctaaagtt tactgaaatt tgctctttga atttccagtt    6300
ttgcaagcct atcagattgt gttttaatca gaggtactga aaagtatcaa tgaattctga    6360
tatcgtcgtg ccagctgcat taatgaatcg gccaacgcgc ggggagaggc ggtttgcgta    6420
ttgggcgctc ttccgcttcc tcgctcactg actcgctgcg ctcggtcgtt cggctgcggc    6480
gagcggtatc agctcactca aaggcggtaa tacggttatc cacagaatca ggggataacg    6540
caggaaagaa catgtgagca aaaggccagc aaaaggccag gaaccgtaaa aaggccgcgt    6600
tgctggcgtt tttccatagg ctccgccccc ctgacgagca tcacaaaaat cgatgctcaa    6660
gtcagaggtg gcgaaacccg acaggactat aaagatacca ggcgtttccc cctggaagct    6720
ccctcgtgcg ctctcctgtt ccgaccctgc cgcttaccgg atacctgtcc gcctttctcc    6780
cttcgggaag cgtggcgctt tctcatagct cacgctgtag gtatctcagt tcggtgtagg    6840
tcgttcgctc caagctgggc tgtgtgcacg aaccccccgt tcagcccgac cgctgcgcct    6900
tatccggtaa ctatcgtctt gagtccaacc cggtaagaca cgacttatcg ccactggcag    6960
cagccactgg taacaggatt agcagagcga ggtatgtagg cggtgctaca gagttcttga    7020
agtggtggcc taactacggc tacactagaa gaacagtatt tggtatctgc gctctgctga    7080
agccagttac cttcggaaaa agagttggta gctcttgatc cggcaaacaa accaccgctg    7140
gtagcggtgg tttttttgtt tgcaagcagc agattacgcg cagaaaaaaa ggatctcaag    7200
aagatccttt gatcttttct acggggtctg acgctcagtg gaacgaaaac tcacgttaag    7260
ggattttggt catgagatta tcaaaaagga tcttcaccta gatccttta aattaaaaat    7320
gaagttttaa atcaatctaa agtatatatg agtaaacttg gtctgacagt taccaatgct    7380
taatcagtga ggcacctatc tcagcgatct gtctatttcg ttcatccata gttgcctgac    7440
tccccgtcgt gtagataact acgatacggg agggcttacc atctggcccc agtgctgcaa    7500
tgataccgcg agacccacgc tcaccggctc cagatttatc agcaataaac cagccagccg    7560
gaagggccga gcgcagaagt ggtcctgcaa ctttatccgc ctccatccag tctattaatt    7620
gttgccggga agctagagta agtagttcgc cagttaatag tttgcgcaac gttgttgcca    7680
ttgctacagg catcgtggtg tcacgctcgt cgtttggtat ggcttcattc agctccggtt    7740
cccaacgatc aaggcgagtt acatgatccc ccatgttgtg caaaaaagcg gttagctcct    7800
tcggtcctcc gatcgttgtc agaagtaagt tggccgcagt gttatcactc atggttatgg    7860
cagcactgca taattctctt actgtcatgc catccgtaag atgcttttct gtgactggtg    7920
agtactcaac caagtcattc tgagaatagt gtatgcggcg accgagttgc tcttgcccgg    7980
cgtcaatacg ggataatacc gcgccacata gcagaacttt aaaagtgctc atcattggaa    8040
aacgttcttc ggggcgaaaa ctctcaagga tcttaccgct gttgagatcc agttcgatgt    8100
aacccactcg tgcacccaac tgatcttcag catcttttac tttcaccagc gtttctgggt    8160
gagcaaaaac aggaaggcaa aatgccgcaa aaagggaat aagggcgaca cggaaatgtt    8220
gaatactcat actcttcctt tttcaatatt attgaagcat ttatcagggt tattgtctca    8280
tgagcggata catatttgaa tgtatttaga aaataaaca aatagggggtt ccgcgcacat    8340
ttccccga                                                            8348
```

<210> SEQ ID NO 50

```
<211> LENGTH: 8233
<212> TYPE: DNA
<213> ORGANISM: Artificial Sequence
<220> FEATURE:
<223> OTHER INFORMATION: Ovalbumin gene OV Construct 4 hCECR1

<400> SEQUENCE: 50
```

| | | | | | |
|---|---|---|---|---|---|
| aaagtgccac | ctgacgtcga | cggttatcca | cagaatcagg | ggataacgca | ggaaagaaca | 60 |
| tgtgcgcatg | cctgctattg | tcttcccaat | cctccccctt | gctgtcctgc | ccacccccac | 120 |
| cccccagaat | agaatgacac | ctactcagac | aatgcgatgc | aatttcctca | ttttattagg | 180 |
| aaaggacagt | gggagtggca | ccttccaggg | tcaaggaagg | cacggggggag | gggcaaacaa | 240 |
| cagatggctg | gcaactagaa | ggcacagtcg | aggctgatca | gcgagctcta | gcatttaggt | 300 |
| gacactatag | aatagggccc | tctagcgaat | taattcaggt | tgttaacaac | aacaattttc | 360 |
| gaaggtacct | caggcaccgg | gcttgcgggt | catgcaccag | gtgcgcggtc | cttcgggcac | 420 |
| ctcgacgtcg | gcggtgacgg | tgaagccgag | ccgctcgtag | aagggggaggt | tgcggggcgc | 480 |
| ggaggtctcc | aggaaggcgg | gcaccccggc | gcgctcggcc | gcctccactc | cggggagcac | 540 |
| gacggcgctg | cccagaccct | tgccctggtg | gtcgggcgag | acgccgacgg | tggccaggaa | 600 |
| ccacgcgggc | tccttgggcc | ggtgcggcgc | caggaggcct | tccatctgtt | gctgcgcggc | 660 |
| cagccgggaa | ccgctcaact | cggccatgcg | cgggccgatc | tcggcgaaca | ccgcccccgc | 720 |
| ttcgacgctc | tccggcgtgg | tccagaccgc | caccgcggcg | ccgtcgtccg | cgacccacac | 780 |
| cttgccgatg | tcgagcccga | cgcgcgtgag | gaagagttct | tgcagctcgg | tgacccgctc | 840 |
| gatgtgcggg | tccgggtcga | cggtgtggcg | cgtggcgggg | tagtcggcga | acgcggcggc | 900 |
| gagggtgcgt | acggcccggg | ggacgtcgtc | gcgggtggcg | aggcgcaccg | tgggcttgta | 960 |
| ctcggtcatg | gtaccagctt | tttgcaaaag | cctaggcctc | caaaaaagcc | tcctcactac | 1020 |
| ttctggaata | gctcagaggc | agaggcggcc | tcggcctctg | cataaataaa | aaaaattagt | 1080 |
| cagccatggg | gcgagaatg | gcggaactg | ggcggagtta | ggggcgggat | gggcggagtt | 1140 |
| aggggcggga | ctatggttgc | tgactaattg | agatgcatgc | tttgcatact | tctgcctgct | 1200 |
| ggggagcctg | gggactttcc | acacctggtt | gctgactaat | tgagatgcat | gctttgcata | 1260 |
| cttctgcctg | ctggggagcc | tggggacttt | ccacacccta | actgacacac | attccacaga | 1320 |
| catgtgagca | aaaggccagc | aaaaggacta | gttattgtaa | taaatgagaa | ttcattgaaa | 1380 |
| tgttagtatg | ctaactcaat | ctaaattata | aagataaaga | ggcatttaat | cacagctaga | 1440 |
| tttccatcac | ttgtgacaga | caggcatatg | aatgattatg | tacagctcta | ggaaaaaaag | 1500 |
| tatgtaggaa | aactagtaca | ttttgattag | aaagtctgaa | aatgaggtgc | cttgatccaa | 1560 |
| gagaatacgt | gtgtttgaga | aaaaaaaagt | ttggatagag | gtggtaagag | agaatatatt | 1620 |
| gaaatggtgt | ttctacaaac | tgccatggcc | agatttgtgt | aagagacatt | cagtaagtag | 1680 |
| gcaaggaaag | aaatattact | aggtacaaag | caacattagt | aataccaaaa | gaaaccaatt | 1740 |
| attccagatg | ccaatctcgt | aatagggtta | agagatttcc | accctctag | tggtcaccag | 1800 |
| tgcaaccagt | aactttgcta | atttacattt | tcttttttta | aatggcagat | atagctttga | 1860 |
| actgagtgat | catgaactgg | tactgtgtaa | ataagatgga | agcatacttg | gcagctaaac | 1920 |
| ttctagtttt | taaaaactca | aattctcttg | aaagatcagt | tcccagtcta | gtaacagctg | 1980 |
| atagtttaag | tatcagtaat | tggctaccat | taacaactgg | ctcctgagag | gtcttaaatg | 2040 |
| tagagacagc | tttaaactca | aaagcacaga | gtgattttta | gaatagactt | cccaagcaaa | 2100 |
| gaaaataaac | agggaggagc | tttaagggag | tagccatctc | attattatta | ttatttaaag | 2160 |

```
aaatggcagc aagcctacaa agaaaaaata agacagagca gagaagaaag agtcatggta    2220
tgcttttcta tcttagcaaa attaatctct acatgcctag gaaaaagcca tgacaagagc    2280
aatcagttca aaaggtgtat gcaaaaaacc acataatagt aactagtact gcattgccag    2340
gaaggaagtt atgtcgccat tccatggatc tcattctcat ttccttgcag cttgagagta    2400
taatcaactt tgaaaaactg actgaatgga ccagttctaa tgttatggaa gagaggaaga    2460
tcaaagtgta cttacctcgc atgaagatgg aggaaaaata caacctcaca tctgtcttaa    2520
tggctatggg cattactgac gtgtttagct cttcagccaa tctgtctggc atctcctcag    2580
cagagagcct gaagatatct caagctgtcc atgcagcaca tgcagaaatc aatgaagcag    2640
gcagagaggt ggtagggtca gcagaggctg gagtggatgc tgcaagcgtc tctgaagaat    2700
ttagggctga ccatccattc ctcttctgta tcaagcacat cgcaaccaac gccgttctct    2760
tctttggcag atgtgtttcc ccttaaaaag aagaaagctg aaaaacgccg ccctctcccc    2820
tccccccccc ctaacgttac tggccgaagc cgcttggaat aaggccggtg tgcgtttgtc    2880
tatatgttat tttccaccat attgccgtct tttggcaatg tgagggcccg gaaacctggc    2940
cctgtcttct tgacgagcat cctaggggg  ctttcccctc tcgccaaagg aatgcaaggt    3000
ctgttgaatg tcgtgaagga agcagttcct ctggaagctt cttgaagaca acaacgtct    3060 gtagcgaccc tttgcaggca gcggaacccc ccacctggcg acaggtgcct ctgcggccaa    3120
aagccacgtg tataagatac acctgcaaag gcggcacaac cccagtgcca cgttgtgagt    3180
tggatagttg tggaaagagt caaatggctc tcctcaagcg tattcaacaa ggggctgaag    3240
gatgcccaga aggtacccca ttgtatggga tctgatctgg ggcctcggta cacatgcttt    3300
acatgtgttt agtcgaggtt aaaaaaacgt ctaggccccc cgaaccacgg ggacgtggtt    3360
ttcctttgaa aaacacgatg ataatatggc cacagccacc atgttggtgg atggcccatc    3420
tgagcggcca gccctgtgct tcttgctgtt ggctgtggca atgtctttct tcggctctgc    3480
tctatccata gatgaaacac gggcgcatct gttgttgaaa gaaaagatga tgcggctggg    3540
ggggcggctg gtgctgaaca ccaaggagga gctggccaat gagaggctca tgacgctcaa    3600
aatcgctgag atgaaggagg ccatgaggac cctgatattc ccacccagca tgcactttt    3660 ccaggccaag catctcattg agagaagtca agtgtttaat attctaagga tgatgccaaa    3720
aggggctgcc ttgcacctcc atgacattgg catcgtgact atggactggc tggtgaggaa    3780
tgtcacctac aggcctcact gccacatctg tttcacccca aggggggatca tgcagttcag    3840 atttgctcac ccaactcccc gtccatcaga aaaatgttcc aagtggattc tgctggagga    3900
ttatcggaag cgggtgcaga acgtcactga gtttgatgac agcttgctga ggaatttcac    3960
tctggtgacc cagcacccgg aggtgattta cacaaaccaa aatgttgtct ggtcgaaatt    4020
tgaaaccatc ttcttcacca tctctggtct catccattac gctccagtgt tcagagacta    4080
tgtcttccgg agcatgcagg agttctacga ggacaacgtg ctctacatgg agatcagagc    4140
caggctgctg ccggtgtatg agctcagtgg agagcaccat gacgaagagt ggtcagtgaa    4200
gacttatcag gaagtagctc agaagtttgt ggaaactcat cctgagttta ttggaatcaa    4260 aatcattat  tcggatcaca gatccaaaga tgtggctgtc atcgcagaat ccatccgaat    4320
ggccatgggg ctccgaatca gttccccac ggtggtggca gggtttgacc tggtggggca    4380
tgaggacact ggccactcct tgcatgacta caaggaagct ctgatgatcc ccgccaagga    4440
tggcgttaag ctgcccttact tcttccacgc cggagaaaca gactggcagg gtacttccat    4500
```

```
agacaggaac attctggatg ctctgatgct gaacactacc agaatcggcc atggatttgc    4560
tttgagcaaa caccccgcag tcaggactta ttcctggaaa aaggacatcc ccatagaagt    4620
ctgtcccatc tctaaccagg tgctgaaact ggtgtctgac ttgaggaacc accctgtagc    4680
cactctgatg gccactgggc accccatggt gatcagctct gatgacccag ctatgtttgg    4740
tgccaaaggc ttgtcctatg atttctatga ggtcttcatg ggcattgggg ggatgaaggc    4800
tgatctgagg accctcaaac agctggccat gaactctatc aagtacagta ccctgttgga    4860
gagtgagaaa aatactttca tggaaatatg gaagaagaga tgggataagt tcatagcaga    4920
tgtggctaca aagtgatctg tcccttccaa caagacccag agcactgtag tatcaggggt    4980
aaaatgaaaa gtatgttatc tgctgcatcc agacttcata aaagctggag cttaatctag    5040
aaaaaaaatc agaaagaaat tacactgtga gaacaggtgc aattcacttt tcctttacac    5100
agagtaatac tggtaactca tggatgaagg cttaagggaa tgaaattgga ctcacagtac    5160
tgagtcatca cactgaaaaa tgcaacctga tacatcagca gaaggtttat gggggaaaaa    5220
tgcagccttc caattaagcc agatatctgt atgaccaagc tgctccagaa ttagtcactc    5280
aaaatctctc agattaaatt atcaactgtc accaaccatt cctatgctga caaggcaatt    5340
gcttgttctc tgtgttcctg atactacaag gctcttcctg acttcctaaa gatgcattat    5400
aaaaatctta taattcacat ttctccctaa actttgactc aatcatggta tgttggcaaa    5460
tatggtatat tactattcaa attgttttcc ttgtacccat atgtaatggg tcttgtgaat    5520
gtgctctttt gttcctttaa tcataataaa acatgtttta agcaaacact tttcacttgt    5580
agtatttgaa gtacagcaag gttgtgtagc agggaaagaa tgacatgcag aggaataagt    5640
atggacacac aggctagcag cgactgtaga acaagtacta atgggtgaga agttgaacaa    5700
gagtccccta cagcaactta atctaataag ctagtggtct acatcagcta aaagagcata    5760
gtgagggatg aaattggttc tcctttctaa gcatcacctg gacaactca tctggagcag    5820 tgtgtccaat ctgccgctgc cctgatcctg gctggggtga tgggacagac cttggctgcc    5880
actgagacat ctgagacact gagatctgtc tcaactcaga tttacccaag aacagatcat    5940
tgccaacaga acaaaatctc aaacttatgg ctagtgatga cagcagtcag ttgtcccatc    6000
tgtgacccac caaggctggc atgctggaat gagcaggctt tggtggcttg tagttactgg    6060
acagcaccac tgcatggggc aggggaaaaa ctgagcatgg tgtaaatcac tgcctcaaag    6120
ccacttctct gtgcctgcac catgcttgaa agctcttcta caggagctgg gtttgttcaa    6180
gaaagcttct gtttctccca tctgcttctt gtaccttcac agggacagag ttagaagggt    6240
acagccatgg tcgtgccagc tgcattaatg aatcggccaa cgcgcgggga gaggcggttt    6300
gcgtattggg cgctcttccg cttcctcgct cactgactcg ctgcgctcgg tcgttcggct    6360
gcggcgagcg gtatcagctc actcaaaggc ggtaatacgg ttatccacag aatcagggga    6420
taacgcagga aagaacatgt gagcaaaagg ccagcaaaag gccaggaacc gtaaaaaggc    6480
cgcgttgctg gcgttttttcc ataggctccg ccccctgac gagcatcaca aaaatcgatg    6540
ctcaagtcag aggtggcgaa acccgacagg actataaaga taccaggcgt ttccccctgg    6600
aagctccctc gtgcgctctc ctgttccgac cctgccgctt accggatacc tgtccgcctt    6660
tctcccttcg ggaagcgtgg cgctttctca tagctcacgc tgtaggtatc tcagttcggt    6720
gtaggtcgtt cgctccaagc tgggctgtgt gcacgaaccc cccgttcagc ccgaccgctg    6780
cgccttatcc ggtaactatc gtcttgagtc aacccggta agacacgact tatcgccact    6840
ggcagcagcc actggtaaca ggattagcag agcgaggtat gtaggcggtg ctacagagtt    6900
```

-continued

```
cttgaagtgg tggcctaact acggctacac tagaagaaca gtatttggta tctgcgctct   6960
gctgaagcca gttaccttcg gaaaaagagt tggtagctct tgatccggca aacaaaccac   7020
cgctggtagc ggtggttttt ttgtttgcaa gcagcagatt acgcgcagaa aaaaaggatc   7080
tcaagaagat cctttgatct tttctacggg gtctgacgct cagtggaacg aaaactcacg   7140
ttaagggatt ttggtcatga gattatcaaa aaggatcttc acctagatcc ttttaaatta   7200
aaaatgaagt tttaaatcaa tctaaagtat atatgagtaa acttggtctg acagttacca   7260
atgcttaatc agtgaggcac ctatctcagc gatctgtcta tttcgttcat ccatagttgc   7320
ctgactcccc gtcgtgtaga taactacgat acgggagggc ttaccatctg gccccagtgc   7380
tgcaatgata ccgcgagacc cacgctcacc ggctccagat ttatcagcaa taaaccagcc   7440
agccggaagg gccgagcgca gaagtggtcc tgcaacttta tccgcctcca tccagtctat   7500
taattgttgc cgggaagcta gagtaagtag ttcgccagtt aatagtttgc gcaacgttgt   7560
tgccattgct acaggcatcg tggtgtcacg ctcgtcgttt ggtatggctt cattcagctc   7620
cggttcccaa cgatcaaggc gagttacatg atcccccatg ttgtgcaaaa aagcggttag   7680
ctccttcggt cctccgatcg ttgtcagaag taagttggcc gcagtgttat cactcatggt   7740
tatggcagca ctgcataatt ctcttactgt catgccatcc gtaagatgct tttctgtgac   7800
tggtgagtac tcaaccaagt cattctgaga atagtgtatg cggcgaccga gttgctcttg   7860
cccggcgtca atacgggata ataccgcgcc acatagcaga actttaaaag tgctcatcat   7920
tggaaaacgt tcttcggggc gaaaactctc aaggatctta ccgctgttga gatccagttc   7980
gatgtaaccc actcgtgcac ccaactgatc ttcagcatct tttactttca ccagcgtttc   8040
tgggtgagca aaaacaggaa ggcaaaatgc cgcaaaaaag ggaataaggg cgacacggaa   8100
atgttgaata ctcatactct tcctttttca atattattga agcatttatc agggttattg   8160
tctcatgagc ggatacatat ttgaatgtat ttagaaaaat aaacaaatag gggttccgcg   8220
cacatttccc cga                                                     8233
```

<210> SEQ ID NO 51
<211> LENGTH: 6472
<212> TYPE: DNA
<213> ORGANISM: Artificial Sequence
<220> FEATURE:
<223> OTHER INFORMATION: Construct 5 Hc-P2A-Lc-P2A-OVAL

<400> SEQUENCE: 51

```
aaagtgccac ctgacgtcga cggttatcca cagaatcagg ggataacgca ggaaagaaca     60
tgtgcgcatg cctgctattg tcttcccaat cctcccccct tgctgtcctg cccacccccac    120
cccccagaat agaatgacac ctactcagac aatgcgatgc aatttcctca ttttattagg    180
aaaggacagt gggagtggca ccttccaggg tcaaggaagg cacggggagg ggcaaacaa     240
cagatggctg gcaactagaa ggcacagtcg aggctgatca gcgagctcta gcatttaggt    300
gacactatag aatagggccc tctagcgaat taattcaggt tgttaacaac aacaattttc    360
gaaggtacct caggcaccgg gcttgcgggt catgcaccag gtgcgcggtc cttcgggcac    420
ctcgacgtcg gcggtgacgg tgaagccgag ccgctcgtag aagggaggt tgcggggcgc    480
ggaggtctcc aggaaggcgg gcaccccggc gcgctcggcc gcctccactc cggggagcac    540
gacgcgctg cccagaccct tgccctggtg gtcgggcgag acgccgacgg tggccaggaa     600
ccacgcgggc tccttgggcc ggtgcggcgc caggaggcct tccatctgtt gctgcgcggc    660
```

```
cagccgggaa ccgctcaact cggccatgcg cgggccgatc tcggcgaaca ccgcccccgc    720
ttcgacgctc tccggcgtgg tccagaccgc caccgcggcg ccgtcgtccg cgacccacac    780
cttgccgatg tcgagcccga cgcgcgtgag gaagagttct tgcagctcgg tgacccgctc    840
gatgtggcgg tccgggtcga cggtgtggcg cgtggcgggg tagtcggcga acgcggcggc    900
gagggtgcgt acggcccggg ggacgtcgtc gcgggtggcg aggcgcaccg tgggcttgta    960
ctcggtcatg gtaccagctt tttgcaaaag cctaggcctc aaaaaagcc tcctcactac    1020 ttctggaata gctcagaggc agaggcggcc tcggcctctg cataaataaa aaaaattagt    1080
cagccatggg gcgagaatg gcggaactg gcggagtta ggggcgggat gggcggagtt    1140
aggggcggga ctatggttgc tgactaattg agatgcatgc tttgcatact tctgcctgct    1200
ggggagcctg gggactttcc acacctggtt gctgactaat tgagatgcat gctttgcata    1260
cttctgcctg ctggggagcc tggggacttt ccacacccta actgacacac attccacaga    1320
catgtgagca aaaggccagc aaaaggacta gttattgata tcagtacctg cgtgataccc    1380
cctataaaaa cttctcacct gtgtatgcat tctgcactat tttattatgt gtaaaagctt    1440
tgtgtttgtt ttcaggaggc ttattctttg tgcttaaaat atgttttaa tttcagaaca    1500 tcttatcctg tcgttcacta tctgatatgc tttgcagttt gcttgattaa cttctagccc    1560
tacagagtgc acagagagca aaatcatggt gttcagtgaa ttctggggag ttatttttaat   1620 gtgaaaattc tctagaagtt taattcctgc aaagtgcagc tgctgatcac tacacaagat    1680
aaaaatgtgg ggggtgcata aacgtatatt cttacaataa tagatacatg tgaacttgta    1740
tacagaaaag aaaatgagaa aatgtgtgt gcgtatactc acacacgtgg tcagtaaaaa    1800
cttttgaggg gtttaataca gaaaatccaa tcctgaggcc ccagcactca gtacgcatat    1860
aaagggctgg gctctgaagg acttctgact ttcacagatt atataaatct caggaaagca    1920
actagattca tgctggctcc aaaagctgtg ctttatataa gcacactggc tatacaatag    1980
ttgtacagtt cagctcttta taatagaaac agacagaaca agtataaatc ttctattggt    2040
ctatgtcatg aacaagaatt cattcagtgg ctctgtttta tagtaaacat tgctattta    2100 tcatgtctgc atttctcttc tgtctgaatg tcaccactaa aatttaactc cacagaaagt    2160
ttatactaca gtacacatgc atatctttga gcaaagcaaa ccatacctga agtgcaata    2220 gagcagaata tgaattacat gcgtgtcttt ctcctagact acatgacccc atataaatta    2280
cattccttat ctattctgcc atcaccaaaa caaaggtaaa aatacttttg aagatctact    2340
catagcaagt agtgtgcaac aaacagatat ttctctacat ttatttttag ggaataaaaa    2400
taagaaataa aatagtcagc aagcctctgc tttctcatat atctgtccaa acctaaagtt    2460
tactgaaatt tgctctttga atttccagtt ttgcaagcct atcagattgt gttttaatca    2520
gaggtactga aaagtatcaa tgaattctag cttttcactga acaaaaatat gtagaggcaa    2580
ctggcttctg ggacagtttg ctacccaaaa gacaactgaa tgcaaataca taaatagatt    2640
tatgaatatg gttttgaaca tgcacatgag aggtggatat agcaacagac acattaccac    2700
agaattactt taaaactact tgttaacatt taattgccta aaaactgctc gtaatttact    2760
gttgtagcct accatagagt accctgcatg gtactatgta cagcattcca tccttacatt    2820
ttcactgttc tgctgtttgc tctagacaac tcagagttca ccggaagcgg agctactaac    2880
ttcagcctgc tgaagcaggc tggagacgtg gaggagaacc ctggacctgg aagcggagct    2940
actaacttca gcctgctgaa gcaggctgga gacgtggagg agaaccctgg acctatgggc    3000
tccatcggtg cagcaagcat ggaattttgt tttgatgtat tcaaggagct caaagtccac    3060
```

```
catgccaatg agaacatctt ctactgcccc attgccatca tgtcagctct agccatggta    3120
tacctgggtg caaaagacag caccaggaca caaataaata aggtgagcct acagttaaag    3180
attaaaacct ttgccctgct caatggagcc acagcactta attgtatgat aatgtccctt    3240
ggaaactgca tagctcagag gctgaaaatc tgaaaccaga gttatctaaa agtgtggcca    3300
cctccaactc ccagagtgtt acccaaatgc actagctaga aatcttgaaa ctggattgca    3360
taacttcttt ttgtcataac cattatttca gctactatta ttttcaatta caggttgttc    3420
gctttgataa acttccagga ttcggagaca gtattgaagc tcaggtacag aaataatttc    3480
acctccttct ctatgtccct ttcctctgga agcaaaatac agcagatgaa gcaatctctt    3540
agctgttcca agccctctct gatgagcagc tagtgctctg catccagcag ttgggagaac    3600
actgttcata agaacagaga aaagaagga agtaacaggg gattcagaac aaacagaaga    3660
taaaactcag gacaaaaata ccgtgtgaat gaggaaactt gtggatattt gtacgcttaa    3720
gcaagacagc tagatgattc tggataaatg ggtctggttg gaaagaagg aaagcctggc    3780 tgatctgctg gagctagatt attgcagcag gtaggcagga gttccctaga gaaaagtatg    3840
agggaattac agaagaaaaa cagcacaaaa ttgtaaatat tggaaaagga ccacatcagt    3900
gtagttacta gcagtaagac agacaggatg aaaaatagtt ttgtaaacag aagtatctaa    3960
ctactttact ctgttcatac actacgtaaa acctactaag taataaaact agaataacaa    4020
catctttctt tctctttgta ttcagtgtgg cacatctgta aacgttcact cttcacttag    4080
agacatcctc aaccaaatca ccaaaccaaa tgatgtttat tcgttcagcc ttgccagtag    4140
actttatgct gaagagagat acccaatcct gccagtaagt tgctctaaaa tctgatctga    4200
gtgtatttcc atgccaaagc tctaccattc tgtaatgcaa aaacagtcag agttccacat    4260
gtttcactaa gaaaatttct ttttctcttg tttttacaaa tgaaagagag gacaaataac    4320
atttctctat caccgacctg aaactctaca gtcttcagag aatgaatggc ttgctaaaag    4380
aatgtcaaat cttaccatac agctatttca tattcacacta ctaaatacac tataaggcat    4440
agcatgtagt aatacagtgt aaaatagctt tttacactac tagatatcgt cgtgccagct    4500
gcattaatga atcggccaac gcgcggggag aggcggtttg cgtattgggc gctcttccgc    4560
ttcctcgctc actgactcgc tgcgctcggt cgttcggctg cggcgagcgg tatcagctca    4620
ctcaaaggcg gtaatacggt tatccacaga atcagggga aacgcaggaa agaacatgtg    4680
agcaaaaggc cagcaaaagg ccaggaaccg taaaaaggcc gcgttgctgg cgttttttcca    4740 taggctccgc ccccctgacg agcatcacaa aaatcgatgc tcaagtcaga ggtggcgaaa    4800
cccgacagga ctataaagat accaggcgtt tccccctgga agctccctcg tgcgctctcc    4860
tgttccgacc ctgccgctta ccggatacct gtccgccttt ctcccttcgg gaagcgtggc    4920
gctttctcat agctcacgct gtaggtatct cagttcggtg taggtcgttc gctccaagct    4980
gggctgtgtg cacgaacccc ccgttcagcc cgaccgctgc gccttatccg gtaactatcg    5040
tcttgagtcc aacccggtaa gacacgactt atcgccactg gcagcagcca ctggtaacag    5100
gattagcaga gcgaggtatg taggcggtgc tacagagttc ttgaagtggt ggcctaacta    5160
cggctacact agaagaacag tatttggtat ctgcgctctg ctgaagccag ttaccttcgg    5220
aaaaagagtt ggtagctctt gatccggcaa acaaaccacc gctggtagcg gtggtttttt    5280
tgtttgcaag cagcagatta cgcgcagaaa aaaaggatct caagaagatc ctttgatctt    5340
ttctacgggg tctgacgctc agtggaacga aaactcacgt taaggatttt ggtcatgag    5400
```

```
attatcaaaa aggatcttca cctagatcct tttaaattaa aaatgaagtt ttaaatcaat    5460
ctaaagtata tatgagtaaa cttggtctga cagttaccaa tgcttaatca gtgaggcacc    5520
tatctcagcg atctgtctat ttcgttcatc catagttgcc tgactccccg tcgtgtagat    5580
aactacgata cgggagggct taccatctgg ccccagtgct gcaatgatac cgcgagaccc    5640
acgctcaccg gctccagatt tatcagcaat aaaccagcca gccggaaggg ccgagcgcag    5700
aagtggtcct gcaactttat ccgcctccat ccagtctatt aattgttgcc gggaagctag    5760
agtaagtagt tcgccagtta atagtttgcg caacgttgtt gccattgcta caggcatcgt    5820
ggtgtcacgc tcgtcgtttg gtatggcttc attcagctcc ggttcccaac gatcaaggcg    5880
agttacatga tcccccatgt tgtgcaaaaa agcggttagc tccttcggtc ctccgatcgt    5940
tgtcagaagt aagttggccg cagtgttatc actcatggtt atggcagcac tgcataattc    6000
tcttactgtc atgccatccg taagatgctt ttctgtgact ggtgagtact caaccaagtc    6060
attctgagaa tagtgtatgc ggcgaccgag ttgctcttgc ccggcgtcaa tacgggataa    6120
taccgcgcca catagcagaa ctttaaaagt gctcatcatt ggaaaacgtt cttcggggcg    6180
aaaactctca aggatcttac cgctgttgag atccagttcg atgtaaccca ctcgtgcacc    6240
caactgatct tcagcatctt ttactttcac cagcgtttct gggtgagcaa aaacaggaag    6300
gcaaaatgcc gcaaaaaagg gaataagggc gacacggaaa tgttgaatac tcatactctt    6360
cctttttcaa tattattgaa gcatttatca gggttattgt ctcatgagcg gatacatatt    6420
tgaatgtatt tagaaaaata aacaaatagg ggttccgcgc acatttcccc ga           6472

<210> SEQ ID NO 52
<211> LENGTH: 6232
<212> TYPE: DNA
<213> ORGANISM: Artificial Sequence
<220> FEATURE:
<223> OTHER INFORMATION: Construct 6 OVAL-P2A -Hc-P2A-Lc

<400> SEQUENCE: 52
aaagtgccac ctgacgtcga cggttatcca cagaatcagg ggataacgca ggaaagaaca      60
tgtgcgcatg cctgctattg tcttcccaat cctcccccct tgctgtcctg cccacccccac    120
cccccagaat agaatgacac ctactcagac aatgcgatgc aatttcctca ttttattagg    180
aaaggacagt gggagtggca ccttccaggg tcaaggaagg cacggggagg ggcaaacaa     240
cagatggctg gcaactagaa ggcacagtcg aggctgatca gcgagctcta gcatttaggt    300
gacactatag aatagggccc tctagcgaat taattcaggt tgttaacaac aacaattttc    360
gaaggtacct caggcaccgg gcttgcgggt catgcaccag gtgcgcggtc cttcgggcac    420
ctcgacgtcg gcggtgacgg tgaagccgag ccgctcgtag aagggggaggt tgcggggcgc    480
ggaggtctcc aggaaggcgg gcaccccggc gcgctcggcc gcctccactc cggggagcac    540
gacggcgctg cccagaccct tgccctggtg gtcgggcgag acgccgacgg tggccaggaa    600
ccacgcgggc tccttgggcc ggtgcggcgc caggaggcct tccatctgtt gctgcgcggc    660
cagccgggaa ccgctcaact cggccatgcg cgggccgatc tcggcgaaca ccgcccccgc    720
ttcgacgctc tccggcgtgg tccagaccgc caccgcggcg ccgtcgtccg cgacccacac    780
cttgccgatg tcgagcccga cgcgcgtgag gaagagttct gcagctcgg tgaccgctc    840
gatgtggcgt tccgggtcga cggtgtggcg cgtggcgggg tagtcggcga acgcggcggc    900
gagggtgcgt acgccggg ggacgtcgtc gcggtggcgg aggcgcaccg tgggcttgta    960
ctcggtcatg gtaccagctt tttgcaaaag cctaggcctc caaaaaagcc tcctcactac   1020
```

-continued

```
ttctggaata gctcagaggc agaggcggcc tcggcctctg cataaataaa aaaaattagt    1080
cagccatggg gcggagaatg ggcggaactg ggcggagtta ggggcgggat gggcggagtt    1140
aggggcggga ctatggttgc tgactaattg agatgcatgc tttgcatact tctgcctgct    1200
ggggagcctg gggactttcc acacctggtt gctgactaat tgagatgcat gctttgcata    1260
cttctgcctg ctggggagcc tggggacttt ccacaccta actgacacac attccacaga    1320
catgtgagca aaaggccagc aaaaggacta gttattataa atgagaattc attgaaatgt    1380
tagtatgcta actcaatcta aattataaag ataaagaggc atttaatcac agctagattt    1440
ccatcacttg tgacagacag gcatatgaat gattatgtac agctctagga aaaaagtat    1500 gtaggaaaac tagtacattt tgattagaaa gtctgaaaat gaggtgcctt gatccaagag    1560
aatacgtgtg tttgagaaaa aaaaagtttg gatagaggtg gtaagagaga atatattgaa    1620
atggtgtttc tacaaactgc catggccaga tttgtgtaag agacattcag taagtaggca    1680
aggaaagaaa tattactagg tacaaagcaa cattagtaat accaaaagaa accaattatt    1740
ccagatgcca atctcgtaat agggttaaga gatttccacc cctctagtgg tcaccagtgc    1800
aaccagtaac tttgctaatt tacatttct tttttttaaat ggcagatata gctttgaact    1860
gagtgatcat gaactggtac tgtgtaaata agatggaagc atacttggca gctaaacttc    1920
tagtttttaa aaactcaaat tctcttgaaa gatcagttcc cagtctagta acagctgata    1980
gtttaagtat cagtaattgg ctaccattaa caactggctc ctgagaggtc ttaaatgtag    2040
agacagcttt aaactcaaaa gcacagagtg attttttagaa tagacttccc aagcaaagaa    2100
aataaacagg gaggagcttt aagggagtag ccatctcatt attattatta tttaaagaaa    2160
tggcagcaag cctacaaaag aaaaataaga cagagcagag aagaaagagt catggtatgc    2220
ttttctatct tagcaaaatt aatctctaca tgcctaggaa aaagccatga caagagcaat    2280
cagttcaaaa ggtgtatgca aaaaaccaca taatagtaac tagtactgca ttgccaggaa    2340
ggaagttatg tcgccattcc atggatctca ttctcatttc cttgcagctt gagagtataa    2400
tcaactttga aaaactgact gaatggacca gttctaatgt tatggaagag aggaagatca    2460
aagtgtactt acctcgcatg aagatggagg aaaaatacaa cctcacatct gtcttaatgg    2520
ctatgggcat tactgacgtg tttagctctt cagccaatct gtctggcatc tcctcagcag    2580
agagcctgaa gatatctcaa gctgtccatg cagcacatga agaaatcaat gaagcaggca    2640
gagaggtggt agggtcagca gaggctggag tggatgctgc aagcgtctct gaagaattta    2700
gggctgacca tccattcctc ttctgtatca agcacatcgc aaccaacgcc gttctcttct    2760
ttggcagatg tgtttcccct ggaagcggag ctactaactt cagcctgctg aagcaggctg    2820
gagacgtgga ggagaaccct ggacctgaa gcggagctac taacttcagc ctgctgaagc    2880
aggctggaga cgtggaggag aaccctggac cttaaaaaga gaaagctga aaaactctgt    2940 cccttccaac aagacccaga gcactgtagt atcaggggta aatgaaaag tatgttctct    3000 gctgcatcca gacttcataa agctggagc ttaatctaga aaaaaatca gaaagaaatt    3060 acactgtgag aacaggtgca attcactttt cctttacaca gagtaatact ggtaactcat    3120
ggatgaaggc ttaagggaat gaaattggac tcacagtact gagtcatcac actgaaaaat    3180
gcaacctgat acatcagcag aaggtttatg ggggaaaaat gcagccttcc aattaagcca    3240
gatatctgta tgaccaagct cctccagaat tagtcactca aaatctctca gattaaatta    3300
tcaactgtca ccaactattc ctatgctgac aaggcaattg cttgttctct gtgttcctga    3360
```

```
tactacaagg ctcttcctga cttcctaaag atgcattata aaaatcttat aattcacatt    3420
tctccctaaa ctttgactca atcatggtat gttggcaaat atggtatatt actattcaaa    3480
ttgttttcct tgtacccata tgtaatgggt cttgtgaatg tgctcttttg ttcctttaat    3540
cataataaaa acatgtttaa gcaaacactt tcacttgta gtatttgaag tacagcaagg     3600
ttgtgtagca gggaaagaat gacatgcaga ggaataagta tggacacaca ggctagcagc    3660
gactgtagaa caagtactaa tgggtgagaa gttgaacaag agtccctac agcaacttaa     3720 tctaataagc tagtggtcta catcagctaa aagagcatag tgagggatga aattgattct    3780
cctttctaag catcacctgg gacaactcat ctggagcagt gtgtccaatc tgccgctgcc    3840
ctgatcctgg ctggggtgat gggacagacc ttggctgcca ctgagacatc tgagacactg    3900
agatctgtct caactcagat ttacccaaga acagctcatt gccaacagaa caaaatctca    3960
aacttatggc tagtgatgac agcagtcagt tgtcccatct gtgacccacc aaggctggca    4020
tgctggaatg agcaggcttt ggtggcatgt agttactgga cagcaccact gacatgggca    4080
ggggaaaaac tgagcatggt gtaaatcact gcctcaaagc cacttctctg tgcctgcacc    4140
atgcttgaaa gctcttctac aggagctggg tttgttcaag aaagcttctg tttctcccat    4200
ctgcttcttg taccttcaca gggacagagt tagaagggta cagccatggt cgtgccagct    4260
gcattaatga atcggccaac gcgcggggag aggcggtttg cgtattgggc gctcttccgc    4320
ttcctcgctc actgactcgc tgcgctcggt cgttcggctg cggcgagcgg tatcagctca    4380
ctcaaaggcg gtaatacggt tatccacaga atcaggggat aacgcaggaa agaacatgtg    4440
agcaaaaggc cagcaaaagg ccaggaaccg taaaaaggcc gcgttgctgg cgttttccca    4500
taggctccgc cccctgacg agcatcacaa aaatcgatgc tcaagtcaga ggtggcgaaa     4560
cccgacagga ctataaagat accaggcgtt tccccctgga agctccctcg tgcgctctcc    4620
tgttccgacc ctgccgctta ccggatacct gtccgccttt ctcccttcgg aagcgtggc    4680 gctttctcat agctcacgct gtaggtatct cagttcggtg taggtcgttc gctccaagct    4740
gggctgtgtg cacgaacccc cgttcagcc cgaccgctgc gccttatccg gtaactatcg     4800
tcttgagtcc aacccggtaa gacacgactt atcgccactg gcagcagcca ctggtaacag    4860
gattagcaga gcgaggtatg taggcggtgc tacagagttc ttgaagtggt ggcctaacta    4920
cggctacact agaagaacag tatttggtat ctgcgctctg ctgaagccag ttaccttcgg    4980
aaaaagagtt ggtagctctt gatccggcaa acaaaccacc gctggtagcg gtggtttttt    5040
tgtttgcaag cagcagatta cgcgcagaaa aaaaggatct caagaagatc ctttgatctt    5100
ttctacgggg tctgacgctc agtggaacga aaactcacgt taagggattt tggtcatgag    5160
attatcaaaa aggatcttca cctagatcct tttaaattaa aaatgaagtt ttaaatcaat    5220
ctaaagtata tatgagtaaa cttggtctga cagttaccaa tgcttaatca gtgaggcacc    5280
tatctcagcg atctgtctat ttcgttcatc catagttgcc tgactccccg tcgtgtagat    5340
aactacgata cgggagggct taccatctgg ccccagtgct gcaatgatac cgcgagaccc    5400
acgctcaccg gctccagatt tatcagcaat aaaccagcca gccggaaggg ccgagcgcag    5460
aagtggtcct gcaactttat ccgcctccat ccagtctatt aattgttgcc gggaagctag    5520
agtaagtagt tcgccagtta atagtttgcg caacgttgtt gccattgcta caggcatcgt    5580
ggtgtcacgc tcgtcgtttg gtatggcttc attcagctcc ggttcccaac gatcaaggcg    5640
agttacatga tcccccatgt tgtgcaaaaa agcggttagc tccttcggtc ctccgatcgt    5700
tgtcagaagt aagttggccg cagtgttatc actcatggtt atggcagcac tgcataattc    5760
```

```
tcttactgtc atgccatccg taagatgctt ttctgtgact ggtgagtact caaccaagtc    5820
attctgagaa tagtgtatgc ggcgaccgag ttgctcttgc ccggcgtcaa tacgggataa    5880
taccgcgcca catagcagaa cttttaaaagt gctcatcatt ggaaaacgtt cttcggggcg   5940
aaaactctca aggatcttac cgctgttgag atccagttcg atgtaaccca ctcgtgcacc    6000
caactgatct tcagcatctt ttactttcac cagcgtttct gggtgagcaa aacaggaag    6060 gcaaaatgcc gcaaaaaagg gaataagggc gacacggaaa tgttgaatac tcatactctt   6120 ccttttttcaa tattattgaa gcatttatca gggttattgt ctcatgagcg gatacatatt   6180
tgaatgtatt tagaaaaata aacaaatagg ggttccgcgc acatttcccc ga            6232
```

<210> SEQ ID NO 53
<211> LENGTH: 1500
<212> TYPE: DNA
<213> ORGANISM: Gallus gallus

<400> SEQUENCE: 53

```
tcagagttca ccatgggctc catcggtgca gcaagcatgg aattttgttt tgatgtattc      60
aaggagctca agtccacca tgccaatgag aacatcttct actgcccat tgccatcatg      120 tcagctctag ccatggtata cctgggtgca aaagacagca ccaggacaca aataaataag    180
gtgagcctac agttaaagat taaaaccttt gccctgctca atggagccac agcacttaat    240
tgtatgataa tgtcccttgg aaactgcata gctcagaggc tgaaaatctg aaaccagagt    300
tatctaaaag tgtggccacc tccaactccc agagtgttac ccaaatgcac tagctagaaa    360
tcttgaaact ggattgcata acttcttttt gtcataacca ttatttcagc tactattatt    420
ttcaattaca ggttgttcgc tttgataaac ttccaggatt cggagacagt attgaagctc    480
aggtacagaa ataatttcac ctccttctct atgtcccttt cctctggaag caaaatacag    540
cagatgaagc aatctcttag ctgttccaag ccctctctga tgagcagcta gtgctctgca    600
tccagcagtt gggagaacac tgttcataag aacagagaaa agaaggaag taacagggga    660 ttcagaacaa acagaagata aaactcagga caaaaatacc gtgtgaatga ggaaacttgt    720
ggatatttgt acgcttaagc aagacagcta gatgattctg gataaatggg tctggttgga    780
aaagaaggaa agcctggctg atctgctgga gctagattat tgcagcaggt aggcaggagt    840
tccctagaga aaagtatgag ggaattacag aagaaaaaca gcacaaaatt gtaaatattg    900
gaaaaggacc acatcagtgt agttactagc agtaagacag acaggatgaa aaatagtttt    960
gtaaacagaa gtatctaact actttactct gttcatacac tacgtaaaac ctactaagta   1020
ataaaactag aataacaaca tcttctcttc tctttgtatt cagtgtggca catctgtaaa    1080
cgttcactct tcacttagag acatcctcaa ccaaatcacc aaaccaaatg atgtttattc    1140
gttcagcctt gccagtagac tttatgctga agagagatac ccaatcctgc cagtaagttg    1200
ctctaaaatc tgatctgagt gtatttccat gccaaagctc taccattctg taatgcaaaa    1260
acagtcagag ttccacatgt ttcactaaga aaatttcttt ttctcttgtt tttacaaatg    1320
aaagagagga caaataacat ttctctatca ccgacctgaa actctacagt cttcagaaaa    1380
tgaatggctt gctaaaagaa tgtcaaatct taccatacag ctatttcata ttacactact    1440
aaatacacta taaggcatag catgtagtaa tacagtgtaa aatagctttt tacactacta    1500
```

COMPOSITIONS AND METHODS RELATING TO GENOMIC MODIFICATIONS IN AVIAN PRIMORDIAL GERM CELLS

REFERENCE TO RELATED APPLICATION

This application claims priority from U.S. Provisional Patent Application Ser. No. 62/372,600, filed. Aug. 9, 2016, the entire content of which is incorporated herein by reference.

FIELD OF THE INVENTION

The present invention relates to genomic modifications in a bird effective to produce desired exogenous proteins in eggs produced by the bird.

BACKGROUND OF THE INVENTION

There is a continuing need for methods of making proteins using recombinant technology. Methods of producing an exogenous protein in a bird egg are provided by the present invention.

SUMMARY OF THE INVENTION

Methods of producing an exogenous protein in a bird egg are provided according to aspects of the present invention which include: identifying a target genomic DNA sequence of a bird; identifying an insertion site in the target genomic DNA sequence, wherein a donor DNA sequence encoding the exogenous protein and inserted in the insertion site is under transcriptional control of a regulatory element that directs tissue-specific expression of the exogenous protein resulting in localization of the exogenous protein in an egg of the bird; providing transfected avian primordial germ cells by introducing into the avian primordial germ cells: 1) a clustered, regularly interspaced, short palindromic repeats (CRISPR)-associated protein (Cas protein) or nucleic acid sequence encoding the Cas protein, 2) guide nucleotide sequence or nucleic acid sequence encoding the guide nucleotide sequence; and 3) the donor DNA sequence encoding the exogenous protein, thereby forming a complex of the Cas protein and guide nucleotide sequence in the avian primordial germ cells, wherein the complex specifically binds to, and cleaves, the target genomic DNA sequence producing the insertion site, whereby the donor DNA sequence is inserted into genomic DNA of the avian primordial germ cells in the insertion site; introducing the transfected avian primordial germ cells into a population of recipient bird embryos and incubating the recipient bird embryos, generating germline chimera birds; obtaining a heterozygote and/or homozygote transgenic bird by breeding the germline chimera bird; and isolating the exogenous protein from an egg laid by a female transgenic bird.

Methods of producing an exogenous protein in a bird egg are provided according to aspects of the present invention wherein the bird is a chicken and the avian primordial germ cells are chicken primordial germ cells or wherein the bird is a quail and the avian primordial germ cells are quail primordial germ cells.

According to aspects of the present invention, methods of producing an exogenous protein in a bird egg are provided which further include introducing a transfection marker into the avian germ cells and identifying transfected avian primordial germ cells by presence of the transfection marker.

According to aspects of the present invention. DNA encoding the transfection marker is not integrated into the genomic DNA of the avian primordial germ cells and is not present in the germline chimera birds or transgenic bird.

According to aspects of the present invention, the transfection marker is a puromycin resistance gene and identifying transfected avian primordial germ cells by presence of the transfection marker comprises incubating putatively transfected avian primordial germ cells with puromycin.

According to aspects of the present invention, the guide nucleotide sequence includes a crRNA and a tracr RNA, which are combined in a single guide RNA molecule (gRNA).

According to aspects of the present invention, the donor DNA sequence comprises a first region homologous to the target sequence disposed 5' relative to the nucleotide sequence encoding the exogenous protein and second region homologous to the target sequence disposed 3' relative to the nucleotide sequence encoding the exogenous protein and the donor DNA sequence is inserted into the genome at the insertion site by homologous recombination.

According to aspects of the present invention, the donor DNA sequence comprises a first region homologous to the target sequence disposed upstream (5') relative to the nucleotide sequence encoding the exogenous protein and second region homologous to the target sequence disposed downstream (3') relative to the nucleotide sequence encoding the exogenous protein and the donor DNA sequence is inserted into the genome at the insertion site by homologous recombination and wherein a selection gene encoding a selection marker is positioned upstream (5') relative to the first region or downstream (3') relative to the second region.

According to aspects of the present invention, methods of producing an exogenous protein in a bird egg are provided which further include exposing the transfected avian primordial germ cells to a selection agent toxic to cells which do not express the selection marker, wherein the concentration of the selection agent and/or the amount of time of exposure of the cells to the selection agent produces a population of transfected PGCs wherein the donor DNA sequence encoding the exogenous protein and inserted in the insertion site is under transcriptional control of a regulatory element that directs tissue-specific expression of the exogenous protein resulting in localization of the exogenous protein in an egg of the bird and wherein the selection gene encoding a selection marker is not present in the genome of the transfected. PGCs.

According to aspects of the present invention, the donor sequence is inserted into the genome at the insertion site by non-homologous end joining.

According to aspects of the present invention, the nucleic acid sequence encoding the Cas protein and the nucleic acid sequence encoding, the guide sequence are present together in a vector.

According to aspects of the present invention, the regions homologous to the target sequence are localized at the 5' and 3' end of the donor nucleic acid sequence.

According to aspects of the present invention, introducing the transfected avian primordial germ cells into a population of recipient bird embryos includes administration of the transfected avian primordial germ cells into a subgerminal cavity of the recipient bird embryos.

According to aspects of the present invention, introducing the transfected avian primordial germ cells into a population of recipient bird embryos includes intravenous administration of the transfected avian primordial germ cells into the recipient bird embryos.

According to aspects of the present invention, the donor DNA sequence encoding the exogenous protein and inserted in the insertion site is under transcriptional control of a regulatory element that directs tissue-specific expression of the exogenous protein, wherein the regulatory element is a promoter of a gene encoding a protein preferentially expressed in oviduct tubular gland cells of the bird and localized in eggs of the bird, such as, but not limited to, an ovalbumin promoter, an avidin promoter, a clusterin promoter, a cystatin promoter, a lysozyme promoter, an ovoflavoprotein promoter, an ovoglobulin G2 promoter, an ovoglobulin G3 promoter, an ovoglycoprotein promoter, an ovoinhibitor promoter, an ovomacroglobulin promoter, an ovomucin promoter or an ovotransferrin promoter.

According to aspects of the present invention, the donor DNA sequence encoding the exogenous protein and inserted in the insertion site is under transcriptional control of a regulatory element that directs tissue-specific expression of the exogenous protein, wherein the regulatory element is a promoter of a gene encoding a liver secreted egg yolk protein preferentially expressed in hepatocytes of the bird and localized in eggs of the bird, such as, but not limited to, vitellogenin.

Methods of producing an exogenous protein in a bird egg are provided according to aspects of the present invention which include: identifying a target genomic DNA sequence of a bird; identifying an insertion site in the target genomic DNA sequence, wherein a donor DNA sequence encoding the exogenous protein and inserted in the insertion site is under transcriptional control of a regulatory element that directs tissue-specific expression of the exogenous protein resulting in localization of the exogenous protein in an egg of the bird; providing transfected avian primordial germ cells by introducing into the avian primordial germ cells: 1) a clustered, regularly interspaced, short palindromic repeats (CRISPR)-associated protein (Cas protein) or nucleic acid sequence encoding the Cas protein, 2) guide nucleotide sequence or nucleic acid sequence encoding the guide nucleotide sequence; and 3) the donor DNA sequence encoding the exogenous protein, thereby forming a complex of the Cas protein and guide nucleotide sequence in the avian primordial germ cells, wherein the complex specifically binds to, and cleaves, the target genomic DNA sequence producing the insertion site, whereby the donor DNA sequence is inserted into genomic DNA of the avian primordial germ cells in the insertion site, and wherein insertion of the donor DNA sequence at the insertion site destroys the guide RNA recognition sequence on the genomic DNA, thereby avoiding re-cleavage by the complex of the Cas protein and guide nucleotide sequence and thereby enhancing knock-in success; introducing the transfected avian primordial germ cells into a population of recipient bird embryos and incubating the recipient bird embryos, generating germline chimera birds; obtaining a heterozygote and/or homozygote transgenic bird by breeding the germline chimera bird; and isolating the exogenous protein from an egg laid by a female transgenic bird.

BRIEF DESCRIPTION OF THE DRAWINGS

FIG. 3 is a diagrammatic representation of OV Construct 1 hCECR1;

FIG. 4 is a diagrammatic representation of OV Construct 2 hCECR1;

FIG. 5 is a diagrammatic representation of OV Construct 3 hCECR1;

FIG. 6 is a diagrammatic representation of OV Construct 4 hCECR1;

FIG. 7 is a diagrammatic representation of Construct 5 Hc-P2A-Lc-P2A-OVAL; and

FIG. 8 is a diagrammatic representation of Construct 6 OVAL-P2A-Hc-P2A-Lc;

Figure 1:
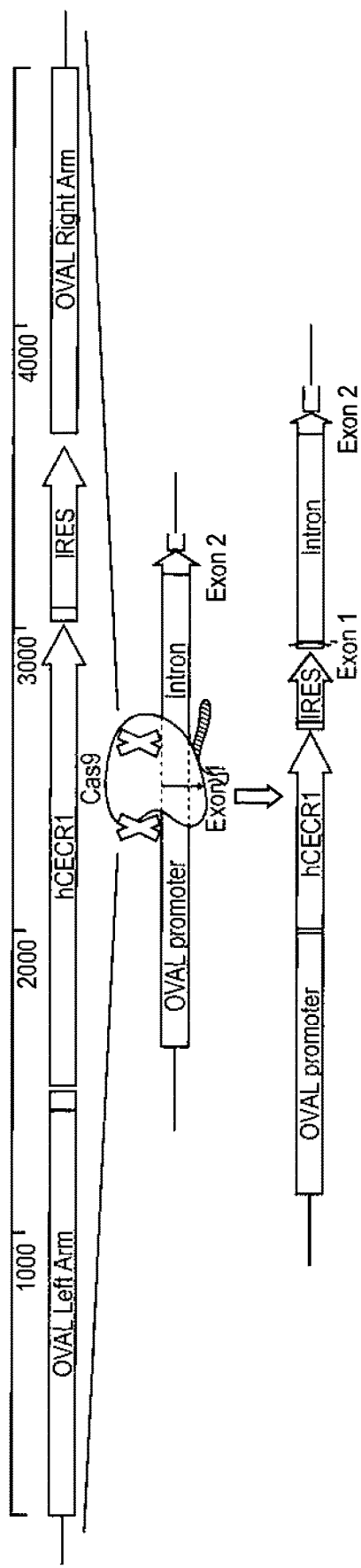
FIG. 1 is a schematic diagram of an aspect of a method using Cas9 and a gRNA to target the ovalbumin promoter-exon1 junction in the *Gallus gallus domesticus* genome in primordial germ cells (PGCs) and introduce a DNA double strand break (DSB) at an insertion site at the ovalbumin promoter-exon1 junction.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W. H. Freeman & Company, 2004; Herdewijn, P. (Ed.), Oligonucleotide Synthesis: Methods and Applications, Methods in Molecular Biology, Humana Press, 2004; and Kursad Turksen (Ed.), Embryonic stem cells: methods and protocols in Methods Mol Biol. 2002; 185, Humana Press; Current Protocols in Stem Cell Biology, ISBN: 9780470151808.

The singular terms "a," "an," and "the" are not intended to be limiting and include plural referents unless explicitly stated otherwise or the context clearly indicates otherwise.

Methods of producing an exogenous protein in a bird egg are provided according to aspects of the present disclosure.

According to aspects of methods disclosed herein, avian primordial germ cells (PGCs) are genome edited to produce avian primordial germ cells which are stably transfected to carry a DNA sequence encoding the exogenous protein in their genome. The stably transfected avian primordial germ cells are administered to avian embryos to produce germline chimeric transgenic birds, which are then used to produce heterozygote and homozygote transgenic birds which produce the exogenous protein in eggs.

The term "bird" as used herein refers to an avian of any species, including, but not limited to, chickens, quail and turkeys.

Avian primordial germ cells are generated early in embryogenesis, located in the germinal crescent. These cells migrate to the gonads via the blood circulatory system and eventually produce gametes. Primordial germs cells have been identified and isolated from various avian species such as turkey primordial germ cells as discussed in Wade et al., Poultry Science, 2014, 93(4):799-809; quail primordial germ cells as discussed in Ono et al., Exp. Anim., 1996, 45(4):347-52; and chicken as discussed in van de Lavoir, Nature, 441:766-769, 2006. By the methods of the present invention, a transgene is introduced into the genome of avian primordial germ cells to produce a transgenic chicken, transgenic turkey, transgenic quail and other avian species, that carry a transgene in the genetic material of its germ-line tissue to produce proteins of the invention. The primordial germ cells may be isolated freshly, maintained in culture, or in a particularly useful embodiment, reside within an avian embryo.

Isolation and culture of avian primordial germ cells is well-known, for example as described in van de Lavoir, Nature, 441:766-769, 2006; MacDonald et al., PLoS ONE 5(11): e15518, 2010; Petitte et al., Poult. Sci., 76:1084-1092, 1997; Mozdziak et al., Poult Sci 84: 594-600, 2005; Kimmell et al., Transgenic Res., 16:839-863, 2007; and Naito et al., J. Reprod. Fertil., 117: 291-298, 1999.

The genome edited avian primordial germ cells are generated by introducing: 1) a clustered, regularly interspaced, short palindromic repeats (CRISPR)-associated protein (Cas protein) or nucleic acid sequence encoding the Cas protein, 2) a target genomic DNA sequence-specific guide nucleotide sequence and 3) the donor DNA sequence encoding the exogenous protein, into the avian primordial germ cells, thereby forming a complex of the Cas protein and guide nucleotide sequence in the avian primordial germ cells with the target genomic DNA sequence of the cells.

The complex specifically binds to, and cleaves, the target genomic DNA sequence producing an insertion site. The donor DNA sequence is inserted into genomic DNA of the avian primordial germ cells in the insertion site producing stably transfected avian primordial germ cells carrying the DNA sequence encoding the exogenous protein in their genome.

Integration of the donor sequence into the genome is accomplished by homologous recombination by including regions homologous to the target sequence and is inserted into the genome at the insertion site according to embodiments. In such embodiments, regions homologous to the target sequence are localized at the 5' and 3' end of the donor nucleic acid sequence and termed homology arms. Alternatively, integration of the donor sequence into the genome proceeds by non-homologous end joining.

Homology arms can be in the range of about 75-2000 nucleotides in length, typically 500-1500, but may be longer or shorter.

Cas is an endonuclease that forms a complex with a guide nucleotide sequence to achieve site-specific DNA recognition and cleavage. The insertion site in target genomic DNA sequence is defined by the identification of the target site for cleavage by the Cas nuclease A guide nucleotide sequence, such as gRNA or a combination of crRNA and tracr RNA, can be any polynucleotide sequence which hybridizes with the target genomic sequence and directs sequence-specific binding of a CRISPR complex to the target genomic sequence.

Non-limiting examples of Cas proteins include Cast, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmrl, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, and modified versions thereof exemplified by *Streptococcus pyogenes* Cas9 D1135E variant; *Streptococcus pyogenes* Cas9 VRER variant; *Streptococcus pyogenes* Cas9 EQR variant; *Streptococcus pyogenes* Cas9 VQR variant; *Staphylococcus aureus* Cas9; *Neisseria meningitidis* Cas9; *Streptococcus thermophilus* Cas9; and *Treponema denticola* Cas9.

According to aspect of the disclosure, the Cas protein is *S. pyogenes* Cas9 protein, SwissProt accession number Q99ZW2 or a functional modified version thereof, exemplified by *S. pyogenes* Cas9 D1135E variant; *S. pyogenes* Cas9 VRER variant; and *S. pyogenes* Cas9 EQR variant.

A target genomic DNA sequence-specific guide nucleotide sequence includes a target genomic sequence-specific portion and a "scaffold" portion.

According to embodiments, the target genomic sequence-specific portion is a crRNA and the "scaffold" portion is a tracr RNA. A crRNA includes both a DNA-targeting segment and a segment that binds to a corresponding tracrRNA. The tracrRNA contains a palindromic region that forms a hairpin loop and a segment that binds to a corresponding crRNA. Together the tracrRNA bound to the corresponding crRNA form a double-stranded RNA duplex, which binds to the Cas nuclease, activating the Cas nuclease. The crRNA and tracrRNA can be provided as separate molecules which participate in the complex or as a single guide RNA molecule (sgRNA or gRNA).

A target site in the genome is identified for cleavage by Cas9 to generate an insertion site for the exogenous DNA. According to aspects, the target site in the genome is preferably unique to minimize insertion elsewhere in the genome and is located immediately 5' of a protospacer adjacent motif (PAM) sequence in the genome.

According to further aspects, the target site in the genome is selected to insert the donor DNA sequence into the genomic sequence recognized by the gRNA, thereby destroying the genomic sequence recognized by the gRNA so that further cleavage at the target site by Cas9-gRNA ribonucleoprotein complex is avoided, enhancing knock-in success.

The identity of the PAM site depends on the Cas nuclease used. The PAM site is 5'-NGG-3' for *Streptococcus pyogenes* Cas9. PAM sites for variants and orthologues of the *Streptococcus pyogenes* Cas9 and associated PAMs are known, such as, *Streptococcus pyogenes* Cas9 D1135E variant: 5'-NGG-3'; *Streptococcus pyogenes* Cas9 VRER variant: 5'-NGCG-3'; *Streptococcus pyogenes* Cas9 EQR variant: 5'-NGAG-3'; *Streptococcus pyogenes* Cas9 VQR variant: 5'-NGAN-3' or 5'-NGNG-3'; *Staphylococcus aureus*: 5'-NNGRRT-3' or 5"-NNGRR(N)-3'; *Neisseria meningitidis*: 5'-NNNNGATT-3'; *Streptococcus thermophilus*: 5'-NNAGAAW-3'; and *Treponema denticola*: 5"-NAAAAC-3'.

Expression Vectors

Expression vectors may be used to produce the encoded proteins and/or RNAs in PGCs. Alternatively, expression vectors may be used to produce any one or more of the Cas protein, crRNA, tracrRNA and sgRNA in another cell type or in a cell-free system. A Cas protein, crRNA, tracrRNA or sgRNA produced in another cell type or cell-free expression system can then be administered to the PGCs, such as by microinjection, or a transfection technique.

Optionally, a nucleic acid sequence encoding a Cas protein, a DNA sequence encoding the crRNA and a DNA sequence encoding the tracrRNA are all present together in an expression vector. Alternatively, the nucleic acid sequence encoding the Cas protein, the DNA sequence encoding the crRNA and the DNA sequence encoding the tracrRNA may each be present in a separate expression vector or any two thereof may be present together in an expression vector.

Optionally, a nucleic acid sequence encoding a Cas protein and a DNA sequence encoding an sgRNA are both present together in an expression vector. Alternatively, the nucleic acid sequence encoding the Cas protein and the DNA sequence encoding the sgRNA may each be present in a separate expression vector.

A nucleic acid encoding one or more proteins and/or one or more RNA components, tracrRNA, crRNA or sgRNA, can be cloned into an expression vector for transformation into prokaryotic or eukaryotic cells and expression of the encoded RNA molecules, peptides and/or protein(s).

The terms "expressing," "expresses" and "expression" refer to transcription of a gene to produce a corresponding mRNA and/or translation of the mRNA to produce the corresponding protein, as well as transcription of non-coding RNA molecules, such as a nucleic acid encoding one or more RNA components, tracrRNA, crRNA or sgRNA.

The term "vector" refers to a polynucleotide vehicle capable of transferring an exogenous polynucleotide into a cell. A vector can be, for example, a transfer vector or an expression vector.

The term "transfer vector" refers to a polynucleotide useful for transferring an exogenous polynucleotide into a cell which may include some, but does not necessarily include all, regulatory elements required for expression of the exogenous polynucleotide in the cell.

The term "expression vector" refers to a polynucleotide which, when introduced into an expression system, such as an appropriate host cell, can be transcribed into RNA or transcribed and translated into a polypeptide. An in vivo "expression system" is a suitable host cell containing an expression vector that can function to yield a desired expression product. Expression vectors may also be used to produce the encoded proteins in vitro, such as in in vitro expression systems.

According to embodiments, expression vectors used can be prokaryotic vectors, e.g., plasmids, or shuttle vectors, viral vectors, insect vectors, or eukaryotic vectors.

Expression is under control of one or more regulatory elements, such as a promoter. Numerous promoters are well known in the art and described, e.g., in Sambrook et al., Molecular Cloning, A Laboratory Manual (2nd ed. 1989; 3rd ed., 2001); Kriegler, Gene Transfer and Expression: A Laboratory Manual (1990); and Ausubel et al., Current Protocols in Molecular Biology.

In addition to the promoter, the expression vector typically contains a transcription unit or expression cassette that contains any regulatory elements required or desired for the expression of the nucleic acid. A typical expression cassette thus contains a promoter operably linked to a nucleic acid sequence encoding the protein or RNA to be expressed. Suitable promoter and enhancer elements are known in the art. For expression in a bacterial cell, suitable promoters include, but are not limited to, lacI, lacZ, T3, T7, gpt, lambda P and trc. For expression of a Cas and/or guide sequence(s) in an avian primordial germ cell, suitable promoters include, but are not limited to, SV40, UBC, CAG, EF1a, PGK, or CMV promoter.

The term "regulatory element" refers to a genetic element that controls an aspect of expression of an operably linked nucleic acid sequence. Examples of regulatory elements include, for example, promoters, enhancers, polyadenylation signals, termination signals, internal ribosome entry sites, 2A peptides and splicing signals. The phrase "operably linked" refers to a relationship between components which allows them to function as intended.

An internal ribosome entry site (IRES) or 2A peptide are useful for multicistronic expression. Examples of 2A peptides that can be used include, T2A, P2A, E2A and F2A, all well-known in the art.

In one embodiment, a nucleotide sequence encoding a protein or RNA to be expressed and an operably linked promoter are both positioned between 5' and 3' LTRs in a vector before introduction into avian primordial germ cells. In one embodiment, the vector is retroviral and the exogenous protein coding sequence and an operably linked promoter are both positioned between the 5' and 3' LTRs of a retroviral self-inactivating (SIN) vector. In one useful embodiment, the LTRs or retroviral vector is derived from the avian leukosis virus (ALV), murine leukemia virus (MLV), or lentivirus. Useful retroviruses for introducing a protein coding sequence into PGCs are the replication-deficient avian leucosis virus (ALV), the replication-deficient murine leukemia virus (MLV) and the lentivirus.

One or more expression vectors can be introduced into the PGCs by any transfection technique. The term "transfection" refers to methods for the introducing exogenous DNA into a host cell. Transfection techniques include electroporation, microinjection, biolistic methods, calcium-phosphate precipitation, cationic lipid-mediated transfection, DEAE-dextran transfection and the like. Transfection of a host cell produces a transfected host cell.

Optionally, one or more components of the CRISPR/Cas system, e.g. Cas protein and/or guide RNA, can be expressed outside the PGCs and administered to the cells, such as by microinjection or a transfection technique.

Donor DNA Sequences

A donor DNA sequence to be inserted into the genome encodes the exogenous protein to be expressed in the transgenic birds and localized in eggs laid by the transgenic bird.

The term "exogenous" refers to a foreign material, typically DNA or protein, introduced into a cell and not naturally present in the cell. The foreign material may be entirely foreign to the cell or may include some part which is naturally present in the cell.

The term "exogenous protein" as used herein refers to a protein not naturally present in an avian egg and is present in the egg of the bird laying the egg as a result of the expression of a coding sequence present in a transgene DNA sequence encoding the exogenous protein in the genome of the bird. The foreign protein may be entirely foreign to the cell or may include some part which is naturally present in the cell.

A donor DNA sequence is optionally contained in a vector such as described above. The vector can be a large-insert DNA vector such as, but not limited to, a bacterial artificial chromosome, a yeast artificial chromosome, a cosmid, a phagemid, or a fosmid.

The donor DNA sequence can be excised from the vector and introduced into the PGCs as circular or linear DNA.

Alternatively, the donor DNA sequence is introduced into the PGCs in a transfer vector for integration into the genome of the PGCs. Transfer vectors can be used for stable introduction of a donor DNA sequence into PGCs and, in conjunction with a CRISPR/Cas system, into the genome of an avian to produce proteins of the invention, such as antibodies, in specific tissues of an avian, for example, in the oviduct tissue of an avian, thereby producing avian eggs which contain the encoded exogenous protein.

A donor DNA sequence preferably includes a coding sequence encoding a signal peptide that will direct secretion of the protein expressed by the vector's coding sequence from the tubular gland cells of the oviduct or other cells which direct localization of proteins into an egg laid by the avian. Where an exogenous protein would not otherwise be secreted, the donor DNA sequence encoding the exogenous protein is modified to include a DNA sequence encoding a signal peptide. Optionally, the DNA sequence encoding the signal peptide is inserted in donor DNA sequence such that it is located at the N-terminus of the protein encoded by the DNA when expressed. The signal peptide can direct secretion of the exogenous protein expressed encoded by the donor DNA sequence into the egg of a hard shell egg.

Non-limiting examples of signal peptides that can be used include chicken lysozyme signal peptide MRSLLILVLCFL-PLAALG (SEQ ID NO: 1); chicken ovomucoid signal peptide MAMAGVFVLFSFVLCGFLPDAAFG (SEQ ID NO: 2); and chicken ovotransferrin signal peptide MKLILCTVLSLGIAAVCFA (SEQ ID NO: 3).

Additional signal peptides that can be used are known in the art or can be identified by sequence analysis using software packages such as SignalP, see for example, Bendtsen et al., J Mol Biol. 2004; 340:783-795.

The donor DNA sequence may include a marker gene, wherein the marker gene is operably linked to a promoter.

The donor DNA sequence may include co-transcribed first and second genes under the control of a tissue-specific regulatory element when inserted into the PGC genome and the second gene may be under translational control of an internal ribosome entry site (IRES).

The exogenous protein encoded by the donor DNA sequence can be any protein desired to be produced in an avian egg, such as proteins for pharmaceutical formulation and pharmaceutical use. Pharmaceutical proteins produced in avian eggs according to aspects of the present disclosure include, but are not limited to, antibodies, enzymes, cytokines, growth factors, hormones, blood factors and vaccine proteins.

According to aspects of the present invention, an exogenous protein encoded by the donor DNA sequence is a multimeric protein. According to aspects of the present invention, an exogenous protein encoded in the donor DNA sequence is an immunoglobulin, such as an antibody, and/or antigen binding fragment thereof. According to aspects of the present invention, an exogenous protein encoded in the donor DNA sequence is a multimeric protein such that a first exogenous protein and a second exogenous protein are encoded, expressed and localized in an egg produced by a transgenic avian according to aspects of the present invention.

An antibody encoded by a donor DNA sequence can be any of various antibodies, particularly those used in pharmaceutical, diagnostic and therapeutic applications. Antibodies and methods for preparation of antibodies are well-known in the art. As used herein, the terms "antibody" and "antibodies" encompass monoclonal antibodies, polyclonal antibodies, bispecific antibodies, multispecific antibodies, human antibodies, humanized antibodies, chimeric antibodies, camelized antibodies, single domain antibodies, single-chain Fvs (scFv), single chain antibodies, disulfide-linked Fvs (sdFv), and anti-idiotypic (anti-Id) antibodies and antigen-binding fragments of any of the above. Immunoglobulin molecules are of any type (e.g., IgG, IgE, IgM, IgD, IgA and IgY), class (e.g., IgG1, IgG2, IgG3, IgG4, IgA1 and IgA2), or subclass.

As used herein, the terms "antibody fragment" and "antigen-binding fragment" defines a fragment of an antibody that immunospecifically binds to a target biomarker. Antibody fragments may be generated by any technique known to one of skill in the art. For example, Fab and F(ab')2 fragments may be produced by proteolytic cleavage of immunoglobulin molecules, using enzymes such as papain (to produce Fab fragments) or pepsin (to produce F(ab')2 fragments). Antibody fragments are also produced by recombinant DNA technologies.

Antibodies, antigen-binding fragments, methods for their generation and methods for screening of generated antibodies for substantially specific binding to an antigen are known in the art and such antibodies, antigen binding fragments and methods are described in further detail, for instance, in Antibody Engineering, Kontermann, R. and Dübel, S. (Eds.), Springer, 2001; Harlow, E. and Lane, D., Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; Ausubel, F. et al., (Eds.), Short Protocols in Molecular Biology, Wiley, 2002; J. D. Pound (Ed.) Immunochemical Protocols, Methods in Molecular Biology, Humana Press, 2nd ed., 1998; B.K.C. Lo (Ed.), Antibody Engineering: Methods and Protocols, Methods in Molecular Biology, Humana Press, 2003; and Kohler, G. and Milstein, C., Nature, 256:495-497 (1975).

According to aspects of the present invention, an immunoglobulin polypeptide encoded by a donor DNA sequence is an immunoglobulin heavy chain polypeptide including a variable region or a variant thereof, and may further include a D region, a J region, a C region, or a combination thereof. An immunoglobulin polypeptide encoded by a donor DNA sequence may also be an immunoglobulin light chain polypeptide comprising a variable region or a variant thereof, and may further comprise a J region and a C region. According to aspects of the present invention, an exogenous protein encoded by the donor DNA sequence is an immunoglobulin heavy chain and an immunoglobulin light chain.

The present invention also contemplates multiple immunoglobulin regions that are derived from the same animal species, or a mixture of species including, but not only, human, mouse, rat, rabbit and chicken. In certain embodiments, the antibodies are human or humanized.

According to aspects of the present invention, an immunoglobulin polypeptide encoded by a donor DNA sequence includes an immunoglobulin heavy chain variable region, an immunoglobulin light chain variable region, and a linker peptide thereby forming a single-chain antibody capable of selectively binding an antigen.

Thus, in one particularly useful embodiment, antibodies produced in accordance with the invention are produced in a single chain foim. See, for example, Lee et al., Molecular Immunology (1999) vol. 36, p 61-71 which details the production of single chain antibodies, the disclosure of which is incorporated in its entirety herein by reference. For example, any antibody which can be produced in accordance with the invention in single chain form, including but not limited to each of the antibodies specifically disclosed herein, is contemplated for production in a single chain form in a transgenic avian oviduct.

Pharmaceutical antibodies encoded by the donor DNA sequence as the exogenous protein include, but are not limited to, any one or more of: abciximab, adalimumab, alemtuzumab, arcitumomab, basiliximab, bevacizumab, capromab pendetide, cetuximab, daclizumab, efalizumab, gemtuzumab, ibritumomab tiuxetan, infliximab, muromonab-CD3, nimotuzumab, nofetumomab, omalizumab, palivizumab, rituximab, tocilizumab, tositumomab, trastuzumab, and the like. Examples of other diagnostic or therapeutic antibodies that can be the encoded exogenous protein include, but are not limited to, any one or more of: mAb B72.3, arcitumomab, adecatumumab, apolizumab, bavituximab, belimumab, canakinumab, capromab, certolizumab, cixutumumab, conatumumab, denosumab, eculizumab, edrecolomab, epratuzumab, etaracizumab, farletuzumab, figitumumab, gantenerumab, golimumab, imciromab, iratumumab, lerdelimumab, lexatumumab, lintuzumab, lucatumumab, mapatumumab, metelimumab, natalizumab, necitumumab, ofatumumab, otelixizumab, ozogamicin, panitumumab, pritumumab, ranibizumab, robatumumab, satumomab, stamulumab, sulesomab, teplizumab, ustekinumab, visilizumab, votumumab, zalutumumab and zanolimumab.

Some other examples of therapeutic antibodies that may be produced in methods of the invention include, but are not limited, to BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Smart M195 which is a humanized anti-CD33 IgG antibody (Protein Design Lab/Kanebo); ICM3 is a humanized anti-ICAM3 antibody (ICOS Pharm); IDEC-114 is a primate anti-CD80 antibody (IDEC Pharm/Mitsubishi); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CATIBASF); CDP870 is a humanized anti-TNF-α Fab fragment (Celltech); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); and CAT-152, a human anti-TGF-β2 antibody (Cambridge Ab Tech).

Lysosomal storage enzymes encoded by the donor DNA sequence as the exogenous protein include, but are not limited to, any one or more of: L-iduronidase, iduronate-2-sulfatase, heparan-N-sulfatase, α-N-acetylglucosaminidase, acetylCoA:N-acetyltransferase, N-acetyl-alpha-glucosaminidase (NAGLU), galactose 6-sulfatase, β-galactosidase, N-acetylgalactosamine 4-sulfatase, β-glucuronidase, hyaluronoglucosaminidase, aspartylglucosaminidase, lysosomal acid lipase (LAL), cystine transporter, lamp-2, α-galactosidase A, α-galactosidase B, ceramidase, α-L-fucosidase, protective protein, glucocerebrosidase (β-glucosidase), galactocerebrosidase, α-glucosidase, β-galactosidase, β-hexosaminidase A, GM2-gangliosidosis type II (GM2)-activator, α-D-mannosidase, β-D-mannosidase, arylsulfatase A, saposin B, neuraminidase, phosphotransferase, phosphotransferase γ-subunit, multiple sulfatases, formylglycine-generating enzyme (FGE), palmitoyl protein thioesterase, tripeptidyl peptidase I, acid sphingomyelinase, cholesterol trafficking enzymes/intracellular cholesterol transporter, cathepsin K, sialic acid transporter, asparaginase; urokinase; tenecteplase, adenosine deaminase, palmitoyl-protein thioesterase 1, heparan sulfamidase, N-acetylglucosaminidase, alpha-glucosaminide N-acetyltransferase, galactosylceramidase (GALC), glucoronidase, NPC1, NPC2, agalsidase alfa, acid sphingomyelinase (ASM), N-acetylgalactosamine 6-sulfatase (GALNS or galactose 6-sulfatase), idursulfase, alpha-L-duronidase, galsulfase, arylsulfatase B, BM 102, lysosomal alpha-mannosidase (LAMAN), beta-hexosaminidase and alglucosidase alfa.

According to aspects of the present invention, an exogenous protein encoded in the donor DNA sequence can be, without limitation, Factor VIII, B-domain deleted Factor VIII, Factor Vila, factor IX, anticoagulants, hirudin, alteplase, tPA, reteplase, tPA-3 of 5 domains deleted, insulin, insulin lispro, insulin aspart, insulin glargine, long-acting insulin analogs, human growth hoimone (hGH), glucagons, follitropin-beta, follicle stimulating hormone (FSH), granulocyte macrophage colony-stimulating factor (GM-CSF), platelet-derived growth hormone (PDGF), interferon (IFN) alpha2, IFN alpha2a, IFN alpha2b, IFN-alpha, IFN-beta 1 b, IFN-beta, IFN-gammalb, interleukin (IL)-2, IL-11, hepatitis B surface antigen (HBSAG), outer surface protein A (OSPA, *Borrelia burgdorferi*), murine mAb directed against t-lymphocyte antigen, murine mAb directed against tag-72, tumor-associated glycoprotein, Fab fragments derived from chimeric mAb directed against platelet surface receptor gpII(b)/III(a), murine mAb fragment directed against tumor-associated antigen ca125, murine mAb fragment directed against human carcinoembryonic antigen, cea, murine mAb fragment directed against human cardiac myosin, murine mAb fragment directed against tumor surface antigen psma, murine mAb fragments (Fab/Fab2 mix) directed against hmw-maa, murine mAb fragment (Fab) directed against carcinoma-associated antigen, mAb fragments (fab) directed against nca 90, a surface granulocyte nonspecific cross reacting antigen, humanized mAb directed against the alpha chain of the i12 receptor, chimeric mAb directed against the alpha chain of the IL2 receptor, chimeric mab directed against TNF-alpha, humanized mAb directed against an epitope on the surface of respiratory synctial virus, humanized mAb directed against her 2, human epidermal growth factor receptor 2, human mAb directed against cytokeratin tumor-associated antigen anti-ctla4, dornase-alpha DNAse, beta glucocerebrosidase, TNF-alpha, IL-2-diptheria toxin antibody, TNFR-IgG fragment antibody laronidase, DNAses, alefacept, darbepoetin alfa (colony stimulating factor), murine mAb, rasburicase, agalsidase beta, teriparatide, parathyroid hormone derivatives, anakinra, biological modifier, nesiritide, human B-type natriuretic peptide (HBNP), colony stimulating factors, pegvisomant, human growth hormone receptor antagonist, recombinant activated protein c, immunoglobulin e (Ige) blocker, ibritumomab tiuxetan, ACTH, glucagon, somatostatin, somatotropin, thymosin, human mAb directed against bytokeratin tumor-associated antigen; parathyroid hormone, pigmentary hormones, somatomedin, erythropoietin, luteinizing hormone, chorionic gonadotropin, hypothalmic releasing factors, etanercept, antidiuretic hormones, prolactin and thyroid stimulating hormone.

According to aspects of the present invention, an exogenous protein encoded in the donor DNA sequence is lysosomal acid lipase (LAL). The amino acid sequence for human LAL is well known in the art, see, for example, Anderson. R. A. and Sando, G. N., "Cloning and Expression of cDNA Encoding Human Lysosomal Acid Lipase/Cholesteryl Ester Hydrolase", Journal of Biological Chemistry, Vol. 266, No. 33, Issue of November 25, pp. 22479-22484 (1991).

According to aspects of the present invention, an exogenous protein encoded in the donor DNA sequence is glucocerebrosidase. Sequence information for human glucocerebrosidase is well known in the art, see, and, for example, Sorge, et al., "Molecular cloning and nucleotide sequence of human glucocerebrosidase cDNA", Proc. Natl. Acad. Sci, Vol 82, pp 7289-7293 (1985).

Other protein therapeutics which can be produced in accordance with the invention include, without limitation, Factor VIII; B-domain deleted Factor VIII; Factor VIIa; Factor IX, anticoagulant; recombinant hirudin, anticoagulant; recombinant hirudin; alteplase, tPA; reteplase, human tPA-3 of 5 domains deleted; Factor XI; Factor XII (Hageman factor); Factor XIII; alpha2-antiplasmin; microplasmin; insulin lispro; Bio Lysprol, an insulin analog; insulin aspart; insulin glargine; long-acting insulin analog; hGH; glucagons; TSH; follitropin-beta FSH; salmon calcitonin; Teriparatide, a parathyroid hormone derivative; nesiritide, B-type natriuretic peptide (BNP); PDGH; lutropin alfa; choriogonadotropin alfa; somatropin pegvisomant, human growth hormone receptor antagonist; platelet derived growth factor (PDGF); Keratinocyte growth factor; fibroblast growth factor 23; insulin-like growth factor-1, IGF-1 complexed with IGFBP-3; HBsAg; vaccine containing HBsAgn as one component; OspA, a lipoprotein found on the surface of B burgorferi; hep B-IPV HIB vaccine; hep B-IPV vaccine; pneumococcal conjugate vaccine; Influenza virus vaccine live, intranasal; alefacept, Immunosuppressive agent; TNF-alpha; TNFR-IgG fragment antibody; abatacept; recombinant activated protein C; dornase-alpha DNAse; enfuvirtide (HIV fusion inhibitor) anakinra, botulinum toxins, e.g., Type A; samarium [153 m] lexidronam; perfultren; cetrorelix; eptifibatide; hepatitis B virus small surface antigen (HbsAg); eptotermin alfa; protein C; inactivated hepatitis A virus hepatitis B surface antigen; dibotermin alfa; IL-2-diptheria toxin antibody that targets cells displaying a surface IL-2 receptor; endostatin; and human insulin-like growth factor binding protein-6.

Exogenous proteins produced are isolated from eggs. Proteins produced in transgenic avians in accordance with the invention can be purified from an egg component, such as egg white or egg yolk, by any useful procedure such as those apparent to a practitioner of ordinary skill in the art of protein purification. For example, antibody molecules produced in transgenic avians in accordance with the invention can be purified from an egg component, such as egg white or egg yolk, by methods apparent to practitioners of ordinary skill in the art of protein purification. For example, antibodies produced in transgenic avians in accordance with the invention may be isolated using a Protein A column.

The isolated exogenous proteins can then be modified, if desired, for therapeutic use. For example, an isolated exogenous protein can be modified to include glycosylation, a conjugated moiety and/or a radionuclide. Non-limiting examples of included radionuclides are $^{86}$Y, $^{90}$Y, $^{111}$In, $^{125}$I $^{131}$I, $^{177}$Lu, $^{225}$Ac, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{201}$Tl, $^{188}$Re, $^{186}$Re and $^{99m}$Tc. Examples of modified proteins that can be produced include, but are not limited to, imciromab pentetate, capromab pendetide; gemtuzumab ozogamicin, satumomab pendetide, $^{111}$In-satumomab pendetide, $^{99m}$Tc-arcitumomab, conjugate of B72.3 and radioligand CYT 103, $^{131}$I-tositumomab, $^{90}$Y-ibritumomab tiuxetan, $^{99m}$Tc-fanolesomab; $^{99m}$Tc-arcitumomab, $^{99m}$Tc-exametazime, $^{99m}$Tc-sestamibi, $^{99m}$Tc-sulesomab, $^{99m}$Tc-tetrofosmin, $^{99m}$Tc-tilmanocept, $^{99m}$Tc-votumumab, $^{111}$In-capromab pendetide, $^{111}$In-imciromab, $^{111}$In-satumomab pendetide. $^{125}$I-minretumomab.

According to aspects of the present invention, an exogenous protein encoded in the donor DNA sequence is a glycosylated antibody, such as a cytotoxic antibody. For example, the invention includes the glycosylated composition of matter for anti-CD20; TNFR-Fc (e.g., TNF receptor type II-IgG, e.g., Enbrel); EPO-Fc (e.g., erythropoietin-Fc); GIRT-Fc (e.g., glucocorticoid induced tumor necrosis factor); cytotoxic IL-2/Fc as well as other cytotoxic antibodies.

The donor DNA sequence can include a DNA sequence from any of various organisms, such as a prokaryote or eukaryote, a mammal, a human, a non-human mammal, a rodent, a rabbit, a pig, a bovine, a deer, a sheep, a goat, a chicken, a cat, a dog, a ferret, a primate, a domesticated mammal, or an agricultural mammal or any other organism of interest.

According to preferred aspects the donor DNA sequence includes a DNA sequence encoding a human protein.

In addition to the DNA sequence encoding the exogenous protein to be inserted into the insert site, the donor DNA sequence includes a 5' flanking region and a 3' flanking region homologous to segments on either side of the insert site, surrounding the DNA sequence encoding the exogenous protein to be inserted into the insert site.

The donor DNA sequence is introduced into the PGCs by any transfection technique such as electroporation, microinjection, biolistic methods, calcium-phosphate precipitation, cationic lipid-mediated transfection, DEAE-dextran transfection and the like.

Insertion of the donor DNA sequence into the genome of the PGC produces a stable transfectant. The term "stable" and grammatical equivalents in reference to transfected cells refers to the integration of exogenous DNA into the genome of a transfected cell. Proper insertion of the donor DNA sequence in the insertion site in the PGC genome can be confirmed by various well-known methods, including PCR and Southern blot analysis.

Optionally, a transfection marker is introduced into the avian germ cells for identifying transfected avian primordial germ cells by presence of the transfection marker.

For example, expression vectors include a transfection marker such as a reporter genes and/or selection gene. Selection genes include, for example, those that impart resistance to an antibiotic such as puromycin, neomycin, G418, hygromycin or blasticidin, including, but not limited to puromycin-N-acetyltransferase, neomycin phosphotransferase, hygromycin B phosphotransferase, and blasticidin S deaminase.

Optionally, the DNA sequence encoding the transfection marker is not integrated into the genomic DNA of the avian primordial germ cells and is not present in the germline chimera birds or transgenic bird.

According to embodiments, methods include exposing the transfected avian primordial germ cells to a selection agent toxic to cells which do not express the selection marker, wherein the concentration of the selection agent and/or the amount of time of exposure of the cells to the selection agent produces a population of transfected PGCs wherein the donor DNA sequence encoding the exogenous protein is inserted in the insertion site and wherein the selection gene encoding a selection marker is not present in the genome of the transfected PGCs.

The concentration of the selection agent and/or the amount of time of exposure of the cells to the selection agent is lower than typically used to stringently select for transfected cells.

According to embodiments, a puromycin-resistance gene is disposed 5' or 3' with respect to the homology arms in a donor DNA sequence encoding the exogenous protein. When PGCs are transfected with a donor DNA sequence in this configuration, the cells are selected for with a low concentration of puromycin for about 2-3 days, producing a population of transfected PGCs that do not copy the puromycin-resistance gene into the genome. Low concentrations of puromycin are in the range of about 0.2-2.5 ug/ml, such as 0.25-2.0 ug/ml or 0.5-1.5 ug/ml.

According to aspects of the present invention, the transfection marker is a puromycin resistance gene and identifying transfected avian primordial germ cells by presence of the transfection marker comprises incubating putatively transfected avian primordial germ cells with puromycin.

When inserted and in place in the insertion site in the genome of the PGC, the exogenous DNA sequence encoding the exogenous protein is under transcriptional control of a regulatory element that directs expression of the exogenous protein resulting in localization of the exogenous protein in an egg of the bird.

Any useful promoter can be employed to direct expression of the exogenous protein. Both constitutive and tissue-specific promoters, such as, but not limited to, oviduct magnum-specific promoters (for proteins localized in egg white) or liver-specific promoters (for proteins localized in egg yolk), have proven suitable for expression of exogenous protein in the oviduct, resulting in localization of the exogenous protein in eggs laid by transgenic birds.

For example, the promoter can be a constitutive promoter such as a cytomegalovirus (CMV) promoter, a rous-sarcoma virus (RSV) promoter, a murine leukemia virus (MLV) promoter, a beta-actin promoter.

According to aspects of the present invention, when inserted and in place in the insertion site in the genome of the PGC, the exogenous DNA sequence encoding the exogenous protein is under transcriptional control of a regulatory element that directs tissue-specific expression of the exogenous protein resulting in localization of the exogenous protein in an egg of the bird. The regulatory element can be a naturally occurring regulatory element already present in the genome of the PGC or can be present in the donor DNA sequence and inserted into the insertion site along with the exogenous DNA sequence encoding the exogenous protein.

The phrase "tissue-specific expression" refers to preferential or exclusive expression in a particular tissue, subset of tissues, cell type or subset of cell types.

According to aspects of the disclosure, the regulatory element is a promoter of a gene encoding a protein preferentially expressed in oviduct tubular gland cells of the bird and localized in eggs of the bird. The promoter can also be an oviduct magnum specific promoter such as an ovalbumin promoter, a lysozyme promoter, a conalbumin promoter, an ovomucoid promoter, an ovomucin promoter or an ovotransferrin promoter.

According to aspects of the disclosure, the regulatory element is a promoter, or other regulatory element of a gene encoding a protein selected from the group consisting of: ovalbumin, conalbumin, avidin, clusterin, cystatin, lysozyme, ovoflavoprotein, ovoglobulin G2, ovoglobulin G3, ovoglycoprotein, ovoinhibitor, ovomacroglobulin, ovomucoid, ovomucin, ovostatin and ovotransferrin and the exogenous protein is localized in egg white. According to aspects of the disclosure, the regulatory element is an oviduct magnum specific promoter such as an ovalbumin promoter, a lysozyme promoter, a conalbumin promoter, an ovomucoid promoter, an ovomucin promoter or an ovotransferrin promoter.

As noted above, an appropriate signal sequence(s) is encoded by the donor DNA sequence such that the encoded exogenous protein is secreted from a cell in which it is expressed and localized in the egg of the avian. For example, the encoded exogenous protein includes a signal peptide which directs secretion into the lumen of the oviduct and into the egg white of the egg.

These and additional egg proteins, their gene sequences, promoters and other regulatory elements are well-characterized, see for example, Mann, Proteomics, 7:3558-3568, 2007; Mann et al., Proteome Sci., 9:7, 2011; Omana et al., Proteomics, 11:144-153, 2011; and Guerin-Dubiard et al., J. Agric. Food Chem., 54:3901-3910, 2006.

For example, a sequence of an ovalbumin promoter is shown herein below that can be used to direct tissue-specific expression of an exogenous protein resulting in localization of the exogenous protein in an egg of the bird. An ovalbumin promoter can be included in a donor DNA sequence for insertion in the genome of PGCs as described in examples herein. Alternatively, the donor DNA sequence can be inserted at an insertion site of the PGC genome such that it is operably linked to the endogenous ovalbumin promoter to direct tissue-specific expression of an exogenous protein encoded in the donor DNA sequence, resulting in localization of the exogenous protein in an egg of the bird.

According to aspects of the disclosure, the regulatory element is a promoter of a gene encoding a liver secreted egg yolk protein preferentially expressed in hepatocytes of the bird and localized in eggs of the bird.

According to aspects of the disclosure, the regulatory element is a promoter of a gene encoding a liver secreted egg yolk protein preferentially expressed in hepatocytes of the bird and localized in eggs of the bird is vitellogenin.

Transgenic Birds

The stably transfected avian primordial germ cells are introduced into a population of recipient bird embryos which are incubated until hatch, generating putative germline chimera birds. Introducing the transfected avian primordial genn cells into a population of recipient bird embryos includes administration of the transfected avian primordial germ cells into a subgerminal cavity of the recipient bird embryos, intravenous administration of the transfected avian primordial germ cells into the recipient bird embryos, or both.

The putative geiinline chimera birds are screened to identify chimera birds (G0) carrying the DNA sequence encoding the exogenous protein in their genome. A male germline chimera bird (G0) is crossed with a female bird, generating heterozygote transgenic birds (G1) carrying the DNA sequence encoding the exogenous protein in their genome. The exogenous protein can be isolated from an egg laid by a female transgenic bird (G1) carrying the DNA sequence encoding the exogenous protein in its genome. Heterozygote transgenic birds can be crossed to produce homozygote transgenic birds (G2) carrying the DNA sequence encoding the exogenous protein in its genome and the exogenous protein can be isolated from an egg laid by a female (G2) homozygote transgenic bird and all subsequent progeny generations and progeny thereof. Further crossings may be performed to obtain additional desirable genetic traits while retaining the DNA sequence encoding the exogenous protein in its genome.

The term "gemiline chimera," refers to a transgenic avian with a transgene in germ cells.

The term "heterozygote" refers to a transgenic avian with a transgene in one chromosome of a chromosome pair in all of its genome containing cells.

The term "homozygote" refers to a transgenic avian with a transgene in both chromosomes of a chromosome pair in all of its genome-containing cells.

The exogenous protein localized in the eggs of transgenic birds is then isolated by standard protein isolation methodologies.

Embodiments of inventive compositions and methods are illustrated in the following examples. These examples are provided for illustrative purposes and are not considered limitations on the scope of inventive compositions and methods.

EXAMPLES

Donor DNA Sequence Construction

The basic design for donor DNA sequences, constructs #1, #2, and #3, is ovalbumin (OV) promoter-transgene-IRES-ovalbumin gene, and for donor construct #4 is OV promoter-ovalbumin gene-IRES-transgene, shown schematically in FIGS. 3-6, respectively. 2. A 36-bp DNA sequence that does not code for amino acids (indicated as 'non-coding DNA in FIGS. 3-5) is inserted and functions as a spacer. OV leader is the 5' UTR sequence of OV gene. The DNA sequences of constructs 1-4 wherein hCECR1 is the transgene are provided herein. The DNA sequences of bicistronic constructs 5 and 6 wherein antibody heavy chain and light chain are transgenes are provided herein.

OV Construct 1 hCECR1

The donor DNA sequence OV Construct 1 hCECR1, shown diagrammatically in FIG. 3, was constructed stepwise by In-Fusion® cloning (Clontech) and restriction digestion-ligation cloning. The sequences of origin of replication (Ori), ampicillin-resistance gene (AmpR), and IRES were cloned from pOptiVEC™-TOPO® (Invitrogen). CECR1 gene was PCR-amplified from the human cDNA sample. SV40 promoter, puromycin-resistance gene, and BGHpA sequence were cloned from pTT22 (National Research Council Canada Biotechnology Research Institute). Ovalbumin gene promoter, exon 1 and intron 1 sequences were PCR-amplified from White Leghorn chicken genomic DNA. The resulting vector was sequenced to verify the correct DNA sequence.

Figure 2:
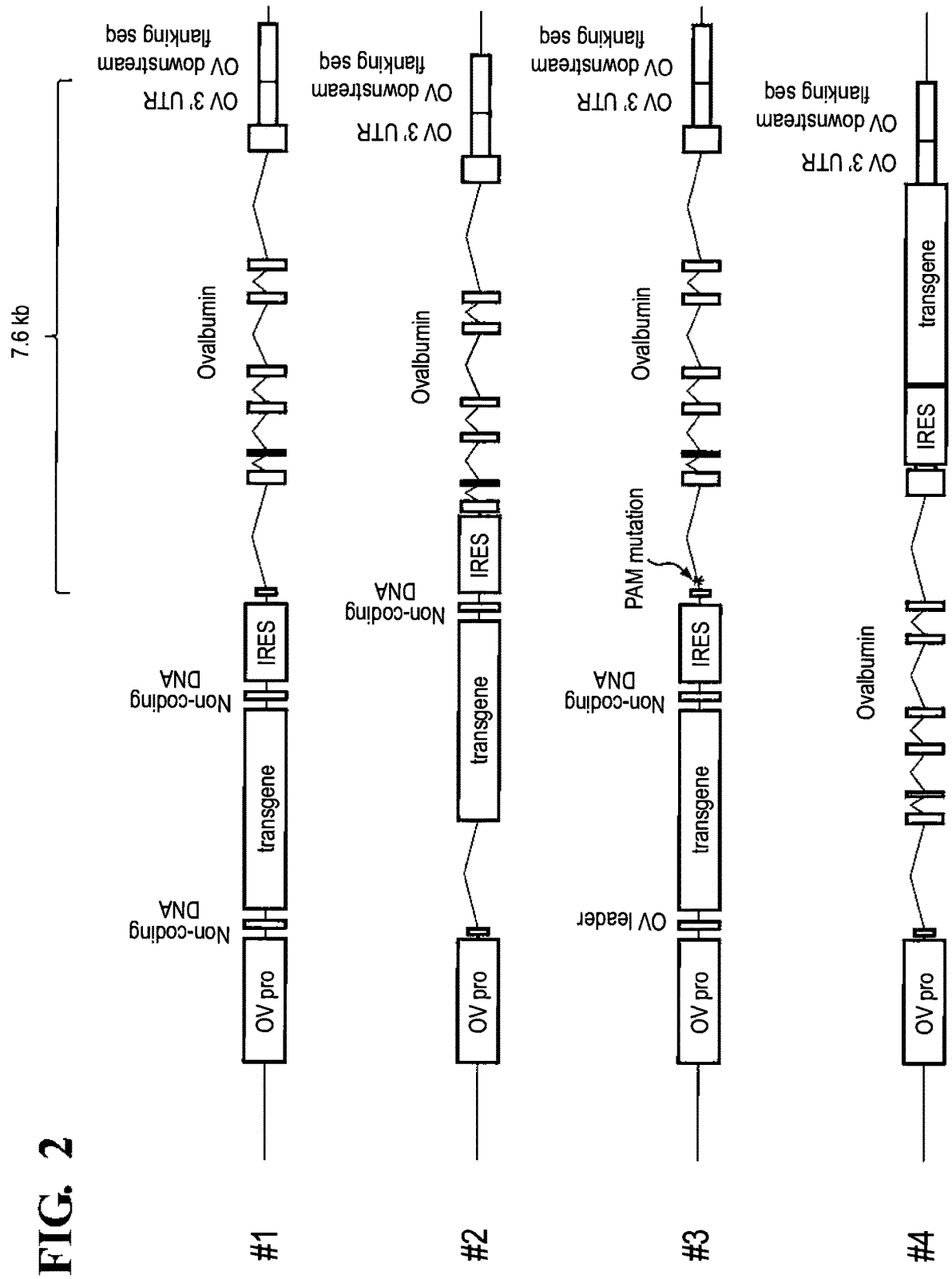
FIG. 2 shows a diagrammatic representation of 6 constructs each inserted into the genome of separate PGCs.

A guide RNA that can be used in a method according to the present invention with donor DNA sequence OV 1 hCECR1 (encoding hCECR1 or another exogenous protein) is CTAGCTGTATGTACAGACAC (SEQ ID NO: 4). A diagrammatic representation of the sequence inserted into the PGC genome is shown in FIG. 2 at #1.

OV Construct 2 hCECR1

The donor DNA sequence OV Construct 2 hCECR1, shown diagrammatically in FIG. 4, was constructed by NEBuilder® HiFi DNA assembly cloning (New England Biolabs) using the four DNA fragments with a 40-bp overlap on both ends. DNA fragment "A" which contains the sequences of origin of replication (Ori), ampicillin-resistance gene (AmpR), SV40 promoter, puromycin-resistance gene, and BGHpA, was generated from EcoRV-digested OV 1 hCECR1. DNA fragment "B" which contains the sequences of intron 1 and part of exon 2 from the ovalbumin gene, was PCR-amplified from White Leghorn chicken genomic DNA. DNA fragment "C" which contains the sequences of human CECR1 gene and IRES, was cloned from OV 1hCECR1. DNA fragment "D" which contains the sequences of exon 2, intron 2, exon 3, intron 3, exon 4, and part of intron 4 from the ovalbumin gene, was PCR-amplified from White Leghorn chicken genomic DNA.

A guide RNA that can be used in a method according to the present invention with donor DNA sequence OV 2 hCECR1 (encoding hCECR1 or another exogenous protein) is GACAACTCAGAGTTCACCAT (SEQ ID NO: 5). A diagrammatic representation of the sequence inserted into the PGC genome is shown in FIG. 2 at #2.

OV Construct 3 hCECR1

A donor DNA sequence OV Construct 3 hCECR1, shown diagrammatically in FIG. 5, containing (in order) part of the OV promoter, the full OV 5' UTR sequence (from both exon 1 and exon 2), human CECR1 gene, IRES, the OV exon 1, and part of the OV intron 1 (a G to C point mutation was introduced at the beginning of the intron 1 to abolish the gRNA recognition site), was synthesized and cloned into pUC57-Amp vector. The resulting vector was digested with BlpI and XbaI to obtain the desired DNA fragment. OV 1hCECR1 was also digested with BlpI and XbaI, and the DNA fragment that contains the sequences of origin of replication (Ori), ampicillin-resistance gene (AmpR), SV40 promoter, puromycin-resistance gene, BGHpA, part of the OV promoter, and part of the OV intron 1 was purified. The two DNA fragments were then ligated to generate OV 3 hCECR1 donor vector.

A guide RNA that can be used in a method according to the present invention with donor DNA sequence OV 3 hCECR1 (encoding hCECR1 or another exogenous protein) is TCAAAAGGTAAGCAACTCTC (SEQ ID NO: 6). A diagrammatic representation of the sequence inserted into the PGC genome is shown in FIG. 2 at #3.

OV Construct 4 hCECR1

The donor DNA sequence OV Construct 4 hCECR1, shown diagrammatically in FIG. 6, was constructed by NEBuilder® HiFi DNA assembly cloning using five DNA fragments with a 40-bp overlap on both ends. DNA fragment "E" which contains the sequences of origin of replication (Ori), ampicillin-resistance gene (AmpR), SV40 promoter, puromycin-resistance gene, and BGHpA, was cloned from OV Construct 1-hCECR1. DNA fragment "F" which contains the sequences of part of intron 7 and part of exon 8 from the ovalbumin gene, was PCR-amplified from White Leghorn chicken genomic DNA. DNA fragment "G" which contains the sequences of part of the OV 3' UTR, IRES, and part of human CECR1 gene, was cloned from OV 1 hLAL (same sequence as OV Construct 1 hCECR1 except that hCECR1 has been replaced with hLAL). DNA fragment "H" which contains the sequence of human CECR1 gene, was cloned from OV Construct 1-hCECR1. DNA fragment "I" which contains the sequences of part of human CECR1 gene, part of the OV 3' UTR, and OV downstream flanking sequences, was PCR-amplified from White Leghorn chicken genomic DNA. A 40-bp sequence from human CECR1 gene was included in the 5' PCR primer to introduce the desired overlapping end on DNA fragment "I."

A guide RNA that can be used in a method according to the present invention with donor DNA sequence OV 4 hCECR1 (encoding hCECR1 or another exogenous protein) is GTGCTCTGGGTCTTGTTGGA (SEQ ID NO: 7). A diagrammatic representation of the sequence inserted into the PGC genome is shown in FIG. 2 at #4.

Construct 5-Hc-P2A-Lc-P2A-OVAL

A DNA fragment containing (in order) part of the OV intron 1, the 5' UTR from the OV exon 2, antibody-Hc (heavy chain), GSG Linker, P2A, antibody-Lc (light chain), GSG linker, P2A, part of the OV exon 2, the OV intron 2, the OV exon 3, and part of the OV intron 3, was synthesized and cloned into pUC57-Amp vector. The resulting vector was digested with BglII and SnaBI to obtain the desired DNA fragment. OV 2 hCECR1 was also digested with BglII and SnaBI, and the DNA fragment that contains the sequences of origin of replication (Ori), ampicillin-resistance gene (AmpR), SV40 promoter, puromycin-resistance gene, BGHpA, part of the OV intron 1, part of the OV intron 3, the OV exon 4, and part of the OV intron 4, was purified. The two DNA fragments were then ligated to generate Construct 5 Hc-P2A-Lc-P2A-OVAL donor vector, shown diagrammatically in FIG. 7. The two encoded proteins in such constructs can be in any order, for example, Lc-P2A-Hc-P2A-OVAL.

A guide RNA that can be used in a method according to the present invention with donor DNA sequence Construct 5Hc-P2A-Lc-P2A-OVAL (encoding Hc and Lc, or other exogenous proteins) is GACAACTCAGAGTTCACCAT (SEQ ID NO:5). A diagrammatic representation of the sequence inserted into the PGC genome is shown in FIG. 2 at #5.

Construct 6 OVAL-P2AHc-P2A-Lc

A DNA fragment containing (in order) part of the OV exon 8, GSG Linker, P2A, antibody-Hc (heavy chain), GSG Linker, P2A, antibody-Lc (light chain), and part of the OV 3' UTR, was synthesized and cloned into pUC57-Amp vector. The resulting vector was digested with BbvCI and XbaI to obtain the desired DNA fragment. OV Construct 4-hNAGLU (same sequence as OV Construct 4 hCECR1 except that hCECR1 has been replaced with hNAGLU) was also digested with BbvCI and XbaI, and the DNA fragment that contains the sequences of origin of replication (Ori), ampicillin-resistance gene (AmpR), SV40 promoter, puromycin-resistance gene, BGHpA, part of the OV intron 7, part of the OV exon 8, part of the OV 3' UTR, and OV downstream flanking sequences, was purified. The two DNA fragments were then ligated to generate Construct 6 OVAL-P2A-Hc-P2A-Lc donor vector, shown diagrammatically in FIG. 8. The two encoded proteins in such constructs can be in any order, for example, OVAL-P2A-Lc-P2A-Hc.

A guide RNA that can be used in a method according to the present invention with donor DNA sequence Construct 6 OVAL-P2A-Hc-P2A-Lc (encoding He and Lc, or other exogenous proteins) is GTGCTCTGGGTCTTGTTGGA (SEQ ID NO: 7). A diagrammatic representation of the sequence inserted into the PGC genome is shown in FIG. 2 at #6.

PGC Transfection

PGCs were isolated from blood of White Leghorn chicken embryos and cultured on mitotically inactivated STO (Sandoz inbred mouse-derived thioguanine-resistant and ouabain-resistant cells) feeder cells (cat # CRL-1503, ATCC) prior to the transfection procedure.

One day before the transfection, wells of a 6-well plate or 10-cm plates containing mitotically inactivated mouse embryonic fibroblast cell line STO feeder cells at the density of $3\times10^4$ cells/cm$^2$ were prepared.

On the day of transfection, $5\times10^5$ PGCs were seeded in each well of a 6-well plate containing mitotically inactivated STO feeder cells.

If a 10-cm plate is used, seed $3\times10^6$ PGCs and use 6× of the transfection reagents. Typically, 7-9 wells of 6-well plates or four 10-cm plates are transfected with nucleic acid mixture (a) described below, and only 1 well or one 10-cm plate for nucleic acid mixture (b) and nucleic acid mixture (c).

The PGCs are transfected using Lipofectamine® 3000 and related reagents (ThermoFisher Scientific, Waltham, Mass.) in this example.

The following nucleic acid mixtures are prepared for the transfection:
a. 1.25 µg of [OV Construct 1 hCECR1]+1.25 µg of [CRISPR-gRNA for Construct1] in 125 µl OPTI-MEM® I reduced serum medium; the gRNA for this example is CTAGCTGTATGTACAGACAC (SEQ ID NO: 4)
b. (control for comparison with (a) for surviving PGCs) 1.25 µg [pEGFP-N1]+1.25 µg of [CRISPR-gRNA for Construct1] in 125 µl OPTI-MEM® I reduced serum medium
c. (control for checking transfection efficiency) 2.5 µg [pEGFP-N1] in 125 µl OPTI-MEM® I reduced serum medium The nucleic acid mixtures are vortexed, 5 µl of P3000® reagent is then added and the tubes are immediately vortexed again.

Three lipofection reagent mixtures containing 7.5 µl of Lipofectamine® 3000 and 125 µl of OPTI-MEM® I reduced serum medium each are prepared, mixing the contents well.

Each nucleic acid mixture is combined with a lipofection reagent mixture and the combination is incubated for 5 minutes at room temperature, and then added to PGCs in one culture well.

After 24-36 hours, puromycin is added to treat the cells in the wells at the concentration of 0.5 µg/mL. The PGCs are closely observed for the next 1-3 days. Once most of the PGCs transfected with nucleic acid mixture (b) die, usually at 48-52 hours after puromycin addition, the surviving PGCs transfected with nucleic acid mixture (a) are collected and re-seeded in a new well containing fresh mitotically inactivated STO feeder cells. No puromycin is present in the medium. Notably in this example, a puromycin-resistance gene is incorporated in the transfected PGCs for transient selection of the transfected PGCs and this selection marker is not incorporated into the targeted genome.

The transfected PGCs are then incubated in cell culture for 10-14 days for them to recover. The feeder cells do not have to be changed during this maintaining period. The culture medium may be changed or partially changed as needed. The PGCs are then expanded until they reach confluency in a 10-cm plate.

Genotyping is then performed to confirm correct genome editing in the PGCs.

Transgene Insertion into the Chicken Ovalbumin Locus

FIG. 1 is a schematic diagram of an aspect of a method using Cas9 and a gRNA to target the ovalbumin promoter-exon1 junction in the *Gallus gallus domesticus* genome in PGCs and introduce a DNA double strand break (DSB) at an insertion site at the ovalbumin promoter-exon1 junction.

In the example shown, DNA repair by homologous recombination results in insertion of the transgene, hCECR1 in the diagram shown in FIG. 1, to be expressed under control of the ovalbumin promoter. The donor vector contains the transgene-IRES in between two homologous arms flanking the DSB. The HR-mediated DNA repair inserts the transgene-IRES and destroys the gRNA recognition sequence, hence avoiding the re-cut by Cas9-gRNA ribonucleoprotein complex and enhancing knock-in success of transgene-IRES. In the diagram shown in FIG. 1, the human Cat Eye Syndrome Chromosome Region 1 (hCECR1) open reading frame (ORF) followed by IRES is copied from the donor vector into the targeted ovalbumin promoter-exon1 junction.

PCR was performed to screen for successful knock-in events in the PGCs. Three primer sets were used to confirm the successful genome-editing event after HR-mediated knock-in of hCECR1-IRES. One primer of the left junction primer pair (sense 5"-AGAACCTCCCTGTCTGGTAA-3' (SEQ ID NO: 8), and antisense 5'-GATAGAGCAGAGC-CGAAGAAAG-3' SEQ ID NO: 9) anneals to the transgene hCECR1, while the other primer anneals to a sequence outside the homologous left arm. A PCR product with the correct predicted size (1.716-bp) was obtained and sequenced to verify the knock-in. Similarly, one primer of the right junction primer pair (sense 5'-CCACGTTGT-GAGTTGGATAGT-3' (SEQ ID NO: 10), and antisense 5'-AAGCCAGTTGCCTCTACATATT-3' SEQ ID NO: 11) anneals to the IRES, while the other primer anneals to a sequence outside the homologous right arm. A PCR product with the correct predicted size (1,605-bp) was obtained and sequenced to verify the knock-in. A third primer set (sense 5'-TCTATGGCGTCAAAGGTCAAA-3' SEQ ID NO: 12, and antisense 5'-GGTAGCAAACTGTCCCAGAA-3' SEQ ID NO: 13) was used to examine the knock-in efficiency. One primer of the set anneals to a sequence inside the ovalbumin promoter, while the other primer anneals to a sequence inside the ovalbumin intron 1 but not within the homologous right arm. The 1,487-bp and 3,701-bp PCR bands obtained represent the products of amplification of unmodified genomic DNA and genome-edited genomic DNA, respectively.

Administering Transfected PGCs to Embryos

Transgenic PGCs are injected into fertile stage 10 wild-type embryos by microinjection in this example. Stage 10 eggs are collected and clean with 70% ethanol and a lab tissue. The eggs are set out horizontally on their side overnight at room temperature to allow rotation of the embryo to the top side of the yolk. Microinjection needles are made by pulling 50 µL micropipettes in half on needle puller leaving a 1-2 cm tapered end. A foot pump is used for injecting embryos. The foot pump consist of 0.5×2.5×15 inch flat wood board with syringe attached and latex tubing attached to aspirator tube assembly for the micro-capillary pipettes needles. The micro-capillary pipettes are calibrated to the volume of 7 µL and the very tip of the needle is colored to help visualize the depth when injecting. A Dremel is used to grind a 4-6 mm wide circular window into upward facing side of the egg. While leaving the membrane under the hard shell intact and using 70% ethanol to wipe the drilled area of excess dust. The egg is placed under focused light and with a scalpel blade cut out the inner membrane. The membrane is pulled out with forceps. The PGCs are slowly injected in a total volume of 7 µL into the center of the sub-germinal cavity of the stage 10 embryo. The colored tip of the needle should be visible in the area pellucida during the injection. The window is then sealed with enough hot glue by using a hot glue gun to cover the opening. The eggs are then transferred to the proper facility for hatching.

hCECR1 Knock-in (KI) G0 Screening

A TaqMan® screening assay was performed on genomic DNA isolated from semen samples of the G0 chickens that had been injected with hCECR1-IRES PGCs. 100 ng of DNA was used for each TaqMan® reaction with the following primer and probe set directed against hCECR1: sense 5'-CCCTGTGCTTCTTGCTGTTG-3' SEQ ID NO: 14, antisense 5"-GCCCGTGTTTCATCTATGGATAG-3' SEQ ID NO: 15, and probe 5"-TGGCAATGTCTTTCTTCG-GCTCTGC-3" SEQ ID NO: 16. The semen positivity for hCECR1 was determined to be around 6 to 7 percent.

G0 chickens harboring spermatozoa with the hCECR1 coding sequence in their genome were used to breed and produce hemizygous hCECR1-IRES transgenic chickens (G1).

hCECR1 KI G1 Screening

Genomic DNA was prepared from the blood of the G1 chickens and was screened by TaqMan® assay using the primer and probe set against hCECR1 to identify the hemizygous hCECR1-IRES transgenic G1 chickens. 100 ng of DNA was used for each TaqMan® reaction with the following primer and probe set: sense 5'-CCCTGTGCTTCTT-GCTGTTG-3' SEQ ID NO: 14, antisense 5'-GCCCGT-GTTTCATCTATGGATAG-3' SEQ ID NO: 15, and probe 5'-TGGCAATGTCTTTCTTCGGCTCTGC-3' SEQ ID NO: 16. Genomic DNA from the wild-type chicken blood was served as the negative control. This assay identified hemizygous G1s which will be used to breed for the homozygous G2s.

TaqMan®-positive hCECR1 KI G1s were further confirmed by traditional PCR

TaqMan® assay-identified G1 chickens were further tested by gel-PCR using an independent primer set against hCECR1. Genomic DNA from the wild-type chicken and TaqMan® assay-identified G1s were subjected to PCR using the following primer set: sense 5'-GTGGATTCTGCTG-GAGGATTAT-3' SEQ ID NO: 17 and antisense 5"-GAT-GAGACCAGAGATGGTGAAG-3' SEQ ID NO: 18. The resulting PCR products were resolved on 1% agarose gel. A 172-bp PCR amplicon was observed which confirmed the result of the TaqMan® assay.

Testing the expression of hCECR1 and chicken Ovalbumin from the transcript of hCECR1-IRES-Ovalbumin The whole chicken Ovalbumin gene including the inserted hCECR1-IRES sequences was cloned into pCDNA3.1 expression vector to be subjected to the control of a CMV promoter. The resulting plasmid was transiently transfected into 293 cells, and the expressed RNA transcripts were examined by RT-PCR and DNA sequencing to check a correct splicing event. Two PCR products (1,386-bp and 3,363-bp) were sequenced and the precise exon-exon junctions after splicing were confirmed. The endogenous lysosomal acid lipase (LIPA) gene was also amplified to show equal loading in all samples. The primer pair that was used in this LIPA PCR is: 5'-CCTGGTCTCGGAAACATAAG-3' SEQ ID NO: 19 (sense), and 5'-AGTGGTGCCTT-GAGAATGAC-3' SEQ ID NO: 20 (antisense). The expressed protein levels for the transgenes hCECR1 and chicken ovalbumin were examined by Western blotting. Adenosine deaminase assay was performed to monitor the ADA2 activity in culture medium, which estimated the ADA2 concentration to be 37.36 ng/µl (668.3 fmol/µl), whereas ELISA assay determined the ovalbumin expression level to be 8.24 ng/µl (193.0 fmol/µl).

The whole chicken ovalbumin gene including the inserted hCECR1-IRES sequences was cloned into pCDNA3.1 expression vector to be subjected to the control of a CMV promoter. The resulting plasmids (clone #2, #9, #10, and #11) and the two controls (mock-transfection and pEGFP-N1) were individually transfected into 293 cells using Lipofectamine® 3000 (Invitrogen) for transient overexpression. Two days after the transfection the culturing medium was collected, and the cells were rinsed two times with 1×PBS before harvested for RNA extraction. The RNA transcripts were reversely transcribed by oligo-dT, PCR-amplified by two primer pairs, respectively. For 1,386-bp amplification, the primer pair used for PCR is sense 5'-CCACGTTGT-GAGTTGGATAGT-3' (SEQ ID NO: 10), and antisense 5'-GAATGGATGGTCAGCCCTAAA-3' (SEQ ID NO: 21). For 3,363-bp amplification, the primer pair used for PCR is sense 5'-CCATCTCTGGTCTCATCCATTAC-3' (SEQ ID NO: 22), and antisense 5'-GCACATTCACAAGACCCAT-TAC-3' (SEQ ID NO: 23). The PCR products with the correct size were purified from gel and sequenced. The endogenous lysosomal acid lipase (LIPA) gene was also examined to demonstrate an equal loading in all samples. The DNA sequencing showed the precise exon-exon junctions between OV exon 1 and OV exon 2, between OV exon 2 and OV exon 3, between OV exon 3 and OV exon 4, between OV exon 4 and OV exon 5, between OV exon 5 and OV exon 6, between OV exon 6 and OV exon 7, and between OV exon 7 and OV exon 8. This result demonstrated that knock-in of hCECR1-IRES at the ovalbumin gene does not affect the precise RNA splicing event of the OVAL gene.

The collected culturing medium was examined by Western blotting using either the antibody against human CECR1/ADA2 (anti-CECR1 antibody, Cat. # PA5-30635, Thermo Fisher), or the antibody against chicken ovalbumin (anti-ovalbumin antibody, Cat. # ab181688, Abcam). Adenosine deaminase assay (Cat. # DZ117A-K, Diazyme) was also performed to examine the concentration of overexpressed human CECR1 proteins. Using the purified recombinant hCECR1 protein (r. ADA2) to generate a standard curve, we determined the overexpressed hCECR1 proteins to be 37.36 ng/µl (668.3 fmol/µl). ELISA assay (Chicken Egg Ovalbumin (Gal d 2) ELISA Kit, Cat. #6050, Alpha Diagnostic) was also performed, and the ovalbumin expression level was estimated to be 8.24 ng/µl (193.0 fmol/µl). Collectively, these results demonstrated that knock-in of hCECR1-IRES in the ovalbumin gene does not affect the effective expression of both hCECR1 transgene and the ovalbumin gene. Note that the relative expression level for hCECR1 and ovalbumin is ~3:1, indicating an efficient internal ribosomal entry and translation.

Transgenic chickens were generated according to methods described herein using CRISPR to "knock-in" a DNA sequence encoding human CECR1/ADA2 into PGC cells which were confirmed to carry the transgene as described above. Egg white samples from eggs of the transgenic chickens were assayed for adenosine deaminase activity and Western blotting, which determined the ADA2 concentration to be 345±4.9 mg/L.

Donor DNA Sequences

```
BGHpA - Constructs 1-6, SEQ ID NO: 24
CATGCCTGCTATTGTCTTCCCAATCCTCCCCCTTGCTGTCCTGCCCCACCCCACCCCCCAGAAT

AGAATGACACCTACTCAGACAATGCGATGCAATTTCCTCATTTTATTAGGAAAGGACAGTGGGA

GTGGCACCTTCCAGGGTCAAGGAAGGCACGGGGGAGGGGCAAACAACAGATGGCTGGCAACTAG

AAGGCACAGTCG

Puromycin - Constructs 1-6, SEQ ID NO: 25
TCAGGCACCGGGCTTGCGGGTCATGCACCAGGTGCGCGGTCCTTCGGGCACCTCGACGTCGGCG

GTGACGGTGAAGCCGAGCCGCTCGTAGAAGGGGAGGTTGCGGGGCGCGGAGGTCTCCAGGAAGG

CGGGCACCCCGGCGCGCTCGGCCGCCTCCACTCCGGGGAGCACGACGGCGCTGCCCAGACCCTT

GCCCTGGTGGTCGGGCGAGACGCCGACGGTGGCCAGGAACCACGCGGGCTCCTTGGGCCGGTGC

GGCGCCAGGAGGCCTTCCATCTGTTGCTGCGCGGCCAGCCGGGAACCGCTCAACTCGGCCATGC

GCGGGCCGATCTCGGCGAACACCGCCCCCGCTTCGACGCTCTCCGGCGTGGTCCAGACCGCCAC

CGCGGCGCCGTCGTCCGCGACCCACACCTTGCCGATGTCGAGCCCGACGCGCGTGAGGAAGAGT

TCTTGCAGCTCGGTGACCCGCTCGATGTGGCGGTCCGGGTCGACGGTGTGGCGCGTGGCGGGGT

AGTCGGCGAACGCGGCGGCGAGGGTGCGTACGGCCCGGGGGACGTCGTCGCGGGTGGCGAGGCG

CACCGTGGGCTTGTACTCGGTCAT

SV40 promoter - Constructs 1-6, SEQ ID NO: 26
TTTGCAAAAGCCTAGGCCTCCAAAAAAGCCTCCTCACTACTTCTGGAATAGCTCAGAGGCAGAG

GCGGCCTCGGCCTCTGCATAAATAAAAAAAATTAGTCAGCCATGGGGCGGAGAATGGGCGGAAC

TGGGCGGAGTTAGGGGCGGGATGGGCGGAGTTAGGGGCGGGACTATGGTTGCTGACTAATTGAG

ATGCATGCTTTGCATACTTCTGCCTGCTGGGGAGCCTGGGGACTTTCCACACCTGGTTGCTGAC

TAATTGAGATGCATGCTTTGCATACTTCTGCCTGCTGGGGAGCCTGGGGACTTTCCACACC

Intron 1-2, SEQ ID NO: 27
GTAAGCAACTCTCTGGAATTACCTTCTCTCTATATTAGCTCTTACTTGCACCTAAACTTTAAA

AAATTAACAATTATTGTGTTATGTGTTGTATCTTTAAGGGTGAAGTACCTGCGTGATACCCCCT

ATAAAAACTTCTCACCTGTGTATGCATTCTGCACTATTTTATTATGTGTAAAAGCTTTGTGTTT

GTTTTCAGGAGGCTTATTCTTTGTGCTTAAAATATGTTTTTAATTTCAGAACATCTTATCCTGT

CGTTCACTATCTGATATGCTTTGCAGTTTGCTTGATTAACTTCTAGCCCTACAGAGTGCACAGA

GAGCAAAATCATGGTGTTCAGTGAATTCTGGGGAGTTATTTTAATGTGAAAATTCTCTAGAAGT

TTAATTCCTGCAAAGTGCAGCTGCTGATCACTACACAAGATAAAAATGTGGGGGTGCATAAAC

GTATATTCTTACAATAATAGATACATGTGAACTTGTATACAGAAAAGAAAATGAGAAAAATGTG

TGTGCGTATACTCACACACGTGGTCAGTAAAAACTTTTGAGGGGTTTAATACAGAAAATCCAAT

CCTGAGGCCCCAGCACTCAGTACGCATATAAAGGGCTGGGCTCTGAAGGACTTCTGACTTTCAC
```

-continued

```
AGATTATATAAATCTCAGGAAAGCAACTAGATTCATGCTGGCTCCAAAAGCTGTGCTTTATATA

AGCACACTGGCTATACAATAGTTGTACAGTTCAGCTCTTTATAATAGAAACAGACAGAACAAGT

ATAAATCTTCTATTGGTCTATGTCATGAACAAGAATTCATTCAGTGGCTCTGTTTTATAGTAAA

CATTGCTATTTTATCATGTCTGCATTTCTCTTCTGTCTGAATGTCACCACTAAAATTTAACTCC

ACAGAAAGTTTATACTACAGTACACATGCATATCTTTGAGCAAAGCAAACCATACCTGAAAGTG

CAATAGAGCAGAATATGAATTACATGCGTGTCTTTCTCCTAGACTACATGACCCCATATAAATT

ACATTCCTTATCTATTCTGCCATCACCAAAACAAAGGTAAAAATACTTTTGAAGATCTACTCAT

AGCAAGTAGTGTGCAACAAACAGATATTTCTCTACATTTATTTTTAGGGAATAAAAATAAGAAA

TAAAATAGTCAGCAAGCCTCTGCTTTCTCATATATCTGTCCAAACCTAAAGTTTACTGAAATTT

GCTCTTTGAATTTCCAGTTTTGCAAGCCTATCAGATTGTGTTTTAATCAGAGGTACTGAAAAGT

ATCAATGAATTCT
```

Or Intron 1-2, alternate sequence - SEQ ID NO: 28
```
AGTACCTGCGTGATACCCCCTATAAAAACTTCTCACCTGTGTATGCATTCTGCACTATTTTATT

ATGTGTAAAAGCTTTGTGTTTGTTTTCAGGAGGCTTATTCTTTGTGCTTAAAATATGTTTTTAA

TTTCAGAACATCTTATCCTGTCGTTCACTATCTGATATGCTTTGCAGTTTGCTTGATTAACTTC

TAGCCCTACAGAGTGCACAGAGAGCAAATCATGGTGTTCAGTGAATTCTGGGGAGTTATTTTA

ATGTGAAAATTCTCTAGAAGTTTAATTCCTGCAAAGTGCAGCTGCTGATCACTACACAAGATAA

AAATGTGGGGGGTGCATAAACGTATATTCTTACAATAATAGATACATGTGAACTTGTATACAGA

AAAGAAAATGAGAAAAATGTGTGTGCGTATACTCACACACGTGGTCAGTAAAAACTTTTGAGGG

GTTTAATACAGAAAATCCAATCCTGAGGCCCCAGCACTCAGTACGCATATAAAGGGCTGGGCTC

TGAAGGACTTCTGACTTTCACAGATTATATAAATCTCAGGAAAGCAACTAGATTCATGCTGGCT

CCAAAAGCTGTGCTTTATATAAGCACACTGGCTATACAATAGTTGTACAGTTCAGCTCTTTATA

ATAGAAACAGACAGAACAAGTATAAATCTTCTATTGGTCTATGTCATGAACAAGAATTCATTCA

GTGGCTCTGTTTTATAGTAAACATTGCTATTTTATCATGTCTGCATTTCTCTTCTGTCTGAATG

TCACCACTAAAATTTAACTCCACAGAAAGTTTATACTACAGTACACATGCATATCTTTGAGCAA

AGCAAACCATACCTGAAAGTGCAATAGAGCAGAATATGAATTACATGCGTGTCTTTCTCCTAGA

CTACATGACCCCATATAAATTACATTCCTTATCTATTCTGCCATCACCAAAACAAAGGTAAAAA

TACTTTTGAAGATCTACTCATAGCAAGTAGTGTGCAACAAACAGATATTTCTCTACATTTATTT

TTAGGGAATAAAAATAAGAAATAAAATAGTCAGCAAGCCTCTGCTTTCTCATATATCTGTCCAA

ACCTAAAGTTTACTGAAATTTGCTCTTTGAATTTCCAGTTTTGCAAGCCTATCAGATTGTGTTT

TAATCAGAGGTACTGAAAAGTATCAATGAATTCTAGCTTTCACTGAACAAAAATATGTAGAGGC

AACTGGCTTCTGGGACAGTTTGCTACCCAAAAGACAACTGAATGCAAATACATAAATAGATTTA

TGAATATGGTTTTGAACATGCACATGAGAGGTGGATATAGCAACAGACACATTACCACAGAATT

ACTTTAAAACTACTTGTTAACATTTAATTGCCTAAAAACTGCTCGTAATTTACTGTTGTAGCCT

ACCATAGAGTACCCTGCATGGTACTATGTACAGCATTCCATCCTTACATTTTCACTGTTCTGCT

GTTTGCTCTAG
```

Or Intron 1-2, alternate sequence - SEQ ID NO: 29
```
GTAAGCAACTCTCTGCAATTACCTTCTCTCTATATTAGCTCTTACTTGCACCTAAACTTTAAAA

AATTAACAATTATTGTGTTATGTGTTGTATCTTTAAGGGTGAAGTACCTGCGTGATACCCCCTA

TAAAAACTTCTCACCTGTGTATGCATTCTGCACTATTTTATTATGTGTAAAAGCTTTGTGTTTG

TTTTCAGGAGGCTTATTCTTTGTGCTTAAAATATGTTTTTAATTTCAGAACATCTTATCCTGTC

GTTCACTATCTGATATGCTTTGCAGTTTGCTTGATTAACTTCTAGCCCTACAGAGTGCACAGAG
```

-continued

```
AGCAAAATCATGGTGTTCAGTGAATTCTGGGGAGTTATTTTAATGTGAAAATTCTCTAGAAGTT

TAATTCCTGCAAAGTGCAGCTGCTGATCACTACACAAGATAAAAATGTGGGGGGTGCATAAACG

TATATTCTTACAATAATAGATACATGTGAACTTGTATACAGAAAAGAAAATGAGAAAAATGTGT

GTGCGTATACTCACACACGTGGTCAGTAAAAACTTTTGAGGGGTTTAATACAGAAAATCCAATC

CTGAGGCCCCAGCACTCAGTACGCATATAAAGGGCTGGGCTCTGAAGGACTTCTGACTTTCACA

GATTATATAAATCTCAGGAAAGCAACTAGATTCATGCTGGCTCCAAAAGCTGTGCTTTATATAA

GCACACTGGCTATACAATAGTTGTACAGTTCAGCTCTTTATAATAGAAACAGACAGAACAAGTA

TAAATCTTCTATTGGTCTATGTCATGAACAAGAATTCATTCAGTGGCTCTGTTTTATAGTAAAC

ATTGCTATTTTATCATGTCTGCATTTCTCTTCTGTCTGAATGTCACCACTAAAATTTAACTCCA

CAGAAAGTTTATACTACAGTACACATGCATATCTTTGAGCAAAGCAAACCATACCTGAAAGTGC

AATAGAGCAGAATATGAATTACATGCGTGTCTTTCTCCTAGACTACATGACCCCATATAAATTA

CATTCCTTATCTATTCTGCCATCACCAAAACAAAGGTAAAAATACTTTTGAAGATCTACTCATA

GCAAGTAGTGTGCAACAAACAGATATTTCTCTACATTTATTTTTAGGGAATAAAAATAAGAAAT

AAAATAGTCAGCAAGCCTCTGCTTTCTCATATATCTGTCCAAACCTAAAGTTTACTGAAATTTG

CTCTTTGAATTTCCAGTTTTGCAAGCCTATCAGATTGTGTTTTAATCAGAGGTACTGAAAAGTA

TCAATGAATTCT (including the PAM mutation from TGG to TGC: in the

Intron 1-2 of OV Construct 3-hCECR1)

OV upstream flanking sequence (containing OVAL promoter)
1433 - constructs 1 and 3 SEQ ID NO: 30
GATATCTATACACAAATTATTAGTGTTTGATTGACACCAGATGACAGAGAAGTGCATCTGAGAA

AACCTATTCCCAATCTCCTTTCTCTTTCTGCAGACTGACATGCATTTCATAGGTAGAGATAACA

TTTACTGGGAAGCACATCTATCATCACAAAAAGCAGGCAAGATTTTCAGACTTTCTTAGTGGCT

GAAATAGAAGCAAAAGACGTGATTAAAAACAAAATGAAACAAAAAAAATCAGTTGATACCTGTG

GTGTAGACATCCAGCAAAAAAATATTATTTGCACTACCATCTTGTCTTAAGTCCTCAGACTTGG

CAAGGAGAATGTAGATTTCCACAGTATATATGTTTTCACAAAAGGAAGGAGAGAAACAAAAGAA

AATGGCACTGACTAAACTTCAGCTAGTGGTATAGGAAAGTAATTCTGCTTAACAGAGATTGCAG

TGATCTCTATGTATGTCCTGAAGAATTATGTTGTACTTTTTTCCCCCATTTTTAAATCAAACAG

TGCTTTACAGAGGTCAGAATGGTTTCTTTACTGTTTGTCAATTCTATTATTTCAATACAGAACA

ATAGCTTCTATAACTGAAATATATTTGCTATTGTATATTATGATTGTCCCTCGAACCATGAACA

CTCCTCCAGCTGAATTTCACAATTCCTCTGTCATCTGCCAGGCCATTAAGTTATTCATGGAAGA

TCTTTGAGGAACACTGCAAGTTCATATCATAAACACATTTGAAATTGAGTATTGTTTTGCATTG

TATGGAGCTATGTTTTGCTGTATCCTCAGAAAAAAAGTTTGTTATAAAGCATTCACACCCATAA

AAAGATAGATTTAAATATTCCAACTATAGGAAAGAAAGTGCGTCTGCTCTTCACTCTAGTCTCA

GTTGGCTCCTTCACATGCACGCTTCTTTATTTCTCCTATTTTGTCAAGAAAATAATAGGTCACG

TCTTGTTCTCACTTATGTCCTGCCTAGCATGGCTCAGATGCACGTTGTACATACAAGAAGGATC

AAATGAAACAGACTTCTGGTCTGTTACTACAACCATAGTAATAAGCACACTAACTAATAATTGC

TAATTATGTTTTCCATCTCCAAGGTTCCCACATTTTTCTGTTTTCTTAAAGATCCCATTATCTG

GTTGTAACTGAAGCTCAATGGAACATGAGCAATATTTCCCAGTCTTCTCTCCCATCCAACAGTC

CTGATGGATTAGCAGAACAGGCAGAAAACACATTGTTACCCAGAATTAAAAACTAATATTTGCT
```

```
                                -continued
CTCCATTCAATCCAAAATGGACCTATTGAAACTAAAATCTAACCCAATCCCATTAAATGATTTC

TATGGCGTCAAAGGTCAAACTTCTGAAGGGAACCTGTGGGTGGGTCACAATTCAGGCTATATAT

TCCCCAGGGCTCAGCCAGTGTCTGT hCECR1/ADA2 (1,536-bp) Constructs 1-4, SEQ ID NO: 31
ATGTTGGTGGATGGCCCATCTGAGCGGCCAGCCCTGTGCTTCTTGCTGTTGGCTGTGGCAATGT

CTTTCTTCGGCTCTGCTCTATCCATAGATGAAACACGGGCGCATCTGTTGTTGAAAGAAAAGAT

GATGCGGCTGGGGGGGCGGCTGGTGCTGAACACCAAGGAGGAGCTGGCCAATGAGAGGCTCATG

ACGCTCAAAATCGCTGAGATGAAGGAGGCCATGAGGACCCTGATATTCCCACCCAGCATGCACT

TTTTCCAGGCCAAGCATCTCATTGAGAGAAGTCAAGTGTTTAATATTCTAAGGATGATGCCAAA

AGGGGCTGCCTTGCACCTCCATGACATTGGCATCGTGACTATGGACTGGCTGGTGAGGAATGTC

ACCTACAGGCCTCACTGCCACATCTGTTTCACCCCAAGGGGGATCATGCAGTTCAGATTTGCTC

ACCCAACTCCCCGTCCATCAGAAAAATGTTCCAAGTGGATTCTGCTGGAGGATTATCGGAAGCG

GGTGCAGAACGTCACTGAGTTTGATGACAGCTTGCTGAGGAATTTCACTCTGGTGACCCAGCAC

CCGGAGGTGATTTACACAAACCAAAATGTTGTCTGGTCGAAATTTGAAACCATCTTCTTCACCA

TCTCTGGTCTCATCCATTACGCTCCAGTGTTCAGAGACTATGTCTTCCGGAGCATGCAGGAGTT

CTACGAGGACAACGTGCTCTACATGGAGATCAGAGCCAGGCTGCTGCCGGTGTATGAGCTCAGT

GGAGAGCACCATGACGAAGAGTGGTCAGTGAAGACTTATCAGGAAGTAGCTCAGAAGTTTGTGG

AAACTCATCCTGAGTTTATTGGAATCAAAATCATTTATTCGGATCACAGATCCAAAGATGTGGC

TGTCATCGCAGAATCCATCCGAATGGCCATGGGGCTCCGAATCAAGTTCCCCACGGTGGTGGCA

GGGTTTGACCTGGTGGGCATGAGGACACTGGCCACTCCTTGCATGACTACAAGGAAGCTCTGA

TGATCCCCGCCAAGGATGGCGTTAAGCTGCCTTACTTCTTCCACGCCGGAGAAACAGACTGGCA

GGGTACTTCCATAGACAGGAACATTCTGGATGCTCTGATGCTGAACACTACCAGAATCGGCCAT

GGATTTGCTTTGAGCAAACACCCCGCAGTCAGGACTTATTCCTGGAAAAAGGACATCCCCATAG

AAGTCTGTCCCATCTCTAACCAGGTGCTGAAACTGGTGTCTGACTTGAGGAACCACCCTGTAGC

CACTCTGATGGCCACTGGGCACCCCATGGTGATCAGCTCTGATGACCCAGCTATGTTTGGTGCC

AAAGGCTTGTCCTATGATTTCTATGAGGTCTTCATGGGCATTGGGGGGATGAAGGCTGATCTGA

GGACCCTCAAACAGCTGGCCATGAACTCTATCAAGTACAGTACCCTGTTGGAGAGTGAGAAAAA

TACTTTCATGGAAATATGGAAGAAGAGATGGGATAAGTTCATAGCAGATGTGGCTACAAAGTGA

Non-coding DNA
GGAAGCGGA

IRES - Constructs 1-4, SEQ ID NO: 32
GCCGCCCCTCTCCCTCCCCCCCCCCTAACGTTACTGGCCGAAGCCGCTTGGAATAAGGCCGGTG

TGCGTTTGTCTATATGTTATTTTCCACCATATTGCCGTCTTTTGGCAATGTGAGGGCCCGGAAA

CCTGGCCCTGTCTTCTTGACGAGCATTCCTAGGGGTCTTTCCCCTCTCGCCAAAGGAATGCAAG

GTCTGTTGAATGTCGTGAAGGAAGCAGTTCCTCTGGAAGCTTCTTGAAGACAAACAACGTCTGT

AGCGACCCTTTGCAGGCAGCGGAACCCCCCACCTGGCGACAGGTGCCTCTGCGGCCAAAAGCCA

CGTGTATAAGATACACCTGCAAAGGCGGCACAACCCCAGTGCCACGTTGTGAGTTGGATAGTTG

TGGAAAGAGTCAAATGGCTCTCCTCAAGCGTATTCAACAAGGGGCTGAAGGATGCCCAGAAGGT

ACCCCATTGTATGGGATCTGATCTGGGGCCTCGGTACACATGCTTTACATGTGTTTAGTCGAGG

TTAAAAAAACGTCTAGGCCCCCCGAACCACGGGGACGTGGTTTTCCTTTGAAAAACACGATGAT

AATATGGCCACA
```

-continued

5'-UTR from OV Exon 1 - Constructs 1 and 3, SEQ ID NO: 33
ACATACAGCTAGAAAGCTGTATTGCCTTTAGCACTCAAGCTCAAAAG 5'-UTR from OV Exon 2 - constructs 2, 3 and 5 SEQ ID NO: 34
ACAACTCAGAGTTCACC ori (origin of replication) - constructs 1-6, SEQ ID NO: 35
ATGTGAGCAAAAGGCCAGCAAAAGGCCAGGAACCGTAAAAAGGCCGCGTTGCTGGCGTTTTTCC

ATAGGCTCCGCCCCCCTGACGAGCATCACAAAAATCGATGCTCAAGTCAGAGGTGGCGAAACCC

GACAGGACTATAAAGATACCAGGCGTTTCCCCCTGGAAGCTCCCTCGTGCGCTCTCCTGTTCCG

ACCCTGCCGCTTACCGGATACCTGTCCGCCTTTCTCCCTTCGGGAAGCGTGGCGCTTTCTCATA

GCTCACGCTGTAGGTATCTCAGTTCGGTGTAGGTCGTTCGCTCCAAGCTGGGCTGTGTGCACGA

ACCCCCCGTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAGGTATGTAG

GCGGTGCTACAGAGTTCTTGAAGTGGTGGCCTAACTACGGCTACACTAGAAGAACAGTATTTGG

TATCTGCGCTCTGCTGAAGCCAGTTACCTTCGGAAAAAGAGTTGGTAGCTCTTGATCCGGCAAA

CAAACCACCGCTGGTAGCGGTGGTTTTTTTGTTTGCAAGCAGCAGATTACGCGCAGAAAAAAAG

GATCTCAAGAAGATCCTTTGATCTTTTCTACGGGGTC

Ampicillin resistant gene (AmpR) - constructs 1-6, SEQ ID NO: 36
TTACCAATGCTTAATCAGTGAGGCACCTATCTCAGCGATCTGTCTATTTCGTTCATCCATAGTT

GCCTGACTCCCCGTCGTGTAGATAACTACGATACGGGAGGGCTTACCATCTGGCCCCAGTGCTG

CAATGATACCGCGAGACCCACGCTCACCGGCTCCAGATTTATCAGCAATAAACCAGCCAGCCGG

AAGGGCCGAGCGCAGAAGTGGTCCTGCAACTTTATCCGCCTCCATCCAGTCTATTAATTGTTGC

CGGGAAGCTAGAGTAAGTAGTTCGCCAGTTAATAGTTTGCGCAACGTTGTTGCCATTGCTACAG

GCATCGTGGTGTCACGCTCGTCGTTTGGTATGGCTTCATTCAGCTCCGGTTCCCAACGATCAAG

GCGAGTTACATGATCCCCCATGTTGTGCAAAAAAGCGGTTAGCTCCTTCGGTCCTCCGATCGTT

GTCAGAAGTAAGTTGGCCGCAGTGTTATCACTCATGGTTATGGCAGCACTGCATAATTCTCTTA

CTGTCATGCCATCCGTAAGATGCTTTTCTGTGACTGGTGAGTACTCAACCAAGTCATTCTGAGA

ATAGTGTATGCGGCGACCGAGTTGCTCTTGCCCGGCGTCAATACGGGATAATACCGCGCCACAT

AGCAGAACTTTAAAAGTGCTCATCATTGGAAAACGTTCTTCGGGGCGAAAACTCTCAAGGATCT

TACCGCTGTTGAGATCCAGTTCGATGTAACCCACTCGTGCACCCAACTGATCTTCAGCATCTTT

TACTTTCACCAGCGTTTCTGGGTGAGCAAAAACAGGAAGGCAAAATGCCGCAAAAAAGGGAATA

AGGGCGACACGGAAATGTTGAATACTCAT

Promoter for AmpR - constructs 1-6, SEQ ID NO: 37
ACTCTTCCTTTTTCAATATTATTGAAGCATTTATCAGGGTTATTGTCTCATGAGCGGATACATA

TTTGAATGTATTTAGAAAAATAAACAAATAGGGGTTCCGCG

Exon2 (1-180)_intron2-3(181-431)_exon3(432-482)_intron3-
4(483-1063)_ exon4(1064-1154)_intron4-5(1155-1500) SEQ ID NO:
53: as indicated in OV Construct 2-hCECR1 and Construct 5-Hc-
P2A-Lc-P2A-OVAL
TCAGAGTTCACCATGGGCTCCATCGGTGCAGCAAGCATGGAATTTTGTTTTGATGTATTCAAGG

AGCTCAAAGTCCACCATGCCAATGAGAACATCTTCTACTGCCCCATTGCCATCATGTCAGCTCT

AGCCATGGTATACCTGGGTGCAAAAGACAGCACCAGGACACAAATAAATAAGGTGAGCCTACAG

TTAAAGATTAAAACCTTTGCCCTGCTCAATGGAGCCACAGCACTTAATTGTATGATAATGTCCC

TTGGAAACTGCATAGCTCAGAGGCTGAAAATCTGAAACCAGAGTTATCTAAAAGTGTGGCCACC

TCCAACTCCCAGAGTGTTACCCAAATGCACTAGCTAGAAATCTTGAAACTGGATTGCATAACTT

CTTTTTGTCATAACCATTATTTCAGCTACTATTATTTTCAATTACAGGTTGTTCGCTTTGATAA

-continued

ACTTCCAGGATTCGGAGACAGTATTGAAGCTCAGGTACAGAAATAATTTCACCTCCTTCTCTAT

GTCCCTTTCCTCTGGAAGCAAAATACAGCAGATGAAGCAATCTCTTAGCTGTTCCAAGCCCTCT

CTGATGAGCAGCTAGTGCTCTGCATCCAGCAGTTGGGAGAACACTGTTCATAAGAACAGAGAAA

AAGAAGGAAGTAACAGGGGATTCAGAACAAACAGAAGATAAAACTCAGGACAAAAATACCGTGT

GAATGAGGAAACTTGTGGATATTTGTACGCTTAAGCAAGACAGCTAGATGATTCTGGATAAATG

GGTCTGGTTGGAAAAGAAGGAAAGCCTGGCTGATCTGCTGGAGCTAGATTATTGCAGCAGGTAG

GCAGGAGTTCCCTAGAGAAAGTATGAGGGAATTACAGAAGAAAAACAGCACAAAATTGTAAAT

ATTGGAAAAGGACCACATCAGTGTAGTTACTAGCAGTAAGACAGACAGGATGAAAAATAGTTTT

GTAAACAGAAGTATCTAACTACTTTACTCTGTTCATACACTACGTAAAACCTACTAAGTAATAA

AACTAGAATAACAACATCTTTCTTTCTCTTTGTATTCAGTGTGGCACATCTGTAAACGTTCACT

CTTCACTTAGAGACATCCTCAACCAAATCACCAAACCAAATGATGTTTATTCGTTCAGCCTTGC

CAGTAGACTTTATGCTGAAGAGATACCCAATCCTGCCAGTAAGTTGCTCTAAAATCTGATCT

GAGTGTATTTCCATGCCAAAGCTCTACCATTCTGTAATGCAAAAACAGTCAGAGTTCCACATGT

TTCACTAAGAAAATTTCTTTTTCTCTTGTTTTTACAAATGAAAGAGAGGACAAATAACATTTCT

CTATCACCGACCTGAAACTCTACAGTCTTCAGAGAATGAATGGCTTGCTAAAAGAATGTCAAAT

CTTACCATACAGCTATTTCATATTACACTACTAAATACACTATAAGGCATAGCATGTAGTAATA

CAGTGTAAAATAGCTTTTTACACTACTA

Intron 7-8 - constructs 4 and 6, SEQ ID NO: 38
TGTAATAAATGAGAATTCATTGAAATGTTAGTATGCTAACTCAATCTAAATTATAAAGATAAAG

AGGCATTTAATCACAGCTAGATTTCCATCACTTGTGACAGACAGGCATATGAATGATTATGTAC

AGCTCTAGGAAAAAAAGTATGTAGGAAAACTAGTACATTTTGATTAGAAAGTCTGAAAATGAGG

TGCCTTGATCCAAGAGAATACGTGTGTTTGAGAAAAAAAAAGTTTGGATAGAGGTGGTAAGAGA

GAATATATTGAAATGGTGTTTCTACAAACTGCCATGGCCAGATTTGTGTAAGAGACATTCAGTA

AGTAGGCAAGGAAAGAAATATTACTAGGTACAAAGCAACATTAGTAATACCAAAAGAAACCAAT

TATTCCAGATGCCAATCTCGTAATAGGGTTAAGAGATTTCCACCCCTCTAGTGGTCACCAGTGC

AACCAGTAACTTTGCTAATTTACATTTTCTTTTTTTAAATGGCAGATATAGCTTTGAACTGAGT

GATCATGAACTGGTACTGTGTAAATAAGATGGAAGCATACTTGGCAGCTAAACTTCTAGTTTTT

AAAAACTCAAATTCTCTTGAAAGATCAGTTCCCAGTCTAGTAACAGCTGATAGTTTAAGTATCA

GTAATTGGCTACCATTAACAACTGGCTCCTGAGAGGTCTTAAATGTAGAGACAGCTTTAAACTC

AAAAGCACAGAGTGATTTTTAGAATAGACTTCCCAAGCAAAGAAAATAAACAGGGAGGAGCTTT

AAGGGAGTAGCCATCTCATTATTATTATTATTTAAAGAAATGGCAGCAAGCCTACAAAAGAAAA

ATAAGACAGAGCAGAGAAGAAAGAGTCATGGTATGCTTTTCTATCTTAGCAAAATTAATCTCTA

CATGCCTAGGAAAAAGCCATGACAAGAGCAATCAGTTCAAAAGGTGTATGCAAAAAACCACATA

ATAGTAACTAGTACTGCATTGCCAGGAAGGAAGTTATGTCGCCATTCCATGGATCTCATTCTCA

TTTCCTTGCAG

Or alternate sequence Intron 7-8 - constructs 4 and 6, SEQ ID NO: 39
ATAAATGAGAATTCATTGAAATGTTAGTATGCTAACTCAATCTAAATTATAAAGATAAAGAGGC

ATTTAATCACAGCTAGATTTCCATCACTTGTGACAGACAGGCATATGAATGATTATGTACAGCT

CTAGGAAAAAAAGTATGTAGGAAAACTAGTACATTTTGATTAGAAAGTCTGAAAATGAGGTGCC

TTGATCCAAGAGAATACGTGTGTTTGAGAAAAAAAAAGTTTGGATAGAGGTGGTAAGAGAGAAT

ATATTGAAATGGTGTTTCTACAAACTGCCATGGCCAGATTTGTGTAAGAGACATTCAGTAAGTA

-continued

```
GGCAAGGAAAGAAATATTACTAGGTACAAAGCAACATTAGTAATACCAAAAGAAACCAATTATT

CCAGATGCCAATCTCGTAATAGGGTTAAGAGATTTCCACCCCTCTAGTGGTCACCAGTGCAACC

AGTAACTTTGCTAATTTACATTTTCTTTTTTTAAATGGCAGATATAGCTTTGAACTGAGTGATC

ATGAACTGGTACTGTGTAAATAAGATGGAAGCATACTTGGCAGCTAAACTTCTAGTTTTTAAAA

ACTCAAATTCTCTTGAAAGATCAGTTCCCAGTCTAGTAACAGCTGATAGTTTAAGTATCAGTAA

TTGGCTACCATTAACAACTGGCTCCTGAGAGGTCTTAAATGTAGAGACAGCTTTAAACTCAAAA

GCACAGAGTGATTTTTAGAATAGACTTCCCAAGCAAAGAAAATAAACAGGGAGGAGCTTTAAGG

GAGTAGCCATCTCATTATTATTATTTAAAGAAATGGCAGCAAGCCTACAAAAGAAAAATAA

GACAGAGCAGAGAAGAAAGAGTCATGGTATGCTTTTCTATCTTAGCAAAATTAATCTCTACATG

CCTAGGAAAAAGCCATGACAAGAGCAATCAGTTCAAAAGGTGTATGCAAAAAACCACATAATAG

TAACTAGTACTGCATTGCCAGGAAGGAAGTTATGTCGCCATTCCATGGATCTCATTCTCATTTC

CTTGCAG
```

Exon 8 - constructs 4 and 6, SEQ ID NO: 40
```
CTTGAGAGTATAATCAACTTTGAAAAACTGACTGAATGGACCAGTTCTAATGTTATGGAAGAGA

GGAAGATCAAAGTGTACTTACCTCGCATGAAGATGGAGGAAAAATACAACCTCACATCTGTCTT

AATGGCTATGGGCATTACTGACGTGTTTAGCTCTTCAGCCAATCTGTCTGGCATCTCCTCAGCA

GAGAGCCTGAAGATATCTCAAGCTGTCCATGCAGCACATGCAGAAATCAATGAAGCAGGCAGAG

AGGTGGTAGGGTCAGCAGAGGCTGGAGTGGATGCTGCAAGCGTCTCTGAAGAATTTAGGGCTGA

CCATCCATTCCTCTTCTGTATCAAGCACATCGCAACCAACGCCGTTCTCTTCTTTGGCAGATGT

GTTTCCCCTTAA
```

3'-UTR from OV Exon 8 - constructs 4 and 6, SEQ ID NO: 41
AAAGAAGAAAGCTGAAAAAC
Or Alternative 3'-UTR from OV Exon 8 - constructs 4 and 6, SEQ ID NO: 42
```
TCTGTCCCTTCCAACAAGACCCAGAGCACTGTAGTATCAGGGGTAAAATGAAAAGTATGTTATC

TGCTGCATCCAGACTTCATAAAAGCTGGAGCTTAATCTAGAAAAAAAATCAGAAAGAAATTACA

CTGTGAGAACAGGTGCAATTCACTTTTCCTTTACACAGAGTAATACTGGTAACTCATGGATGAA

GGCTTAAGGGAATGAAATTGGACTCACAGTACTGAGTCATCACACTGAAAAATGCAACCTGATA

CATCAGCAGAAGGTTTATGGGGGAAAAATGCAGCCTTCCAATTAAGCCAGATATCTGTATGACC

AAGCTGCTCCAGAATTAGTCACTCAAAATCTCTCAGATTAAATTATCAACTGTCACCAACCATT

CCTATGCTGACAAGGCAATTGCTTGTTCTCTGTGTTCCTGATACTACAAGGCTCTTCCTGACTT

CCTAAAGATGCATTATAAAAATCTTATAATTCACATTTCTCCCTAAACTTTGACTCAATCATGG

TATGTTGGCAAATATGGTATATTACTATTCAAATTGTTTTCCTTGTACCCATATGTAATGGGTC

TTGTGAATGTGCTCTTTTGTTCCTTTAATCATAATAAAAACATGTTTAAGC
```
Or

Alternate 3'-UTR from OV Exon 8 - constructs 4 and 6, SEQ ID NO: 43
```
AAAGAAGAAAGCTGAAAAACTCTGTCCCTTCCAACAAGACCCAGAGCACTGTAGTATCAGGGGT

AAAATGAAAAGTATGTTCTCTGCTGCATCCAGACTTCATAAAAGCTGGAGCTTAATCTAGAAAA

AAAATCAGAAAGAAATTACACTGTGAGAACAGGTGCAATTCACTTTTCCTTTACACAGAGTAAT

ACTGGTAACTCATGGATGAAGGCTTAAGGGAATGAAATTGGACTCACAGTACTGAGTCATCACA

CTGAAAAATGCAACCTGATACATCAGCAGAAGGTTTATGGGGGAAAAATGCAGCCTTCCAATTA

AGCCAGATATCTGTATGACCAAGCTCCTCCAGAATTAGTCACTCAAAATCTCTCAGATTAAATT

ATCAACTGTCACCAACTATTCCTATGCTGACAAGGCAATTGCTTGTTCTCTGTGTTCCTGATAC
```

-continued

TACAAGGCTCTTCCTGACTTCCTAAAGATGCATTATAAAAATCTTATAATTCACATTTCTCCCT

AAACTTTGACTCAATCATGGTATGTTGGCAAATATGGTATATTACTATTCAAATTGTTTTCCTT

GTACCCATATGTAATGGGTCTTGTGAATGTGCTCTTTTGTTCCTTTAATCATAATAAAAACATG

TTTAAGC

OV downstream flanking sequence - constructs 4 and 6, SEQ ID
NO: 44
AAACACTTTTCACTTGTAGTATTTGAAGTACAGCAAGGTTGTGTAGCAGGGAAAGAATGACATG

CAGAGGAATAAGTATGGACACACAGGCTAGCAGCGACTGTAGAACAAGTACTAATGGGTGAGAA

GTTGAACAAGAGTCCCCTACAGCAACTTAATCTAATAAGCTAGTGGTCTACATCAGCTAAAAGA

GCATAGTGAGGGATGAAATTGGTTCTCCTTTCTAAGCATCACCTGGGACAACTCATCTGGAGCA

GTGTGTCCAATCTGCCGCTGCCCTGATCCTGGCTGGGGTGATGGGACAGACCTTGGCTGCCACT

GAGACATCTGAGACACTGAGATCTGTCTCAACTCAGATTTACCCAAGAACAGATCATTGCCAAC

AGAACAAAATCTCAAACTTATGGCTAGTGATGACAGCAGTCAGTTGTCCCATCTGTGACCCACC

AAGGCTGGCATGCTGGAATGAGCAGGCTTTGGTGGCTTGTAGTTACTGGACAGCACCACTGACA

TGGGCAGGGGAAAAACTGAGCATGGTGTAAATCACTGCCTCAAAGCCACTTCTCTGTGCCTGCA

CCATGCTTGAAAGCTCTTCTACAGGAGCTGGGTTTGTTCAAGAAAGCTTCTGTTTCTCCCATCT

GCTTCTTGTACCTTCACAGGGACAGAGTTAGAAGGGTACAGCCATGG

GSG linker - constructs 1-3, SEQ ID NO: 45
TTGGATCCCTACCGGTGCTGCGGCCGCGCAGTTAAC

P2A - constructs 5 and 6, SEQ ID NO: 46
GCTACTAACTTCAGCCTGCTGAAGCAGGCTGGAGACGTGGAGGAGAACCCTGGACCT OV Construct 1hCECR1, SEQ ID NO: 47
AAAGTGCCACCTGACGTCGACGGTTATCCACAGAATCAGGGGATAACGCAGGAAAGAACATGTG

CGCATGCCTGCTATTGTCTTCCCAATCCTCCCCCTTGCTGTCCTGCCCCACCCCACCCCCCAGA

ATAGAATGACACCTACTCAGACAATGCGATGCAATTTCCTCATTTTATTAGGAAAGGACAGTGG

GAGTGGCACCTTCCAGGGTCAAGGAAGGCACGGGGGAGGGGCAAACAACAGATGGCTGGCAACT

AGAAGGCACAGTCGAGGCTGATCAGCGAGCTCTAGCATTTAGGTGACACTATAGAATAGGGCCC

TCTAGCGAATTAATTCAGGTTGTTAACAACAACAATTTTCGAAGGTACCTCAGGCACCGGGCTT

GCGGGTCATGCACCAGGTGCGCGGTCCTTCGGGCACCTCGACGTCGGCGGTGACGGTGAAGCCG

AGCCGCTCGTAG+AGGGGAGGTTGCGGGGCGCGGAGGTCTCCAGGAAGGCGGGCACCCCGGCGC

GCTCGGCCGCCTCCACTCCGGGGAGCACGACGGCGCTGCCCAGACCCTTGCCCTGGTGGTCGGG

CGAGACGCCGACGGTGGCCAGGAACCACGCGGGCTCCTTGGGCCGGTGCGGCGCCAGGAGGCCT

TCCATCTGTTGCTGCGCGGCCAGCCGGGAACCGCTCAACTCGGCCATGCGCGGGCCGATCTCGG

CGAACACCGCCCCGCTTCGACGCTCTCCGGCGTGGTCCAGACCGCCACCGCGGCGCCGTCGTC

CGCGACCCACACCTTGCCGATGTCGAGCCCGACGCGCGTGAGGAAGAGTTCTTGCAGCTCGGTG

ACCCGCTCGATGTGGCGGTCCGGGTCGACGGTGTGGCGCGTGGCGGGGTAGTCGGCGAACGCGG

CGGCGAGGGTGCGTACGGCCCGGGGGACGTCGTCGCGGGTGGCGAGGCGCACCGTGGGCTTGTA

CTCGGTCATGGTACCAGCTTTTTGCAAAAGCCTAGGCCTCCAAAAAAGCCTCCTCACTACTTCT

GGAATAGCTCAGAGGCAGAGGCGGCCTCGGCCTCTGCATAAATAAAAAAAATTAGTCAGCCATG

GGGCGGAGAATGGGCGGAACTGGGCGGAGTTAGGGGCGGGATGGGCGGAGTTAGGGGCGGGACT

ATGGTTGCTGACTAATTGAGATGCATGCTTTGCATACTTCTGCCTGCTGGGGAGCCTGGGGACT

TTCCACACCTGGTTGCTGACTAATTGAGATGCATGCTTTGCATACTTCTGCCTGCTGGGGAGCC

TGGGGACTTTCCACACCCTAACTGACACACATTCCACAGACATGTGAGCAAAAGGCCAGCAAAA

-continued

```
GGACTAGTTATTGATATCTATACACAAATTATTAGTGTTTGATTGACACCAGATGACAGAGAAG
TGCATCTGAGAAAACCTATTCCCAATCTCCTTTCTCTTTCTGCAGACTGACATGCATTTCATAG
GTAGAGATAACATTTACTGGGAAGCACATCTATCATCACAAAAAGCAGGCAAGATTTTCAGACT
TTCTTAGTGGCTGAAATAGAAGCAAAAGACGTGATTAAAAACAAAATGAAACAAAAAAAATCAG
TTGATACCTGTGGTGTAGACATCCAGCAAAAAAATATTATTTGCACTACCATCTTGTCTTAAGT
CCTCAGACTTGGCAAGGAGAATGTAGATTTCCACAGTATATATGTTTTCACAAAAGGAAGGAGA
GAAACAAAAGAAAATGGCACTGACTAAACTTCAGCTAGTGGTATAGGAAAGTAATTCTGCTTAA
CAGAGATTGCAGTGATCTCTATGTATGTCCTGAAGAATTATGTTGTACTTTTTTCCCCCATTTT
TAAATCAAACAGTGCTTTACAGAGGTCAGAATGGTTTCTTTACTGTTTGTCAATTCTATTATTT
CAATACAGAACAATAGCTTCTATAACTGAAATATATTTGCTATTGTATATTATGATTGTCCCTC
GAACCATGAACACTCCTCCAGCTGAATTTCACAATTCCTCTGTCATCTGCCAGGCCATTAAGTT
ATTCATGGAAGATCTTTGAGGAACACTGCAAGTTCATATCATAAACACATTTGAAATTGAGTAT
TGTTTTGCATTGTATGGAGCTATGTTTTGCTGTATCCTCAGAAAAAAGTTTGTTATAAAGCAT
TCACACCCATAAAAAGATAGATTTAAATATTCCAACTATAGGAAAGAAAGTGCGTCTGCTCTTC
ACTCTAGTCTCAGTTGGCTCCTTCACATGCACGCTTCTTTATTTCTCCTATTTTGTCAAGAAAA
TAATAGGTCACGTCTTGTTCTCACTTATGTCCTGCCTAGCATGGCTCAGATGCACGTTGTACAT
ACAAGAAGGATCAAATGAAACAGACTTCTGGTCTGTTACTACAACCATAGTAATAAGCACACTA
ACTAATAATTGCTAATTATGTTTTCCATCTCCAAGGTTCCCACATTTTTCTGTTTTCTTAAAGA
TCCCATTATCTGGTTGTAACTGAAGCTCAATGGAACATGAGCAATATTTCCCAGTCTTCTCTCC
CATCCAACAGTCCTGATGGATTAGCAGAACAGGCAGAAAACACATTGTTACCCAGAATTAAAAA
CTAATATTTGCTCTCCATTCAATCCAAAATGGACCTATTGAAACTAAAATCTAACCCAATCCCA
TTAAATGATTTCTATGGCGTCAAAGGTCAAACTTCTGAAGGGAACCTGTGGGTGGGTCACAATT
CAGGCTATATATTCCCCAGGGCTCAGCCAGTGTCTGTTTGGATCCCTACCGGTGCTGCGGCCGC
GCAGTTAACGAATTCGCCACCATGTTGGTGGATGGCCCATCTGAGCGGCCAGCCCTGTGCTTCT
TGCTGTTGGCTGTGGCAATGTCTTTCTTCGGCTCTGCTCTATCCATAGATGAAACACGGGCGCA
TCTGTTGTTGAAAGAAAAGATGATGCGGCTGGGGGGGCGGCTGGTGCTGAACACCAAGGAGGAG
CTGGCCAATGAGAGGCTCATGACGCTCAAAATCGCTGAGATGAAGGAGGCCATGAGGACCCTGA
TATTCCCACCCAGCATGCACTTTTTCCAGGCCAAGCATCTCATTGAGAGAAGTCAAGTGTTTAA
TATTCTAAGGATGATGCCAAAAGGGGCTGCCTTGCACCTCCATGACATTGGCATCGTGACTATG
GACTGGCTGGTGAGGAATGTCACCTACAGGCCTCACTGCCACATCTGTTTCACCCCAAGGGGGA
TCATGCAGTTCAGATTTGCTCACCCAACTCCCCGTCCATCAGAAAAATGTTCCAAGTGGATTCT
GCTGGAGGATTATCGGAAGCGGGTGCAGAACGTCACTGAGTTTGATGACAGCTTGCTGAGGAAT
TTCACTCTGGTGACCCAGCACCCGGAGGTGATTTACACAAACCAAATGTTCTCTGGTCGAAAT
TTGAAACCATCTTCTTCACCATCTCTGGTCTCATCCATTACGCTCCAGTGTTCAGAGACTATGT
CTTCCGGAGCATGCAGGAGTTCTACGAGGACAACGTGCTCTACATGGAGATCAGAGCCAGGCTG
CTGCCGGTGTATGAGCTCAGTGGAGAGCACCATGACGAAGAGTGGTCAGTGAAGACTTATCAGG
AAGTAGCTCAGAAGTTTGTGGAAACTCATCCTGAGTTTATTGGAATCAAAATCATTTATTCGGA
TCACAGATCCAAAGATGTGGCTGTCATCGCAGAATCCATCCGAATGGCCATGGGGCTCCGAATC
AAGTTCCCCACGGTGGTGGCAGGGTTTGACCTGGTGGGGCATGAGGACACTGGCCACTCCTTGC
ATGACTACAAGGAAGCTCTGATGATCCCCGCCAAGGATGGCGTTAAGCTGCCTTACTTCTTCCA
```

-continued
CGCCGGAGAAACAGACTGGCAGGGTACTTCCATAGACAGGAACATTCTGGATGCTCTGATGCTG

AACACTACCAGAATCGGCCATGGATTTGCTTTGAGCAAACACCCCGCAGTCAGGACTTATTCCT

GGAAAAAGGACATCCCCATAGAAGTCTGTCCCATCTCTAACCAGGTGCTGAAACTGGTGTCTGA

CTTGAGGAACCACCCTGTAGCCACTCTGATGGCCACTGGGCACCCCATGGTGATCAGCTCTGAT

GACCCAGCTATGTTTGGTGCCAAAGGCTTGTCCTATGATTTCTATGAGGTCTTCATGGGCATTG

GGGGGATGAAGGCTGATCTGAGGACCCTCAAACAGCTGGCCATGAACTCTATCAAGTACAGTAC

CCTGTTGGAGAGTGAGAAAAATACTTTCATGGAAATATGGAAGAAGAGATGGGATAAGTTCATA

GCAGATGTGGCTACAAAGTGAAGATCTTTGGATCCCTACCGGTGCTGCGGCCGCGCAGTTAACG

CCGCCCCTCTCCCTCCCCCCCCCCTAACGTTACTGGCCGAAGCCGCTTGGAATAAGGCCGGTGT

GCGTTTGTCTATATGTTATTTTCCACCATATTGCCGTCTTTTGGCAATGTGAGGGCCCGGAAAC

CTGGCCCTGTCTTCTTGACGAGCATTCCTAGGGGTCTTTCCCCTCTCGCCAAAGGAATGCAAGG

TCTGTTGAATGTCGTGAAGGAAGCAGTTCCTCTGGAAGCTTCTTGAAGACAAACAACGTCTGTA

GCGACCCTTTGCAGGCAGCGGAACCCCCCACCTGGCGACAGGTGCCTCTGCGGCCAAAAGCCAC

GTGTATAAGATACACCTGCAAAGGCGGCACAACCCCAGTGCCACGTTGTGAGTTGGATAGTTGT

GGAAAGAGTCAAATGGCTCTCCTCAAGCGTATTCAACAAGGGGCTGAAGGATGCCCAGAAGGTA

CCCCATTGTATGGGATCTGATCTGGGGCCTCGGTACACATGCTTTACATGTGTTTAGTCGAGGT

TAAAAAAACGTCTAGGCCCCCGAACCACGGGGACGTGGTTTTCCTTTGAAAAACACGATGATA

ATATGGCCACAACATACAGCTAGAAAGCTGTATTGCCTTTAGCACTCAAGCTCAAAAGGTAAGC

AACTCTCTGGAATTACCTTCTCTATATTAGCTCTTACTTGCACCTAAACTTTAAAAAATTAA

CAATTATTGTGTTATGTGTTGTATCTTTAAGGGTGAAGTACCTGCGTGATACCCCCTATAAAAA

CTTCTCACCTGTGTATGCATTCTGCACTATTTTATTATGTGTAAAAGCTTTGTGTTTGTTTTCA

GGAGGCTTATTCTTTGTGCTTAAAATATGTTTTTAATTTCAGAACATCTTATCCTGTCGTTCAC

TATCTGATATGCTTTGCAGTTTGCTTGATTAACTTCTAGCCCTACAGAGTGCACAGAGAGCAAA

ATCATGGTGTTCAGTGAATTCTGGGGAGTTATTTTAATGTGAAAATTCTCTAGAAGTTTAATTC

CTGCAAAGTGCAGCTGCTGATCACTACACAAGATAAAAATGTGGGGGGTGCATAAACGTATATT

CTTACAATAATAGATACATGTGAACTTGTATACAGAAAAGAAAATGAGAAAAATGTGTGTGCGT

ATACTCACACACGTGGTCAGTAAAAACTTTTGAGGGGTTTAATACAGAAAATCCAATCCTGAGG

CCCCAGCACTCAGTACGCATATAAAGGGCTGGGCTCTGAAGGACTTCTGACTTTCACAGATTAT

ATAAATCTCAGGAAAGCAACTAGATTCATGCTGGCTCCAAAAGCTGTGCTTTATATAAGCACAC

TGGCTATACAATAGTTGTACAGTTCAGCTCTTTATAATAGAAACAGACAGAACAAGTATAAATC

TTCTATTGGTCTATGTCATGAACAAGAATTCATTCAGTGGCTCTGTTTTATAGTAAACATTGCT

ATTTTATCATGTCTGCATTTCTCTTCTGTCTGAATGTCACCACTAAAATTTAACTCCACAGAAA

GTTTATACTACAGTACACATGCATATCTTTGAGCAAAGCAAACCATACCTGAAAGTGCAATAGA

GCAGAATATGAATTACATGCGTGTCTTTCTCCTAGACTACATGACCCCATATAAATTACATTCC

TTATCTATTCTGCCATCACCAAAACAAAGGTAAAAATACTTTTGAAGATCTACTCATAGCAAGT

AGTGTGCAACAAACAGATATTTCTCTACATTTATTTTTAGGGAATAAAAATAAGAAATAAAATA

GTCAGCAAGCCTCTGCTTTCTCATATATCTGTCCAAACCTAAAGTTTACTGAAATTTGCTCTTT

GAATTTCCAGTTTTGCAAGCCTATCAGATTGTGTTTAATCAGAGGTACTGAAAAGTATCAATG

AATTCTGATATCGTCGTGCCAGCTGCATTAATGAATCGGCCAACGCGCGGGGAGAGGCGGTTTG

CGTATTGGGCGCTCTTCCGCTTCCTCGCTCACTGACTCGCTGCGCTCGGTCGTTCGGCTGCGG

GAGCGGTATCAGCTCACTCAAAGGCGGTAATACGGTTATCCACAGAATCAGGGGATAACGCAGG

-continued

```
AAAGAACATGTGAGCAAAAGGCCAGCAAAAGGCCAGGAACCGTAAAAAGGCCGCGTTGCTGGCG

TTTTTCCATAGGCTCCGCCCCCCTGACGAGCATCACAAAAATCGATGCTCAAGTCAGAGGTGGC

GAAACCCGACAGGACTATAAAGATACCAGGCGTTTCCCCCTGGAAGCTCCCTCGTGCGCTCTCC

TGTTCCGACCCTGCCGCTTACCGGATACCTGTCCGCCTTTCTCCCTTCGGGAAGCGTGGCGCTT

TCTCATAGCTCACGCTGTAGGTATCTCAGTTCGGTGTAGGTCGTTCGCTCCAAGCTGGGCTGTG

TGCACGAACCCCCCGTTCAGCCCGACCGCTGCGCCTTATCCGGTAACTATCGTCTTGAGTCCAA

CCCGGTAAGACACGACTTATCGCCACTGGCAGCAGCCACTGGTAACAGGATTAGCAGAGCGAGG

TATGTAGGCGGTGCTACAGAGTTCTTGAAGTGGTGGCCTAACTACGGCTACACTAGAAGAACAG

TATTTGGTATCTGCGCTCTGCTGAAGCCAGTTACCTTCGGAAAAAGAGTTGGTAGCTCTTGATC

CGGCAAACAAACCACCGCTGGTAGCGGTGGTTTTTTTGTTTGCAAGCAGCAGATTACGCGCAGA

AAAAAAGGATCTCAAGAAGATCCTTTGATCTTTTCTACGGGGTCTGACGCTCAGTGGAACGAAA

ACTCACGTTAAGGGATTTTGGTCATGAGATTATCAAAAAGGATCTTCACCTAGATCCTTTTAAA

TTAAAAATGAAGTTTTAAATCAATCTAAAGTATATATGAGTAAACTTGGTCTGACAGTTACCAA

TGCTTAATCAGTGAGGCACCTATCTCAGCGATCTGTCTATTTCGTTCATCCATAGTTGCCTGAC

TCCCCGTCGTGTAGATAACTACGATACGGGAGGGCTTACCATCTGGCCCCAGTGCTGCAATGAT

ACCGCGAGACCCACGCTCACCGGCTCCAGATTTATCAGCAATAAACCAGCCAGCCGGAAGGGCC

GAGCGCAGAAGTGGTCCTGCAACTTTATCCGCCTCCATCCAGTCTATTAATTGTTGCCGGGAAG

CTAGAGTAAGTAGTTCGCCAGTTAATAGTTTGCGCAACGTTGTTGCCATTGCTACAGGCATCGT

GGTGTCACGCTCGTCGTTTGGTATGGCTTCATTCAGCTCCGGTTCCCAACGATCAAGGCGAGTT

ACATGATCCCCCATGTTGTGCAAAAAAGCGGTTAGCTCCTTCGGTCCTCCGATCGTTGTCAGAA

GTAAGTTGGCCGCAGTGTTATCACTCATGGTTATGGCAGCACTGCATAATTCTCTTACTGTCAT

GCCATCCGTAAGATGCTTTTCTGTGACTGGTGAGTACTCAACCAAGTCATTCTGAGAATAGTGT

ATGCGGCGACCGAGTTGCTCTTGCCCGGCGTCAATACGGGATAATACCGCGCCACATAGCAGAA

CTTTAAAAGTGCTCATCATTGGAAAACGTTCTTCGGGGCGAAAACTCTCAAGGATCTTACCGCT

GTTGAGATCCAGTTCGATGTAACCCACTCGTGCACCCAACTGATCTTCAGCATCTTTTACTTTC

ACCAGCGTTTCTGGGTGAGCAAAAACAGGAAGGCAAAATGCCGCAAAAAAGGGAATAAGGGCGA

CACGGAAATGTTGAATACTCATACTCTTCCTTTTTCAATATTATTGAAGCATTTATCAGGGTTA

TTGTCTCATGAGCGGATACATATTTGAATGTATTTAGAAAAATAAACAAATAGGGGTTCCGCGC

ACATTTCCCCGA
```
----------------

OV Construct 2 hCECR1, SEQ ID NO: 48

```
AAAGTGCCACCTGACGTCGACGGTTATCCACAGAATCAGGGGATAACGCAGGAAAGAACATGTG

CGCATGCCTGCTATTGTCTTCCCAATCCTCCCCCTTGCTGTCCTGCCCCACCCCACCCCCCAGA

ATAGAATGACACCTACTCAGACAATGCGATGCAATTTCCTCATTTTATTAGGAAAGGACAGTGG

GAGTGGCACCTTCCAGGGTCAAGGAAGGCACGGGGAGGGGCAAACAACAGATGGCTGGCAACT

AGAAGGCACAGTCGAGGCTGATCAGCGAGCTCTAGCATTTAGGTGACACTATAGAATAGGGCCC

TCTAGCGAATTAATTCAGGTTGTTAACAACAACAATTTTCGAAGGTACCTCAGGCACCGGGCTT

GCGGGTCATGCACCAGGTGCGCGGTCCTTCGGGCACCTCGACGTCGGCGGTGACGGTGAAGCCG

AGCCGCTCGTAGAAGGGGAGGTTGCGGGGCGCGGAGGTCTCCAGGAAGGCGGGCACCCCGGCGC

GCTCGGCCGCCTCCACTCCGGGGAGCACGACGGCGCTGCCCAGACCCTTGCCCTGGTGGTCGGG

CGAGACGCCGACGGTGGCCAGGAACCACGCGGGCTCCTTGGGCCGGTGCGGCGCCAGGAGGCCT
```

-continued

```
TCCATCTGTTGCTGCGCGGCCAGCCGGGAACCGCTCAACTCGGCCATGCGCGGGCCGATCTCGG

CGAACACCGCCCCCGCTTCGACGCTCTCCGGCGTGGTCCAGACCGCCACCGCGGCGCCGTCGTC

CGCGACCCACACCTTGCCGATGTCGAGCCCGACGCGCGTGAGGAAGAGTTCTTGCAGCTCGGTG

ACCCGCTCGATGTGGCGGTCCGGGTCGACGGTGTGGCGCGTGGCGGGGTAGTCGGCGAACGCGG

CGGCGAGGGTGCGTACGGCCCGGGGGACGTCGTCGCGGGTGGCGAGGCGCACCGTGGGCTTGTA

CTCGGTCATGGTACCAGCTTTTTGCAAAAGCCTAGGCCTCCAAAAAAGCCTCCTCACTACTTCT

GGAATAGCTCAGAGGCAGAGGCGGCCTCGGCCTCTGCATAAATAAAAAAAATTAGTCAGCCATG

GGGCGGAGAATGGGCGGAACTGGGCGGAGTTAGGGGCGGGATGGGCGGAGTTAGGGGCGGGACT

ATGGTTGCTGACTAATTGAGATGCATGCTTTGCATACTTCTGCCTGCTGGGGAGCCTGGGGACT

TTCCACACCTGGTTGCTGACTAATTGAGATGCATGCTTTGCATACTTCTGCCTGCTGGGGAGCC

TGGGGACTTTCCACACCCTAACTGACACACATTCCACAGACATGTGAGCAAAAGGCCAGCAAAA

GGACTAGTTATTGATATCAGTACCTGCGTGATACCCCCTATAAAAACTTCTCACCTGTGTATGC

ATTCTGCACTATTTTATTATGTGTAAAAGCTTTGTGTTTGTTTTCAGGAGGCTTATTCTTTGTG

CTTAAAATATGTTTTTAATTTCAGAACATCTTATCCTGTCGTTCACTATCTGATATGCTTTGCA

GTTTGCTTGATTAACTTCTAGCCCTACAGAGTGCACAGAGAGCAAAATCATGGTGTTCAGTGAA

TTCTGGGGAGTTATTTTAATGTGAAAATTCTCTAGAAGTTTAATTCCTGCAAAGTGCAGCTGCT

GATCACTACACAAGATAAAAATGTGGGGGGTGCATAAACGTATATTCTTACAATAATAGATACA

TGTGAACTTGTATACAGAAAAGAAAATGAGAAAAATGTGTGTGCGTATACTCACACACGTGGTC

AGTAAAAACTTTTGAGGGGTTTAATACAGAAAATCCAATCCTGAGGCCCCAGCACTCAGTACGC

ATATAAAGGGCTGGGCTCTGAAGGACTTCTGACTTTCACAGATTATATAAATCTCAGGAAAGCA

ACTAGATTCATGCTGGCTCCAAAAGCTGTGCTTTATATAAGCACACTGGCTATACAATAGTTGT

ACAGTTCAGCTCTTTATAATAGAAACAGACAGAACAAGTATAAATCTTCTATTGGTCTATGTCA

TGAACAAGAATTCATTCAGTGGCTCTGTTTTATAGTAAACATTGCTATTTTATCATGTCTGCAT

TTCTCTTCTGTCTGAATGTCACCACTAAAATTTAACTCCACAGAAAGTTTATACTACAGTACAC

ATGCATATCTTTGAGCAAAGCAAACCATACCTGAAAGTGCAATAGAGCAGAATATGAATTACAT

GCGTGTCTTTCTCCTAGACTACATGACCCCATATAAATTACATTCCTTATCTATTCTGCCATCA

CCAAAACAAAGGTAAAAATACTTTTGAAGATCTACTCATAGCAAGTAGTGTGCAACAAACAGAT

ATTTCTCTACATTTATTTTAGGGAATAAAAATAAGAAATAAAATAGTCAGCAAGCCTCTGCTT

TCTCATATATCTGTCCAAACCTAAAGTTTACTGAAATTTGCTCTTTGAATTTCCAGTTTTGCAA

GCCTATCAGATTGTGTTTTAATCAGAGGTACTGAAAAGTATCAATGAATTCTAGCTTTCACTGA

ACAAAAATATGTAGAGGCAACTGGCTTCTGGGACAGTTTGCTACCCAAAAGACAACTGAATGCA

AATACATAAATAGATTTATGAATATGGTTTTGAACATGCACATGAGAGGTGGATATAGCAACAG

ACACATTACCACAGAATTACTTTAAAACTACTTGTTAACATTTAATTGCCTAAAAACTGCTCGT

AATTTACTGTTGTAGCCTACCATAGAGTACCCTGCATGGTACTATGTACAGCATTCCATCCTTA

CATTTTCACTGTTCTGCTGTTTGCTCTAGACAACTCAGAGTTCACCATGTTGGTGGATGGCCCA

TCTGAGCGGCCAGCCCTGTGCTTCTTGCTGTTGGCTGTGGCAATGTCTTTCTTCGGCTCTGCTC

TATCCATAGATGAAACACGGGCGCATCTGTTGTTGAAAGAAAAGATGATGCGGCTGGGGGGGCG

GCTGGTGCTGAACACCAAGGAGGAGCTGGCCAATGAGAGGCTCATGACGCTCAAAATCGCTGAG

ATGAAGGAGGCCATGAGGACCCTGATATTCCCACCCAGCATGCACTTTTTCCAGGCCAAGCATC

TCATTGAGAAGTCAAGTGTTTAATATTCTAAGGATGATGCCAAAAGGGGCTGCCTTGCACCT

CCATGACATTGGCATCGTGACTATGGACTGGCTGGTGAGGAATGTCACCTACAGGCCTCACTGC
```

-continued

```
CACATCTGTTTCACCCCAAGGGGGATCATGCAGTTCAGATTTGCTCACCCAACTCCCCGTCCAT
CAGAAAAATGTTCCAAGTGGATTCTGCTGGAGGATTATCGGAAGCGGGTGCAGAACGTCACTGA
GTTTGATGACAGCTTGCTGAGGAATTTCACTCTGGTGACCCAGCACCCGGAGGTGATTTACACA
AACCAAAATGTTGTCTGGTCGAAATTTGAAACCATCTTCTTCACCATCTCTGGTCTCATCCATT
ACGCTCCAGTGTTCAGAGACTATGTCTTCCGGAGCATGCAGGAGTTCTACGAGGACAACGTGCT
CTACATGGAGATCAGAGCCAGGCTGCTGCCGGTGTATGAGCTCAGTGGAGAGCACCATGACGAA
GAGTGGTCAGTGAAGACTTATCAGGAAGTAGCTCAGAAGTTTGTGGAAACTCATCCTGAGTTTA
TTGGAATCAAAATCATTTATTCGGATCACAGATCCAAAGATGTGGCTGTCATCGCAGAATCCAT
CCGAATGGCCATGGGCTCCGAATCAAGTTCCCCACGGTGGTGGCAGGGTTTGACCTGGTGGGG
CATGAGGACACTGGCCACTCCTTGCATGACTACAAGGAAGCTCTGATGATCCCCGCCAAGGATG
GCGTTAAGCTGCCTTACTTCTTCCACGCCGGAGAAACAGACTGGCAGGGTACTTCCATAGACAG
GAACATTCTGGATGCTCTGATGCTGAACACTACCAGAATCGGCCATGGATTTGCTTTGAGCAAA
CACCCCGCAGTCAGGACTTATTCCTGGAAAAAGGACATCCCCATAGAAGTCTGTCCCATCTCTA
ACCAGGTGCTGAAACTGGTGTCTGACTTGAGGAACCACCCTGTAGCCACTCTGATGGCCACTGG
GCACCCCATGGTGATCAGCTCTGATGACCCAGCTATGTTTGGTGCCAAAGGCTTGTCCTATGAT
TTCTATGAGGTCTTCATGGGCATTGGGGGATGAAGGCTGATCTGAGGACCCTCAAACAGCTGG
CCATGAACTCTATCAAGTACAGTACCCTGTTGGAGAGTGAGAAAAATACTTTCATGGAAATATG
GAAGAAGAGATGGGATAAGTTCATAGCAGATGTGGCTACAAAGTGAAGATCTTTGGATCCCTAC
CGGTGCTGCGGCCGCGCAGTTAACGCCGCCCCTCTCCCTCCCCCCCCCCTAACGTTACTGGCCG
AAGCCGCTTGGAATAAGGCCGGTGTGCGTTTGTCTATATGTTATTTTCCACCATATTGCCGTCT
TTTGGCAATGTGAGGGCCCGGAAACCTGGCCCTGTCTTCTTGACGAGCATTCCTAGGGGTCTTT
CCCCTCTCGCCAAAGGAATGCAAGGTCTGTTGAATGTCGTGAAGGAAGCAGTTCCTCTGGAAGC
TTCTTGAAGACAAACAACGTCTGTAGCGACCCTTTGCAGGCAGCGGAACCCCCCACCTGGCGAC
AGGTGCCTCTGCGGCCAAAAGCCACGTGTATAAGATACACCTGCAAAGGCGGCACAACCCCAGT
GCCACGTTGTGAGTTGGATAGTTGTGGAAAGAGTCAAATGGCTCTCCTCAAGCGTATTCAACAA
GGGGCTGAAGGATGCCCAGAAGGTACCCCATTGTATGGGATCTGATCTGGGGCCTCGGTACACA
TGCTTTACATGTGTTTAGTCGAGGTTAAAAAAACGTCTAGGCCCCCCGAACCACGGGGACGTGG
TTTTCCTTTGAAAAACACGATGATAATATGGCCACATCAGAGTTCACCATGGGCTCCATCGGTG
CAGCAAGCATGGAATTTTGTTTTGATGTATTCAAGGAGCTCAAAGTCCACCATGCCAATGAGAA
CATCTTCTACTGCCCCATTGCCATCATGTCAGCTCTAGCCATGGTATACCTGGGTGCAAAAGAC
AGCACCAGGACACAAATAAATAAGGTGAGCCTACAGTTAAAGATTAAAACCTTTGCCCTGCTCA
ATGGAGCCACAGCACTTAATTGTATGATAATGTCCCTTGGAAACTGCATAGCTCAGAGGCTGAA
AATCTGAAACCAGAGTTATCTAAAAGTGTGGCCACCTCCAACTCCCAGAGTGTTACCCAAATGC
ACTAGCTAGAAATCTTGAAACTGGATTGCATAACTTCTTTTTGTCATAACCATTATTTCAGCTA
CTATTATTTTCAATTACAGGTTGTTCGCTTTGATAAACTTCCAGGATTCGGAGACAGTATTGAA
GCTCAGGTACAGAAATAATTTCACCTCCTTCTCTATGTCCCTTTCCTCTGGAAGCAAAATACAG
CAGATGAAGCAATCTCTTAGCTGTTCCAAGCCCTCTCTGATGAGCAGCTAGTGCTCTGCATCCA
GCAGTTGGGAGAACACTGTTCATAAGAACAGAGAAAAGAAGGAAGTAACAGGGGATTCAGAAC
AAACAGAAGATAAAACTCAGGACAAAAATACCGTGTGAATGAGGAAACTTGTGGATATTGTAC
GCTTAAGCAAGACAGCTAGATGATTCTGGATAAATGGGTCTGGTTGGAAAAGAAGGAAAGCCTG
```

-continued

```
GCTGATCTGCTGGAGCTAGATTATTGCAGCAGGTAGGCAGGAGTTCCCTAGAGAAAAGTATGAG

GGAATTACAGAAGAAAAACAGCACAAAATTGTAAATATTGGAAAAGGACCACATCAGTGTAGTT

ACTAGCAGTAAGACAGACAGGATGAAAAATAGTTTTGTAAACAGAAGTATCTAACTACTTTACT

CTGTTCATACACTACGTAAAACCTACTAAGTAATAAAACTAGAATAACAACATCTTTCTTTCTC

TTTGTATTCAGTGTGGCACATCTGTAAACGTTCACTCTTCACTTAGAGACATCCTCAACCAAAT

CACCAAACCAAATGATGTTTATTCGTTCAGCCTTGCCAGTAGACTTTATGCTGAAGAGAGATAC

CCAATCCTGCCAGTAAGTTGCTCTAAAATCTGATCTGAGTGTATTTCCATGCCAAAGCTCTACC

ATTCTGTAATGCAAAAACAGTCAGAGTTCCACATGTTTCACTAAGAAAATTTCTTTTTCTCTTG

TTTTTACAAATGAAAGAGAGGACAAATAACATTTCTCTATCACCGACCTGAAACTCTACAGTCT

TCAGAGAATGAATGGCTTGCTAAAAGAATGTCAAATCTTACCATACAGCTATTTCATATTACAC

TACTAAATACACTATAAGGCATAGCATGTAGTAATACAGTGTAAAATAGCTTTTTACACTACTA

GATATCGTCGTGCCAGCTGCATTAATGAATCGGCCAACGCGCGGGGAGAGGCGGTTTGCGTATT

GGGCGCTCTTCCGCTTCCTCGCTCACTGACTCGCTGCGCTCGGTCGTTCGGCTGCGGCGAGCGG

TATCAGCTCACTCAAAGGCGGTAATACGGTTATCCACAGAATCAGGGGATAACGCAGGAAAGAA

CATGTGAGCAAAAGGCCAGCAAAAGGCCAGGAACCGTAAAAAGGCCGCGTTGCTGGCGTTTTTC

CATAGGCTCCGCCCCCCTGACGAGCATCACAAAAATCGATGCTCAAGTCAGAGGTGGCGAAACC

CGACAGGACTATAAAGATACCAGGCGTTTCCCCCTGGAAGCTCCCTCGTGCGCTCTCCTGTTCC

GACCCTGCCGCTTACCGGATACCTGTCCGCCTTTCTCCCTTCGGGAAGCGTGGCGCTTTCTCAT

AGCTCACGCTGTAGGTATCTCAGTTCGGTGTAGGTCGTTCGCTCCAAGCTGGGCTGTGTGCACG

AACCCCCCGTTCAGCCCGACCGCTGCGCCTTATCCGGTAACTATCGTCTTGAGTCCAACCCGGT

AAGACACGACTTATCGCCACTGGCAGCAGCCACTGGTAACAGGATTAGCAGAGCGAGGTATGTA

GGCGGTGCTACAGAGTTCTTGAAGTGGTGGCCTAACTACGGCTACACTAGAAGAACAGTATTTG

GTATCTGCGCTCTGCTGAAGCCAGTTACCTTCGGAAAAAGAGTTGGTAGCTCTTGATCCGGCAA

ACAAACCACCGCTGGTAGCGGTGGTTTTTTTGTTTGCAAGCAGCAGATTACGCGCAGAAAAAAA

GGATCTCAAGAAGATCCTTTGATCTTTTCTACGGGGTCTGACGCTCAGTGGAACGAAAACTCAC

GTTAAGGGATTTTGGTCATGAGATTATCAAAAAGGATCTTCACCTAGATCCTTTTAAATTAAAA

ATGAAGTTTTAAATCAATCTAAAGTATATATGAGTAAACTTGGTCTGACAGTTACCAATGCTTA

ATCAGTGAGGCACCTATCTCAGCGATCTGTCTATTTCGTTCATCCATAGTTGCCTGACTCCCCG

TCGTGTAGATAACTACGATACGGGAGGGCTTACCATCTGGCCCCAGTGCTGCAATGATACCGCG

AGACCCACGCTCACCGGCTCCAGATTTATCAGCAATAAACCAGCCAGCCGGAAGGGCCGAGCGC

AGAAGTGGTCCTGCAACTTTATCCGCCTCCATCCAGTCTATTAATTGTTGCCGGGAAGCTAGAG

TAAGTAGTTCGCCAGTTAATAGTTTGCGCAACGTTGTTGCCATTGCTACAGGCATCGTGGTGTC

ACGCTCGTCGTTTGGTATGGCTTCATTCAGCTCCGGTTCCCAACGATCAAGGCGAGTTACATGA

TCCCCCATGTTGTGCAAAAAAGCGGTTAGCTCCTTCGGTCCTCCGATCGTTGTCAGAAGTAAGT

TGGCCGCAGTGTTATCACTCATGGTTATGGCAGCACTGCATAATTCTCTTACTGTCATGCCATC

CGTAAGATGCTTTTCTGTGACTGGTGAGTACTCAACCAAGTCATTCTGAGAATAGTGTATGCGG

CGACCGAGTTGCTCTTGCCCGGCGTCAATACGGGATAATACCGCGCCACATAGCAGAACTTTAA

AAGTGCTCATCATTGGAAAACGTTCTTCGGGGCGAAAACTCTCAAGGATCTTACCGCTGTTGAG

ATCCAGTTCGATGTAACCCACTCGTGCACCCAACTGATCTTCAGCATCTTTTACTTTCACCAGC
```

-continued

GTTTCTGGGTGAGCAAAAACAGGAAGGCAAATGCCGCAAAAAAGGGAATAAGGGCGACACGGA

AATGTTGAATACTCATACTCTTCCTTTTTCAATATTATTGAAGCATTTATCAGGGTTATTGTCT

CATGAGCGGATACATATTTGAATGTATTTAGAAAAATAAACAATAGGGGTTCCGCGCACATTT

CCCCGA

---

OV Construct 3 hCECR1, SEQ ID NO: 49

AAAGTGCCACCTGACGTCGACGGTTATCCACAGAATCAGGGGATAACGCAGGAAAGAACATGTG

CGCATGCCTGCTATTGTCTTCCCAATCCTCCCCCTTGCTGTCCTGCCCCACCCCACCCCCCAGA

ATAGAATGACACCTACTCAGACAATGCGATGCAATTTCCTCATTTTATTAGGAAAGGACAGTGG

GAGTGGCACCTTCCAGGGTCAAGGAAGGCACGGGGGAGGGGCAAACAACAGATGGGTGGCAACT

AGAAGGCACAGTCGAGGCTGATCAGCGAGCTCTAGCATTTAGGTGACACTATAGAATAGGGCCC

TCTAGCGAATTAATTCAGGTTGTTAACAACAACAATTTTCGAAGGTACCTCAGGCACCGGGCTT

GCGGGTCATGCACCAGGTGCGCGGTCCTTCGGGCACCTCGACGTCGGCGGTGACGGTGAAGCCG

AGCCGCTCGTAGAAGGGGAGGTTGCGGGGCGCGGAGGTCTCCAGGAAGGCGGGCACCCCGGCGC

GCTCGGCCGCCTCCACTCCGGGGAGCACGACGGCGCTGCCCAGACCCTTGCCCTGGTGGTCGGG

CGAGACGCCGACGGTGGCCAGGAACCACGCGGGCTCCTTGGGCCGGTGCGGCGCCAGGAGGCCT

TCCATCTGTTGCTGCGCGGGCAGCCGGGAACCGCTCAACTCGGCCATGCGCGGGCCGATCTCGG

CGAACACCGCCCCCGCTTCGACGCTCTCCGGCGTGGTCCAGACCGCCACCGCGGCGCCGTCGTC

CGCGACCCACACCTTGCCGATGTCGAGCCCGACGCGCGTGAGGAAGAGTTCTTGCAGCTCGGTG

ACCCGCTCGATGTGGCGGTCCGGGTCGACGGTGTGGCGCGTGGCGGGGTAGTCGGCGAACGCGG

CGGCGAGGGTGCGTACGGCCCGGGGGACGTCGTCGCGGGTGGCGAGGCGCACCGTGGGCTTGTA

CTCGGTCATGGTACCAGCTTTTTGCAAAAGCCTAGGCCTCCAAAAAAGCCTCCTCACTACTTCT

GGAATAGCTCAGAGGCAGAGGCGGCCTCGGCCTCTGCATAAATAAAAAAAATTAGTCAGCCATG

GGGCGGAGAATGGGCGGAACTGGGCGGAGTTAGGGGCGGGATGGGCGGAGTTAGGGGCGGGACT

ATGGTTGCTGACTAATTGAGATGCATGCTTTGCATACTTCTGCCTGCTGGGGAGCCTGGGGACT

TTCCACACCTGGTTGCTGACTAATTGAGATGCATGCTTTGCATACTTCTGCCTGCTGGGGAGCC

TGGGGACTTTCCACACCCTAACTGACACACATTCCACAGACATGTGAGCAAAAGGCCAGCAAAA

GGACTAGTTATTGATATCTATACACAAATTATTAGTGTTTGATTGACACCAGATGACAGAGAAG

TGCATCTGAGAAAACCTATTCCCAATCTCCTTTCTCTTTCTGCAGACTGACATGCATTTCATAG

GTAGAGATAACATTTACTGGGAAGCACATCTATCATCACAAAAAGCAGGCAAGATTTTCAGACT

TTCTTAGTGGCTGAAATAGAAGCAAAAGACGTGATTAAAAACAAAATGAAACAAAAAAATCAG

TTGATACCTGTGGTGTAGACATCCAGCAAAAAAATATTATTTGCACTACCATCTTGTCTTAAGT

CCTCAGACTTGGCAAGGAGAATGTAGATTTCCACAGTATATATGTTTTCACAAAAGGAAGGAGA

GAAACAAAAGAAAATGGCACTGACTAAACTTCAGCTAGTGGTATAGGAAAGTAATTCTGCTTAA

CAGAGATTGCAGTGATCTCTATGTATGTCCTGAAGAATTATGTTGTACTTTTTTCCCCATTTT

TAAATCAAACAGTGCTTTACAGAGGTCAGAATGGTTTCTTTACTGTTTGTCAATTCTATTATTT

CAATACAGAACAATAGCTTCTATAACTGAAATATATTTGCTATTGTATATTATGATTGTCCCTC

GAACCATGAACACTCCTCCAGCTGAATTTCACAATTCCTCTGTCATCTGCCAGGCCATTAAGTT

ATTCATGGAAGATCTTTGAGGAACACTGCAAGTTCATATCATAAACACATTTGAAATTGAGTAT

TGTTTTGCATTGTATGGAGCTATGTTTTGCTGTATCCTCAGAAAAAAGTTTGTTATAAAGCAT

TCACACCCATAAAAAGATAGATTTAAATATTCCAACTATAGGAAAGAAAGTGCGTCTGCTCTTC

ACTCTAGTCTCAGTTGGCTCCTTCACATGCACGCTTCTTTATTTCTCCTATTTTGTCAAGAAAA

-continued

```
TAATAGGTCACGTCTTGTTCTCACTTATGTCCTGCCTAGCATGGCTCAGATGCACGTTGTACAT
ACAAGAAGGATCAAATGAAACAGACTTCTGGTCTGTTACTACAACCATAGTAATAAGCACACTA
ACTAATAATTGCTAATTATGTTTTCCATCTCCAAGGTTCCCACATTTTTCTGTTTTCTTAAAGA
TCCCATTATCTGGTTGTAACTGAAGCTCAATGGAACATGAGCAATATTTCCCAGTCTTCTCTCC
CATCCAACAGTCCTGATGGATTAGCAGAACAGGCAGAAAACACATTGTTACCCAGAATTAAAAA
CTAATATTTGCTCTCCATTCAATCCAAATGGACCTATTGAAACTAAAATCTAACCCAATCCCA
TTAAATGATTTCTATGGCGTCAAAGGTCAAACTTCTGAAGGGAACCTGTGGGTGGGTCACAATT
CAGGCTATATATTCCCCAGGGCTCAGCCAGTGTCTGTACATACAGCTAGAAAGCTGTATTGCCT
TTAGCACTCAAGCTCAAAAGACAACTCAGAGTTCACCATGTTGGTGGATGGCCCATCTGAGCGG
CCAGCCCTGTGCTTCTTGCTGTTGGCTGTGGCAATGTCTTTCTTCGGCTCTGCTCTATCCATAG
ATGAAACACGGGCGCATCTGTTGTTGAAAGAAAGATGATGCGGCTGGGGGGCGGCTGGTGCT
GAACACCAAGGAGGAGCTGGCCAATGAGAGGCTCATGACGCTCAAAATCGCTGAGATGAAGGAG
GCCATGAGGACCCTGATATTCCCACCCAGCATGCACTTTTTCCAGGCCAAGCATCTCATTGAGA
GAAGTCAAGTGTTTAATATTCTAAGGATGATGCCAAAAGGGGCTGCCTTGCACCTCCATGACAT
TGGCATCGTGACTATGGACTGGCTGGTGAGGAATGTCACCTACAGGCCTCACTGCCACATCTGT
TTCACCCCAAGGGGGATCATGCAGTTCAGATTTGCTCACCCAACTCCCCGTCCATCAGAAAAAT
GTTCCAAGTGGATTCTGCTGGAGGATTATCGGAAGCGGGTGCAGAACGTCACTGAGTTTGATGA
CAGCTTGCTGAGGAATTTCACTCTGGTGACCCAGCACCCGGAGGTGATTTACACAAACCAAAAT
GTTGTCTGGTCGAAATTTGAAACCATCTTCTTCACCATCTCTGGTCTCATCCATTACGCTCCAG
TGTTCAGAGACTATGTCTTCCGGAGCATGCAGGAGTTCTACGAGGACAACGTGCTCTACATGGA
GATCAGAGCCAGGCTGCTGCCGGTGTATGAGCTCAGTGGAGAGCACCATGACGAAGAGTGGTCA
GTGAAGACTTATCAGGAAGTAGCTCAGAAGTTTGTGGAAACTCATCCTGAGTTTATTGGAATCA
AAATCATTTATTCGGATCACAGATCCAAAGATGTGGCTGTCATCGCAGAATCCATCCGAATGGC
CATGGGCTCCGAATCAAGTTCCCCACGGTGGTGGCAGGGTTTGACCTGGTGGGGCATGAGGAC
ACTGGCCACTCCTTGCATGACTACAAGGAAGCTCTGATGATCCCCGCCAAGGATGGCGTTAAGC
TGCCTTACTTCTTCCACGCCGGAGAAACAGACTGGCAGGGTACTTCCATAGACAGGAACATTCT
GGATGCTCTGATGCTGAACACTACCAGAATCGGCCATGGATTTGCTTTGAGCAAACACCCCGCA
GTCAGGACTTATTCCTGGAAAAAGGACATCCCCATAGAAGTCTGTCCCATCTCTAACCAGGTGC
TGAAACTGGTGTCTGACTTGAGGAACCACCCTGTAGCCACTCTGATGGCCACTGGGCACCCCAT
GGTGATCAGCTCTGATGACCCAGCTATGTTTGGTGCCAAAGGCTTGTCCTATGATTTCTATGAG
GTCTTCATGGGCATTGGGGGGATGAAGGCTGATCTGAGGACCCTCAAACAGCTGGCCATGAACT
CTATCAAGTACAGTACCCTGTTGGAGAGTGAGAAAAATACTTTCATGGAAATATGGAAGAAGAG
ATGGGATAAGTTCATAGCAGATGTGGCTACAAAGTGAAGATCTTTGGATCCCTACCGGTGCTGC
GGCCGCGCAGTTAACGCCGCCCCTCTCCCTCCCCCCCCCCTAACGTTACTGGCCGAAGCCGCTT
GGAATAAGGCCGGTGTGCGTTTGTCTATATGTTATTTTCCACCATATTGCCGTCTTTTGGCAAT
GTGAGGGCCCGGAAACCTGGCCCTGTCTTCTTGACGAGCATTCCTAGGGGTCTTTCCCCTCTCG
CCAAAGGAATGCAAGGTCTGTTGAATGTCGTGAAGGAAGCAGTTCCTCTGGAAGCTTCTTGAAG
ACAAACAACGTCTGTAGCGACCCTTTGCAGGCAGCGGAACCCCCCACCTGGCGACAGGTGCCTC
TGCGGCCAAAAGCCACGTGTATAAGATACACCTGCAAAGGCGGCACAACCCCAGTGCCACGTTG
TGAGTTGGATAGTTGTGGAAAGAGTCAAATGGCTCTCCTCAAGCGTATTCAACAAGGGGCTGAA
```

-continued

```
GGATGCCCAGAAGGTACCCCATTGTATGGGATCTGATCTGGGGCCTCGGTACACATGCTTTACA
TGTGTTTAGTCGAGGTTAAAAAAACGTCTAGGCCCCCCGAACCACGGGGACGTGGTTTTCCTTT
GAAAAACACGATGATAATATGGCCACAACATACAGCTAGAAAGCTGTATTGCCTTTAGCACTCA
AGCTCAAAAGGTAAGCAACTCTCTGCAATTACCTTCTCTCTATATTAGCTCTTACTTGCACCTA
AACTTTAAAAAATTAACAATTATTGTGTTATGTGTTGTATCTTTAAGGGTGAAGTACCTGCGTG
ATACCCCTATAAAAACTTCTCACCTGTGTATGCATTCTGCACTATTTTATTATGTGTAAAAGC
TTTGTGTTTGTTTTCAGGAGGCTTATTCTTTGTGCTTAAAATATGTTTTAATTTCAGAACATC
TTATCCTGTCGTTCACTATCTGATATGCTTTGCAGTTTGCTTGATTAACTTCTAGCCCTACAGA
GTGCACAGAGAGCAAAATCATGGTGTTCAGTGAATTCTGGGGAGTTATTTTAATGTGAAAATTC
TCTAGAAGTTTAATTCCTGCAAAGTGCAGCTGCTGATCACTACACAAGATAAAAATGTGGGGGG
TGCATAAACGTATATTCTTACAATAATAGATACATGTGAACTTGTATACAGAAAAGAAAATGAG
AAAAATGTGTGTGCGTATACTCACACACGTGGTCAGTAAAAACTTTTGAGGGGTTTAATACAGA
AAATCCAATCCTGAGGCCCCAGCACTCAGTACGCATATAAAGGGCTGGGCTCTGAAGGACTTCT
GACTTTCACAGATTATATAAATCTCAGGAAAGCAACTAGATTCATGCTGGCTCCAAAAGCTGTG
CTTTATATAAGCACACTGGCTATACAATAGTTGTACAGTTCAGCTCTTTATAATAGAAACAGAC
AGAACAAGTATAAATCTTCTATTGGTCTATGTCATGAACAAGAATTCATTCAGTGGCTCTGTTT
TATAGTAAACATTGCTATTTTATCATGTCTGCATTTCTCTTCTGTCTGAATGTCACCACTAAAA
TTTAACTCCACAGAAAGTTTATACTACAGTACACATGCATATCTTTGAGCAAAGCAAACCATAC
CTGAAAGTGCAATAGAGCAGAATATGAATTACATGCGTGTCTTTCTCCTAGACTACATGACCCC
ATATAAATTACATTCCTTATCTATTCTGCCATCACCAAAACAAAGGTAAAAATACTTTTGAAGA
TCTACTCATAGCAAGTAGTGTGCAACAAACAGATATTTCTCTACATTTATTTTTAGGGAATAAA
AATAAGAAATAAAATAGTCAGCAAGCCTCTGCTTTCTCATATATCTGTCCAAACCTAAAGTTTA
CTGAAATTTGCTCTTTGAATTTCCAGTTTTGCAAGCCTATCAGATTGTGTTTTAATCAGAGGTA
CTGAAAAGTATCAATGAATTCTGATATCGTCGTGCCAGCTGCATTAATGAATCGGCCAACGCGC
GGGGAGAGGCGGTTTGCGTATTGGGCGCTCTTCCGCTTCCTCGCTCACTGACTCGCTGCGCTCG
GTCGTTCGGCTGCGGCGAGCGGTATCAGCTCACTCAAAGGCGGTAATACGGTTATCCACAGAAT
CAGGGGATAACGCAGGAAAGAACATGTGAGCAAAAGGCCAGCAAAAGGCCAGGAACCGTAAAAA
GGCCGCGTTGCTGGCGTTTTTCCATAGGCTCCGCCCCCCTGACGAGCATCACAAAAATCGATGC
TCAAGTCAGAGGTGGCGAAACCCGACAGGACTATAAAGATACCAGGCGTTTCCCCCTGGAAGCT
CCCTCGTGCGCTCTCCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGCCTTATCCGGTAACT
ATCGTCTTGAGTCCAACCCGGTAAGACACGACTTATCGCCACTGGCAGCAGCCACTGGTAACAG
GATTAGCAGAGCGAGGTATGTAGGCGGTGCTACAGAGTTCTTGAAGTGGTGGCCTAACTACGGC
TACACTAGAAGAACAGTATTTGGTATCTGCGCTCTGCTGAAGCCAGTTACCTTCGGAAAAAGAG
TTGGTAGCTCTTGATCCGGCAAACAAACCACCGCTGGTAGCGGTGGTTTTTTTGTTTGCAAGCA
GCAGATTACGCGCAGAAAAAAAGGATCTCAAGAAGATCCTTTGATCTTTTCTACGGGGTCTGAC
GCTCAGTGGAACGAAAACTCACGTTAAGGGATTTTGGTCATGAGATTATCAAAAAGGATCTTCA
CCTAGATCCTTTTAAATTAAAAATGAAGTTTTAAATCAATCTAAAGTATATATGAGTAAACTTG
GTCTGACAGTTACCAATGCTTAATCAGTGAGGCACCTATCTCAGCGATCTGTCTATTTCGTTCA
TCCATAGTTGCCTGACTCCCCGTCGTGTAGATAACTACGATACGGGAGGGCTTACCATCTGGCC
```

-continued

CCAGTGCTGCAATGATACCGCGAGACCCACGCTCACCGGCTCCAGATTTATCAGCAATAAACCA

GCCAGCCGGAAGGGCCGAGCGCAGAAGTGGTCCTGCAACTTTATCCGCCTCCATCCAGTCTATT

AATTGTTGCCGGGAAGCTAGAGTAAGTAGTTCGCCAGTTAATAGTTTGCGCAACGTTGTTGCCA

TTGCTACAGGCATCGTGGTGTCACGCTCGTCGTTTGGTATGGCTTCATTCAGCTCCGGTTCCCA

ACGATCAAGGCGAGTTACATGATCCCCCATGTTGTGCAAAAAAGCGGTTAGCTCCTTCGGTCCT

CCGATCGTTGTCAGAAGTAAGTTGGCCGCAGTGTTATCACTCATGGTTATGGCAGCACTGCATA

ATTCTCTTACTGTCATGCCATCCGTAAGATGCTTTTCTGTGACTGGTGAGTACTCAACCAAGTC

ATTCTGAGAATAGTGTATGCGGCGACCGAGTTGCTCTTGCCCGGCGTCAATACGGGATAATACC

GCGCCACATAGCAGAACTTTAAAAGTGCTCATCATTGGAAAACGTTCTTCGGGGCGAAAACTCT

CAAGGATCTTACCGCTGTTGAGATCCAGTTCGATGTAACCCACTCGTGCACCCAACTGATCTTC

AGCATCTTTTACTTTCACCAGCGTTTCTGGGTGAGCAAAAACAGGAAGGCAAAATGCCGCAAAA

AAGGGAATAAGGGCGACACGGAAATGTTGAATACTCATACTCTTCCTTTTTCAATATTATTGAA

GCATTTATCAGGGTTATTGTCTCATGAGCGGATACATATTTGAATGTATTTAGAAAAATAAACA

AATAGGGGTTCCGCGCACATTTCCCCGA
         -----------------

OV Construct 4 hCECR1, SEQ ID NO: 50
AAAGTGCCACCTGACGTCGACGGTTATCCACAGAATCAGGGGATAACGCAGGAAAGAACATGTG

CGCATGCCTGCTATTGTCTTCCCAATCCTCCCCCTTGCTGTCCTGCCCCACCCCACCCCCCAGA

ATAGAATGACACCTACTCAGACAATGCGATGCAATTTCCTCATTTTATTAGGAAAGGACAGTGG

GAGTGGCACCTTCCAGGGTCAAGGAAGGCACGGGGAGGGGCAAACAACAGATGGCTGGCAACT

AGAAGGCACAGTCGAGGCTGATCAGCGAGCTCTAGCATTTAGGTGACACTATAGAATAGGGCCC

TCTAGCGAATTAATTCAGGTTGTTAACAACAACAATTTTCGAAGGTACCTCAGGCACCGGGCTT

GCGGGTCATGCACCAGGTGCGCGGTCCTTCGGGCACCTCGACGTCGGCGGTGACGGTGAAGCCG

AGCCGCTCGTAGAAGGGGAGGTTGCGGGGCGCGGAGGTCTCCAGGAAGGCGGGCACCCCGGCGC

GCTCGGCCGCCTCCACTCCGGGGAGCACGACGGCGCTGCCCAGACCCTTGCCCTGGTGGTCGGG

CGAGACGCCGACGGTGGCCAGGAACCACGCGGGCTCCTTGGGCCGGTGCGGCGCCAGGAGGCCT

TCCATCTGTTGCTGCGCGGCCAGCCGGGAACCGCTCAACTCGGCCATGCGCGGGCCGATCTCGG

CGAACACCGCCCCCGCTTCGACGCTCTCCGGCGTGGTCCAGACCGCCACCGCGGCGCCGTCGTC

CGCGACCCACACCTTGCCGATGTCGAGCCCGACGCGCGTGAGGAAGAGTTCTTGCAGCTCGGTG

ACCCGCTCGATGTGGCGGTCCGGGTCGACGGTGTGGCGCGTGGCGGGGTAGTCGGCGAACGCGG

CGGCGAGGGTGCGTACGGCCCGGGGGACGTCGTCGCGGGTGGCGAGGCGCACCGTGGGCTTGTA

CTCGGTCATGGTACCAGCTTTTTGCAAAAGCCTAGGCCTCCAAAAAAGCCTCCTCACTACTTCT

GGAATAGCTCAGAGGCAGAGGCGGCCTCGGCCTCTGCATAAATAAAAAAAATTAGTCAGCCATG

GGGCGGAGAATGGGCGGAACTGGGCGGAGTTAGGGGCGGGATGGGCGGAGTTAGGGGCGGGACT

ATGGTTGCTGACTAATTGAGATGCATGCTTTGCATACTTCTGCCTGCTGGGGAGCCTGGGGACT

TTCCACACCTGGTTGCTGACTAATTGAGATGCATGCTTTGCATACTTCTGCCTGCTGGGGAGCC

TGGGGACTTTCCACACCCTAACTGACACACATTCCACAGACATGTGAGCAAAAGGCCAGCAAAA

GGACTAGTTATTGTAATAAATGAGAATTCATTGAAATGTTAGTATGCTAACTCAATCTAAATTA

TAAAGATAAAGAGGCATTTAATCACAGCTAGATTTCCATCACTTGTGACAGACAGGCATATGAA

TGATTATGTACAGCTCTAGGAAAAAAAGTATGTAGGAAAACTAGTACATTTTGATTAGAAAGTC

TGAAAATGAGGTGCCTTGATCCAAGAGAATACGTGTGTTTGAGAAAAAAAAAGTTTGGATAGAG

-continued

```
GTGGTAAGAGAGAATATATTGAAATGGTGTTTCTACAAACTGCCATGGCCAGATTTGTGTAAGA
GACATTCAGTAAGTAGGCAAGGAAAGAAATATTACTAGGTACAAAGCAACATTAGTAATACCAA
AAGAAACCAATTATTCCAGATGCCAATCTCGTAATAGGGTTAAGAGATTTCCACCCCTCTAGTG
GTCACCAGTGCAACCAGTAACTTTGCTAATTTACATTTTCTTTTTTTAAATGGCAGATATAGCT
TTGAACTGAGTGATCATGAACTGGTACTGTGTAAATAAGATGGAAGCATACTTGGCAGCTAAAC
TTCTAGTTTTTAAAAACTCAAATTCTCTTGAAAGATCAGTTCCCAGTCTAGTAACAGCTGATAG
TTTAAGTATCAGTAATTGGCTACCATTAACAACTGGCTCCTGAGAGGTCTTAAATGTAGAGACA
GCTTTAAACTCAAAAGCACAGAGTGATTTTTAGAATAGACTTCCCAAGCAAAGAAAATAAACAG
GGAGGAGCTTTAAGGGAGTAGCCATCTCATTATTATTATTATTTAAAGAAATGGCAGCAAGCCT
ACAAAAGAAAAATAAGACAGAGCAGAGAAGAAAGAGTCATGGTATGCTTTTCTATCTTAGCAAA
ATTAATCTCTACATGCCTAGGAAAAAGCCATGACAAGAGCAATCAGTTCAAAAGGTGTATGCAA
AAACCACATAATAGTAACTAGTACTGCATTGCCAGGAAGGAAGTTATGTCGCCATTCCATGGA
TCTCATTCTCATTTCCTTGCAGCTTGAGAGTATAATCAACTTTGAAAAACTGACTGAATGGACC
AGTTCTAATGTTATGGAAGAGAGGAAGATCAAAGTGTACTTACCTCGCATGAAGATGGAGGAAA
AATACAACCTCACATCTGTCTTAATGGCTATGGGCATTACTGACGTGTTTAGCTCTTCAGCCAA
TCTGTCTGGCATCTCCTCAGCAGAGAGCCTGAAGATATCTCAAGCTGTCCATGCAGCACATGCA
GAAATCAATGAAGCAGGCAGAGAGGTGGTAGGGTCAGCAGAGGCTGGAGTGGATGCTGCAAGCG
TCTCTGAAGAATTTAGGGCTGACCATCCATTCCTCTTCTGTATCAAGCACATCGCAACCAACGC
CGTTCTCTTCTTTGGCAGATGTGTTTCCCCTTAAAAAGAAGAAAGCTGAAAAACGCCGCCCCTC
TCCCTCCCCCCCCCCTAACGTTACTGGCCGAAGCCGCTTGGAATAAGGCCGGTGTGCGTTTGTC
TATATGTTATTTTCCACCATATTGCCGTCTTTTGGCAATGTGAGGGCCCGGAAACCTGGCCCTG
TCTTCTTGACGAGCATTCCTAGGGGTCTTTCCCCTCTCGCCAAAGGAATGCAAGGTCTGTTGAA
TGTCGTGAAGGAAGCAGTTCCTCTGGAAGCTTCTTGAAGACAAACAACGTCTGTAGCGACCCTT
TGCAGGCAGCGGAACCCCCCACCTGGCGACAGGTGCCTCTGCGGCCAAAAGCCACGTGTATAAG
ATACACCTGCAAAGGCGGCACAACCCCAGTGCCACGTTGTGAGTTGGATAGTTGTGGAAAGAGT
CAAATGGCTCTCCTCAAGCGTATTCAACAAGGGGCTGAAGGATGCCCAGAAGGTACCCCATTGT
ATGGGATCTGATCTGGGCCTCGGTACACATGCTTTACATGTGTTTAGTCGAGGTTAAAAAAAC
GTCTAGGCCCCCGAACCACGGGGACGTGGTTTTCCTTTGAAAAACACGATGATAATATGGCCA
CAGCCACCATGTTGGTGGATGGCCCATCTGAGCGGCCAGCCCTGTGCTTCTTGCTGTTGGCTGT
GGCAATGTCTTTCTTCGGCTCTGCTCTATCCATAGATGAAACACGGGCGCATCTGTTGTTGAAA
GAAAAGATGATGCGGCTGGGGGGGCGGCTGGTGCTGAACACCAAGGAGGAGCTGGCCAATGAGA
GGCTCATGACGCTCAAAATCGCTGAGATGAAGGAGGCCATGAGGACCCTGATATTCCCACCCAG
CATGCACTTTTTCCAGGCCAAGCATCTCATTGAGAGAAGTCAAGTGTTTAATATTCTAAGGATG
ATGCCAAAAGGGGCTGCCTTGCACCTCCATGACATTGGCATCGTGACTATGGACTGGCTGGTGA
GGAATGTCACCTACAGGCCTCACTGCCACATCTGTTTCACCCCAAGGGGATCATGCAGTTCAG
ATTTGCTCACCCAACTCCCCGTCCATCAGAAAATGTTCCAAGTGGATTCTGCTGGAGGATTAT
CGGAAGCGGGTGCAGAACGTCACTGAGTTTGATGACAGCTTGCTGAGGAATTTCACTCTGGTGA
CCCAGCACCCGGAGGTGATTTACACAAACCAAAATGTTGTCTGGTCGAAATTTGAAACCATCTT
CTTCACCATCTCTGGTCTCATCCATTACGCTCCAGTGTTCAGAGACTATGTCTTCCGGAGCATG
CAGGAGTTCTACGAGGACAACGTGCTCTACATGGAGATCAGAGCCAGGCTGCTGCCGGTGTATG
AGCTCAGTGGAGAGCACCATGACGAAGAGTGGTCAGTGAAGACTTATCAGGAAGTAGCTCAGAA
```

-continued

```
GTTTGTGGAAACTCATCCTGAGTTTATTGGAATCAAAATCATTTATTCGGATCACAGATCCAAA
GATGTGGCTGTCATCGCAGAATCCATCCGAATGGCCATGGGGCTCCGAATCAAGTTCCCCACGG
TGGTGGCAGGGTTTGACCTGGTGGGGCATGAGGACACTGGCCACTCCTTGCATGACTACAAGGA
AGCTCTGATGATCCCCGCCAAGGATGGCGTTAAGCTGCCTTACTTCTTCCACGCCGGAGAAACA
GACTGGCAGGGTACTTCCATAGACAGGAACATTCTGGATGCTCTGATGCTGAACACTACCAGAA
TCGGCCATGGATTTGCTTTGAGCAAACACCCCGCAGTCAGGACTTATTCCTGGAAAAAGGACAT
CCCCATAGAAGTCTGTCCCATCTCTAACCAGGTGCTGAAACTGGTGTCTGACTTGAGGAACCAC
CCTGTAGCCACTCTGATGGCCACTGGGCACCCCATGGTGATCAGCTCTGATGACCCAGCTATGT
TTGGTGCCAAAGGCTTGTCCTATGATTTCTATGAGGTCTTCATGGGCATTGGGGGATGAAGGC
TGATCTGAGGACCCTCAAACAGCTGGCCATGAACTCTATCAAGTACAGTACCCTGTTGGAGAGT
GAGAAAAATACTTTCATGGAAATATGGAAGAAGAGATGGGATAAGTTCATAGCAGATGTGGCTA
CAAAGTGATCTGTCCCTTCCAACAAGACCCAGAGCACTGTAGTATCAGGGGTAAAATGAAAAGT
ATGTTATCTGCTGCATCCAGACTTCATAAAAGCTGGAGCTTAATCTAGAAAAAAAATCAGAAAG
AAATTACACTGTGAGAACAGGTGCAATTCACTTTTCCTTTACACAGAGTAATACTGGTAACTCA
TGGATGAAGGCTTAAGGGAATGAAATTGGACTCACAGTACTGAGTCATCACACTGAAAAATGCA
ACCTGATACATCAGCAGAAGGTTTATGGGGAAAAATGCAGCCTTCCAATTAAGCCAGATATCT
GTATGACCAAGCTGCTCCAGAATTAGTCACTCAAAATCTCTCAGATTAAATTATCAACTGTCAC
CAACCATTCCTATGCTGACAAGGCAATTGCTTGTTCTCTGTGTTCCTGATACTACAAGGCTCTT
CCTGACTTCCTAAAGATGCATTATAAAAATCTTATAATTCACATTTCTCCCTAAACTTTGACTC
AATCATGGTATGTTGGCAAATATGGTATATTACTATTCAAATTGTTTTCCTTGTACCCATATGT
AATGGGTCTTGTGAATGTGCTCTTTTGTTCCTTTAATCATAATAAAAACATGTTTAAGCAAACA
CTTTTCACTTGTAGTATTTGAAGTACAGCAAGGTTGTGTAGCAGGGAAAGAATGACATGCAGAG
GAATAAGTATGGACACACAGGCTAGCAGCGACTGTAGAACAAGTACTAATGGGTGAGAAGTTGA
ACAAGAGTCCCCTACAGCAACTTAATCTAATAAGCTAGTGGTCTACATCAGCTAAAAGAGCATA
GTGAGGGATGAAATTGGTTCTCCTTTCTAAGCATCACCTGGGACAACTCATCTGGAGCAGTGTG
TCCAATCTGCCGCTGCCCTGATCCTGGCTGGGGTGATGGGACAGACCTTGGCTGCCACTGAGAC
ATCTGAGACACTGAGATCTGTCTCAACTCAGATTTACCCAAGAACAGATCATTGCCAACAGAAC
AAAATCTCAAACTTATGGCTAGTGATGACAGCAGTCAGTTGTCCCATCTGTGACCCACCAAGGC
TGGCATGCTGGAATGAGCAGGCTTTGGTGGCTTGTAGTTACTGGACAGCACCACTGACATGGGC
AGGGGAAAAACTGAGCATGGTGTAAATCACTGCCTCAAAGCCACTTCTCTGTGCCTGCACCATG
CTTGAAAGCTCTTCTACAGGAGCTGGGTTTGTTCAAGAAAGCTTCTGTTTCTCCCATCTGCTTC
TTGTACCTTCACAGGGACAGAGTTAGAAGGGTACAGCCATGGTCGTGCCAGCTGCATTAATGAA
TCGGCCAACGCGCGGGAGAGGCGGTTTGCGTATTGGGCGCTCTTCCGCTTCCTCGCTCACTGA
CTCGCTGCGCTCGGTCGTTCGGCTGCGGCGAGCGGTATCAGCTCACTCAAAGGCGGTAATACGG
TTATCCACAGAATCAGGGGATAACGCAGGAAAGAACATGTGAGCAAAAGGCCAGCAAAAGGCCA
GGAACCGTAAAAAGGCCGCGTTGCTGGCGTTTTTCCATAGGCTCCGCCCCCCTGACGAGCATCA
CAAAAATCGATGCTCAAGTCAGAGGTGGCGAAACCCGACAGGACTATAAAGATACCAGGCGTTT
CCCCCTGGAAGCTCCCTCGTGCGCTCTCCTGTTCCGACCCTGCCGCTTACCGGATACCTGTCCG
CCTTTCTCCCTTCGGGAAGCGTGGCGCTTTCTCATAGCTCACGCTGTAGGTATCTCAGTTCGGT
GTAGGTCGTTCGCTCCAAGCTGGGCTGTGTGCACGAACCCCCCGTTCAGCCCGACCGCTGCGCC
```

-continued

```
TTATCCGGTAACTATCGTCTTGAGTCCAACCCGGTAAGACACGACTTATCGCCACTGGCAGCAG

CCACTGGTAACAGGATTAGCAGAGCGAGGTATGTAGGCGGTGCTACAGAGTTCTTGAAGTGGTG

GCCTAACTACGGCTACACTAGAAGAACAGTATTTGGTATCTGCGCTCTGCTGAAGCCAGTTACC

TTCGGAAAAAGAGTTGGTAGCTCTTGATCCGGCAAACAAACCACCGCTGGTAGCGGTGGTTTTT

TTGTTTGCAAGCAGCAGATTACGCGCAGAAAAAAAGGATCTCAAGAAGATCCTTTGATCTTTTC

TACGGGGTCTGACGCTCAGTGGAACGAAAACTCACGTTAAGGGATTTTGGTCATGAGATTATCA

AAAAGGATCTTCACCTAGATCCTTTTAAATTAAAAATGAAGTTTTAAATCAATCTAAAGTATAT

ATGAGTAAACTTGGTCTGACAGTTACCAATGCTTAATCAGTGAGGCACCTATCTCAGCGATCTG

TCTATTTCGTTCATCCATAGTTGCCTGACTCCCCGTCGTGTAGATAACTACGATACGGGAGGGC

TTACCATCTGGCCCCAGTGCTGCAATGATACCGCGAGACCCACGCTCACCGGCTCCAGATTTAT

CAGCAATAAACCAGCCAGCCGGAAGGGCCGAGCGCAGAAGTGGTCCTGCAACTTTATCCGCCTC

CATCCAGTCTATTAATTGTTGCCGGGAAGCTAGAGTAAGTAGTTCGCCAGTTAATAGTTTGCGC

AACGTTGTTGCCATTGCTACAGGCATCGTGGTGTCACGCTCGTCGTTTGGTATGGCTTCATTCA

GCTCCGGTTCCCAACGATCAAGGCGAGTTACATGATCCCCCATGTTGTGCAAAAAAGCGGTTAG

CTCCTTCGGTCCTCCGATCGTTGTCAGAAGTAAGTTGGCCGCAGTGTTATCACTCATGGTTATG

GCAGCACTGCATAATTCTCTTACTGTCATGCCATCCGTAAGATGCTTTTCTGTGACTGGTGAGT

ACTCAACCAAGTCATTCTGAGAATAGTGTATGCGGCGACCGAGTTGCTCTTGCCCGGCGTCAAT

ACGGGATAATACCGCGCCACATAGCAGAACTTTAAAAGTGCTCATCATTGGAAAACGTTCTTCG

GGGCGAAAACTCTCAAGGATCTTACCGCTGTTGAGATCCAGTTCGATGTAACCCACTCGTGCAC

CCAACTGATCTTCAGCATCTTTTACTTTCACCAGCGTTTCTGGGTGAGCAAAAACAGGAAGGCA

AAATGCCGCAAAAAAGGGAATAAGGGCGACACGGAAATGTTGAATACTCATACTCTTCCTTTTT

CAATATTATTGAAGCATTTATCAGGGTTATTGTCTCATGAGCGGATACATATTTGAATGTATTT

AGAAAAATAAACAAATAGGGGTTCCGCGCACATTTCCCCGA
```

Construct 5 Hc-P2A-Lc-P2A-OVAL, SEQ ID NO: 51

```
AAAGTGCCACCTGACGTCGACGGTTATCCACAGAATCAGGGGATAACGCAGGAAAGAACATGTG

CGCATGCCTGCTATTGTCTTCCCAATCCTCCCCCTTGCTGTCCTGCCCCACCCCACCCCCCAGA

ATAGAATGACACCTACTCAGACAATGCGATGCAATTTCCTCATTTTATTAGGAAAGGACAGTGG

GAGTGGCACCTTCCAGGGTCAAGGAAGGCACGGGGGAGGGGCAAACAACAGATGGCTGGCAACT

AGAAGGCACAGTCGAGGCTGATCAGCGAGCTCTAGCATTTAGGTGACACTATAGAATAGGGCCC

TCTAGCGAATTAATTCAGGTTGTTAACAACAACAATTTTCGAAGGTACCTCAGGCACCGGGCTT

GCGGGTCATGCACCAGGTGCGCGGTCCTTCGGGCACCTCGACGTCGGCGGTGACGGTGAAGCCG

AGCCGCTCGTAGAAGGGGAGGTTGCGGGGCGCGGAGGTCTCCAGGAAGGCGGGCACCCCGGCGC

GCTCGGCCGCCTCCACTCCGGGGAGCACGACGGCGCTGCCCAGACCCTTGCCCTGGTGGTCGGG

CGAGACGCCGACGGTGGCCAGGAACCACGCGGGCTCCTTGGGCCGGTGCGGCGCCAGGAGGCCT

TCCATCTGTTGCTGCGCGGCCAGCCGGGAACCGCTCAACTCGGCCATGCGCGGGCCGATCTCGG

CGAACACCGCCCCCGCTTCGACGCTCTCCGGCGTGGTCCAGACCGCCACCGCGGCGCCGTCGTC

CGCGACCCACACCTTGCCGATGTCGAGCCCGACGCGCGTGAGGAAGAGTTCTTGCAGCTCGGTG

ACCCGCTCGATGTGGCGGTCCGGGTCGACGGTGTGGCGCGTGGCGGGGTAGTCGGCGAACGCGG

CGGCGAGGGTGCGTACGGCCCGGGGGACGTCGTCGCGGGTGGCGAGGCGCACCGTGGGCTTGTA

CTCGGTCATGGTACCAGCTTTTTGCAAAAGCCTAGGCCTCCAAAAAAGCCTCCTCACTACTTCT

GGAATAGCTCAGAGGCAGAGGCGGCCTCGGCCTCTGCATAAATAAAAAAAATTAGTCAGCCATG
```

-continued

```
GGGCGGAGAATGGGCGGAACTGGGCGGAGTTAGGGGCGGGATGGGCGGAGTTAGGGGCGGGACT
ATGGTTGCTGACTAATTGAGATGCATGCTTTGCATACTTCTGCCTGCTGGGGAGCCTGGGGACT
TTCCACACCTGGTTGCTGACTAATTGAGATGCATGCTTTGCATACTTCTGCCTGCTGGGGAGCC
TGGGGACTTTCCACACCCTAACTGACACACATTCCACAGACATGTGAGCAAAAGGCCAGCAAAA
GGACTAGTTATTGATATCAGTACCTGCGTGATACCCCCTATAAAAACTTCTCACCTGTGTATGC
ATTCTGCACTATTTTATTATGTGTAAAAGCTTTGTGTTTGTTTTCAGGAGGCTTATTCTTTGTG
CTTAAAATATGTTTTTAATTTCAGAACATCTTATCCTGTCGTTCACTATCTGATATGCTTTGCA
GTTTGCTTGATTAACTTCTAGCCCTACAGAGTGCACAGAGAGCAAAATCATGGTGTTCAGTGAA
TTCTGGGGAGTTATTTTAATGTGAAAATTCTCTAGAAGTTTAATTCCTGCAAAGTGCAGCTGCT
GATCACTACACAAGATAAAAATGTGGGGGGTGCATAAACGTATATTCTTACAATAATAGATACA
TGTGAACTTGTATACAGAAAAGAAAATGAGAAAAATGTGTGTGCGTATACTCACACACGTGGTC
AGTAAAAACTTTTGAGGGGTTTAATACAGAAAATCCAATCCTGAGGCCCCAGCACTCAGTACGC
ATATAAAGGGCTGGGCTCTGAAGGACTTCTGACTTTCACAGATTATATAAATCTCAGGAAAGCA
ACTAGATTCATGCTGGCTCCAAAAGCTGTGCTTTATATAAGCACACTGGCTATACAATAGTTGT
ACAGTTCAGCTCTTTATAATAGAAACAGACAGAACAAGTATAAATCTTCTATTGGTCTATGTCA
TGAACAAGAATTCATTCAGTGGCTCTGTTTTATAGTAAACATTGCTATTTTATCATGTCTGCAT
TTCTCTTCTGTCTGAATGTCACCACTAAAATTTAACTCCACAGAAAGTTTATACTACAGTACAC
ATGCATATCTTTGAGCAAAGCAAACCATACCTGAAAGTGCAATAGAGCAGAATATGAATTACAT
GCGTGTCTTTCTCCTAGACTACATGACCCCATATAAATTACATTCCTTATCTATTCTGCCATCA
CCAAAACAAAGGTAAAAATACTTTTGAAGATCTACTCATAGCAAGTAGTGTGCAACAAACAGAT
ATTTCTCTACATTTATTTTTAGGGAATAAAAATAAGAAATAAAATAGTCAGCAAGCCTCTGCTT
TCTCATATATCTGTCCAAACCTAAAGTTTACTGAAATTTGCTCTTTGAATTTCCAGTTTTGCAA
GCCTATCAGATTGTGTTTTAATCAGAGGTACTGAAAAGTATCAATGAATTCTAGCTTTCACTGA
ACAAAAATATGTAGAGGCAACTGGCTTCTGGGACAGTTTGCTACCCAAAAGACAACTGAATGCA
AATACATAAATAGATTTATGAATATGGTTTTGAACATGCACATGAGAGGTGGATATAGCAACAG
ACACATTACCACAGAATTACTTTAAAACTACTTGTTAACATTTAATTGCCTAAAAACTGCTCGT
AATTTACTGTTGTAGCCTACCATAGAGTACCCTGCATGGTACTATGTACAGCATTCCATCCTTA
CATTTTCACTGTTCTGCTGTTTGCTCTAGACAACTCAGAGTTCACC[AntibodyHeavyChai
nCodingSequence]GGAAGCGGAGCTACTAACTTCAGCCTGCTGAAGCAGGCTGGAGACGTG
GAGGAGAACCCTGGACCT[AntibodyLightChainCodingSequence]GGAAGCGGAGCT
ACTAACTTCAGCCTGCTGAAGCAGGCTGGAGACGTGGAGGAGAACCCTGGACCTATGGGCTCCA
TCGGTGCAGCAAGCATGGAATTTGTTTTGATGTATTCAAGGAGCTCAAAGTCCACCATGCCAA
TGAGAACATCTTCTACTGCCCCATTGCCATCATGTCAGCTCTAGCCATGGTATACCTGGGTGCA
AAAGACAGCACCAGGACACAAATAAATAAGGTGAGCCTACAGTTAAAGATTAAAACCTTTGCCC
TGCTCAATGGAGCCACAGCACTTAATTGTATGATAATGTCCCTTGGAAACTGCATAGCTCAGAG
GCTGAAAATCTGAAACCAGAGTTATCTAAAAGTGTGGCCACCTCCAACTCCCAGAGTGTTACCC
AAATGCACTAGCTAGAAATCTTGAAACTGGATTGCATAACTTCTTTTTGTCATAACCATTATTT
CAGCTACTATTATTTTCAATTACAGGTTGTTCGCTTTGATAAACTTCCAGGATTCGGAGACAGT
ATTGAAGCTCAGGTACAGAAATAATTTCACCTCCTTCTCTATGTCCCTTTCCTCTGGAAGCAAA
ATACAGCAGATGAAGCAATCTCTTAGCTGTTCCAAGCCCTCTCTGATGAGCAGCTAGTGCTCTG
CATCCAGCAGTTGGGAGAACACTGTTCATAAGAACAGAGAAAAAGAAGGAAGTAACAGGGGATT
```

```
CAGAACAAACAGAAGATAAAACTCAGGACAAAAATACCGTGTGAATGAGGAAACTTGTGGATAT
TTGTACGCTTAAGCAAGACAGCTAGATGATTCTGGATAAATGGGTCTGGTTGGAAAAGAAGGAA
AGCCTGGCTGATCTGCTGGAGCTAGATTATTGCAGCAGGTAGGCAGGAGTTCCCTAGAGAAAAG
TATGAGGGAATTACAGAAGAAAAACAGCACAAAATTGTAAATATTGGAAAAGGACCACATCAGT
GTAGTTACTAGCAGTAAGACAGACAGGATGAAAAATAGTTTTGTAAACAGAAGTATCTAACTAC
TTTACTCTGTTCATACACTACGTAAAACCTACTAAGTAATAAAACTAGAATAACAACATCTTTC
TTTCTCTTTGTATTCAGTGTGGCACATCTGTAAACGTTCACTCTTCACTTAGAGACATCCTCAA
CCAAATCACCAAACCAAATGATGTTTATTCGTTCAGCCTTGCCAGTAGACTTTATGCTGAAGAG
AGATACCCAATCCTGCCAGTAAGTTGCTCTAAAATCTGATCTGAGTGTATTTCCATGCCAAAGC
TCTACCATTCTGTAATGCAAAAACAGTCAGAGTTCCACATGTTTCACTAAGAAAATTTCTTTTT
CTCTTGTTTTTACAAATGAAAGAGAGGACAAATAACATTTCTCTATCACCGACCTGAAACTCTA
CAGTCTTCAGAGAATGAATGGCTTGCTAAAAGAATGTCAAATCTTACCATACAGCTATTTCATA
TTACACTACTAAATACACTATAAGGCATAGCATGTAGTAATACAGTGTAAAATAGCTTTTTACA
CTACTAGATATCGTCGTGCCAGCTGCATTAATGAATCGGCCAACGCGCGGGGAGAGGCGGTTTG
CGTATTGGGCGCTCTTCCGCTTCCTCGCTCACTGACTCGCTGCGCTCGGTCGTTCGGCTGCGGC
GAGCGGTATCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCGTTGCTGGCG
TTTTTCCATAGGCTCCGCCCCCTGACGAGCATCACAAAAATCGATGCTCAAGTCAGAGGTGGC
GAAACCCGACAGGACTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGGGAAGCGTGGCGCTT
TCTCATAGCTCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCTTGAGTCCAA
CCCGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGAACAG
TATTTGGTATCTGCGCTCTGCTGAAGCCAGTTACCTTCGGAAAAAGAGTTGGTAGCTCTTGATC
CGGCAAACAAACCACCGCTGGTAGCGGTGGTTTTTTTGTTTGCAAGCAGCAGATTACGCGCAGA
AAAAAAGGATCTCAAGAAGATCCTTTGATCTTTTCTACGGGGTCTGACGCTCAGTGGAACGAAA
ACTCACGTTAAGGGATTTTGGTCATGAGATTATCAAAAAGGATCTTCACCTAGATCCTTTTAAA
TTAAAAATGAAGTTTTAAATCAATCTAAAGTATATATGAGTAAACTTGGTCTGACAGTTACCAA
TGCTTAATCAGTGAGGCACCTATCTCAGCGATCTGTCTATTTCGTTCATCCATAGTTGCCTGAC
TCCCCGTCGTGTAGATAACTACGATACGGGAGGGCTTACCATCTGGCCCCAGTGCTGCAATGAT
ACCGCGAGACCCACGCTCACCGGCTCCAGATTTATCAGCAATAAACCAGCCAGCCGGAAGGGCC
GAGCGCAGAAGTGGTCCTGCAACTTTATCCGCCTCCATCCAGTCTATTAATTGTTGCCGGGAAG
CTAGAGTAAGTAGTTCGCCAGTTAATAGTTTGCGCAACGTTGTTGCCATTGCTACAGGCATCGT
GGTGTCACGCTCGTCGTTTGGTATGGCTTCATTCAGCTCCGGTTCCCAACGATCAAGGCGAGTT
ACATGATCCCCCATGTTGTGCAAAAAAGCGGTTAGCTCCTTCGGTCCTCCGATCGTTGTCAGAA
GTAAGTTGGCCGCAGTGTTATCACTCATGGTTATGGCAGCACTGCATAATTCTCTTACTGTCAT
GCCATCCGTAAGATGCTTTTCTGTGACTGGTGAGTACTCAACCAAGTCATTCTGAGAATAGTGT
ATGCGGCGACCGAGTTGCTCTTGCCCGGCGTCAATACGGGATAATACCGCGCCACATAGCAGAA
CTTTAAAAGTGCTCATCATTGGAAAACGTTCTTCGGGGCGAAAACTCTCAAGGATCTTACCGCT
```

-continued

```
GTTGAGATCCAGTTCGATGTAACCCACTCGTGCACCCAACTGATCTTCAGCATCTTTTACTTTC

ACCAGCGTTTCTGGGTGAGCAAAAACAGGAAGGCAAAATGCCGCAAAAAAGGGAATAAGGGCGA

CACGGAAATGTTGAATACTCATACTCTTCCTTTTTCAATATTATTGAAGCATTTATCAGGGTTA

TTGTCTCATGAGCGGATACATATTTGAATGTATTTAGAAAAATAAACAAATAGGGGTTCCGCGC

ACATTTCCCCGA
```

-----------------

```
Construct 6 OVAL-P2A-Hc-P2A-Lc, SEQ ID NO: 52
AAAGTGCCACCTGACGTCGACGGTTATCCACAGAATCAGGGGATAACGCAGGAAAGAACATGTG

CGCATGCCTGCTATTGTCTTCCCAATCCTCCCCCTTGCTGTCCTGCCCCACCCCACCCCCCAGA

ATAGAATGACACCTACTCAGACAATGCGATGCAATTTCCTCATTTTATTAGGAAAGGACAGTGG

GAGTGGCACCTTCCAGGGTCAAGGAAGGCACGGGGGAGGGGCAAACAACAGATGGCTGGCAACT

AGAAGGCACAGTCGAGGCTGATCAGCGAGCTCTAGCATTTAGGTGACACTATAGAATAGGGCCC

TCTAGCGAATTAATTCAGGTTGTTAACAACAACAATTTTCGAAGGTACCTCAGGCACCGGGCTT

GCGGGTCATGCACCAGGTGCGCGGTCCTTCGGGCACCTCGACGTCGGCGGTGACGGTGAAGCCG

AGCCGCTCGTAGAAGGGGAGGTTGCGGGGCGCGGAGGTCTCCAGGAAGGCGGGCACCCCGGCGC

GCTCGGCCGCCTCCACTCCGGGGAGCACGACGGCGCTGCCCAGACCCTTGCCCTGGTGGTCGGG

CGAGACGCCGACGGTGGCCAGGAACCACGCGGGCTCCTTGGGCCGGTGCGGCGCCAGGAGGCCT

TCCATCTGTTGCTGCGCGGCCAGCCGGGAACCGCTCAACTCGGCCATGCGCGGGCCGATCTCGG

CGAACACCGCCCCCGCTTCGACGCTCTCCGGCGTGGTCCAGACCGCCACCGCGGCGCCGTCGTC

CGCGACCCACACCTTGCCGATGTCGAGCCCGACGCGCGTGAGGAAGAGTTCTTGCAGCTCGGTG

ACCCGCTCGATGTGGCGGTCCGGGTCGACGGTGTGGCGCGTGGCGGGGTAGTCGGCGAACGCGG

CGGCGAGGGTGCGTACGGCCCGGGGGACGTCGTCGCGGGTGGCGAGGCGCACCGTGGGCTTGTA

CTCGGTCATGGTACCAGCTTTTTGCAAAAGCCTAGGCCTCCAAAAAAGCCTCCTCACTACTTCT

GGAATAGCTCAGAGGCAGAGGCGGCCTCGGCCTCTGCATAAATAAAAAAAAATTAGTCAGCCATG

GGGCGGAGAATGGGCGGAACTGGGCGGAGTTAGGGGCGGGATGGGCGGAGTTAGGGGCGGGACT

ATGGTTGCTGACTAATTGAGATGCATGCTTTGCATACTTCTGCCTGCTGGGGAGCCTGGGGACT

TTCCACACCTGGTTGCTGACTAATTGAGATGCATGCTTTGCATACTTCTGCCTGCTGGGGAGCC

TGGGGACTTTCCACACCCTAACTGACACACATTCCACAGACATGTGAGCAAAAGGCCAGCAAAA

GGACTAGTTATTATAAATGAGAATTCATTGAAATGTTAGTATGCTAACTCAATCTAAATTATAA

AGATAAAGAGGCATTTAATCACAGCTAGATTTCCATCACTTGTGACAGACAGGCATATGAATGA

TTATGTACAGCTCTAGGAAAAAAAGTATGTAGGAAAACTAGTACATTTTGATTAGAAAGTCTGA

AAATGAGGTGCCTTGATCCAAGAGAATACGTGTGTTTGAGAAAAAAAAGTTTGGATAGAGGTG

GTAAGAGAGAATATATTGAAATGGTGTTTCTACAAACTGCCATGGCCAGATTTGTGTAAGAGAC

ATTCAGTAAGTAGGCAAGGAAAGAAATATTACTAGGTACAAAGCAACATTAGTAATACCAAAAG

AAACCAATTATTCCAGATGCCAATCTCGTAATAGGGTTAAGAGATTTCCACCCCTCTAGTGGTC

ACCAGTGCAACCAGTAACTTTGCTAATTTACATTTTCTTTTTTTAAATGGCAGATATAGCTTTG

AACTGAGTGATCATGAACTGGTACTGTGTAAATAAGATGGAAGCATACTTGGCAGCTAAACTTC

TAGTTTTTAAAAACTCAAATTCTCTTGAAAGATCAGTTCCCAGTCTAGTAACAGCTGATAGTTT

AAGTATCAGTAATTGGCTACCATTAACAACTGGCTCCTGAGAGGTCTTAAATGTAGAGACAGCT

TTAAACTCAAAAGCACAGAGTGATTTTTAGAATAGACTTCCCAAGCAAAGAAAATAAACAGGGA

GGAGCTTTAAGGGAGTAGCCATCTCATTATTATTATTTTAAAGAAATGGCAGCAAGCCTACA

AAAGAAAAATAAGACAGAGCAGAGAAGAAAGAGTCATGGTATGCTTTTCTATCTTAGCAAAATT
```

-continued

```
AATCTCTACATGCCTAGGAAAAAGCCATGACAAGAGCAATCAGTTCAAAAGGTGTATGCAAAAA
ACCACATAATAGTAACTAGTACTGCATTGCCAGGAAGGAAGTTATGTCGCCATTCCATGGATCT
CATTCTCATTTCCTTGCAGCTTGAGAGTATAATCAACTTTGAAAAACTGACTGAATGGACCAGT
TCTAATGTTATGGAAGAGAGGAAGATCAAAGTGTACTTACCTCGCATGAAGATGGAGGAAAAAT
ACAACCTCACATCTGTCTTAATGGCTATGGGCATTACTGACGTGTTTAGCTCTTCAGCCAATCT
GTCTGGCATCTCCTCAGCAGAGAGCCTGAAGATATCTCAAGCTGTCCATGCAGCACATGCAGAA
ATCAATGAAGCAGGCAGAGAGGTGGTAGGGTCAGCAGAGGCTGGAGTGGATGCTGCAAGCGTCT
CTGAAGAATTTAGGGCTGACCATCCATTCCTCTTCTGTATCAAGCACATCGCAACCAACGCCGT
TCTCTTCTTTGGCAGATGTGTTTCCCCTGGAAGCGGAGCTACTAACTTCAGCCTGCTGAAGCAG
GCTGGAGACGTGGAGGAGAACCCTGGACCT[AntibodyHeavyChainCodingSequence]
GGAAGCGGAGCTACTAACTTCAGCCTGCTGAAGCAGGCTGGAGACGTGGAGGAGAACCCTGGAC
CT[AntibodyLightChainCodingSequence]TAAAAAGAAGAAAGCTGAAAAACTCTGT
CCCTTCCAACAAGACCCAGAGCACTGTAGTATCAGGGGTAAAATGAAAAGTATGTTCTCTGCTG
CATCCAGACTTCATAAAAGCTGGAGCTTAATCTAGAAAAAAAATCAGAAAGAAATTACACTGTG
AGAACAGGTGCAATTCACTTTTCCTTTACACAGAGTAATACTGGTAACTCATGGATGAAGGCTT
AAGGGAATGAAATTGGACTCACAGTACTGAGTCATCACACTGAAAAATGCAACCTGATACATCA
GCAGAAGGTTTATGGGGAAAAATGCAGCCTTCCAATTAAGCCAGATATCTGTATGACCAAGCT
CCTCCAGAATTAGTCACTCAAAATCTCTCAGATTAAATTATCAACTGTCACCAACTATTCCTAT
GCTGACAAGGCAATTGCTTGTTCTCTGTGTTCCTGATACTACAAGGCTCTTCCTGACTTCCTAA
AGATGCATTATAAAAATCTTATAATTCACATTTCTCCCTAAACTTTGACTCAATCATGGTATGT
TGGCAAATATGGTATATTACTATTCAAATTGTTTTCCTTGTACCCATATGTAATGGGTCTTGTG
AATGTGCTCTTTTGTTCCTTTAATCATAATAAAAACATGTTTAAGCAAACACTTTTCACTTGTA
GTATTTGAAGTACAGCAAGGTTGTGTAGCAGGGAAAGAATGACATGCAGAGGAATAAGTATGGA
CACACAGGCTAGCAGCGACTGTAGAACAAGTACTAATGGGTGAGAAGTTGAACAAGAGTCCCCT
ACAGCAACTTAATCTAATAAGCTAGTGGTCTACATCAGCTAAAAGAGCATAGTGAGGGATGAAA
TTGATTCTCCTTTCTAAGCATCACCTGGGACAACTCATCTGGAGCAGTGTGTCCAATCTGCCGC
TGCCCTGATCCTGGCTGGGGTGATGGGACAGACCTTGGCTGCCACTGAGACATCTGAGACACTG
AGATCTGTCTCAACTCAGATTTACCCAAGAACAGCTCATTGCCAACAGAACAAAATCTCAAACT
TATGGCTAGTGATGACAGCAGTCAGTTGTCCCATCTGTGACCCACCAAGGCTGGCATGCTGGAA
TGAGCAGGCTTTGGTGGCATGTAGTTACTGGACAGCACCACTGACATGGGCAGGGGAAAAACTG
AGCATGGTGTAAATCACTGCCTCAAAGCCACTTCTCTGTGCCTGCACCATGCTTGAAAGCTCTT
CTACAGGAGCTGGGTTTGTTCAAGAAAGCTTCTGTTTCTCCCATCTGCTTCTTGTACCTTCACA
GGGACAGAGTTAGAAGGGTACAGCCATGGTCGTGCCAGCTGCATTAATGAATCGGCCAACGCGC
GGGGAGAGGCGGTTTGCGTATTGGGCGCTCTTCCGCTTCCTCGCTCACTGACTCGCTGCGCTCG
GTCGTTCGGCTGCGGCGAGCGGTATCAGCTCACTCAAAGGCGGTAATACGGTTATCCACAGAAT
CAGGGGATAACGCAGGAAAGAACATGTGAGCAAAAGGCCAGCAAAAGGCCAGGAACCGTAAAAA
GGCCGCGTTGCTGGCGTTTTTCCATAGGCTCCGCCCCCCTGACGAGCATCACAAAAATCGATGC
TCAAGTCAGAGGTGGCGAAACCCGACAGGACTATAAAGATACCAGGCGTTTCCCCCTGGAAGCT
CCCTCGTGCGCTCTCCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGGTGTAGGTCGTTCGC
```

```
-continued
TCCAAGCTGGGCTGTGTGCACGAACCCCCCGTTCAGCCCGACCGCTGCGCCTTATCCGGTAACT
ATCGTCTTGAGTCCAACCCGGTAAGACACGACTTATCGCCACTGGCAGCAGCCACTGGTAACAG
GATTAGCAGAGCGAGGTATGTAGGCGGTGCTACAGAGTTCTTGAAGTGGTGGCCTAACTACGGC
TACACTAGAAGAACAGTATTTGGTATCTGCGCTCTGCTGAAGCCAGTTACCTTCGGAAAAAGAG
TTGGTAGCTCTTGATCCGGCAAACAAACCACCGCTGGTAGCGGTGGTTTTTTTGTTTGCAAGCA
GCAGATTACGCGCAGAAAAAAAGGATCTCAAGAAGATCCTTTGATCTTTTCTACGGGGTCTGAC
GCTCAGTGGAACGAAAACTCACGTTAAGGGATTTTGGTCATGAGATTATCAAAAAGGATCTTCA
CCTAGATCCTTTTAAATTAAAAATGAAGTTTTAAATCAATCTAAAGTATATATGAGTAAACTTG
GTCTGACAGTTACCAATGCTTAATCAGTGAGGCACCTATCTCAGCGATCTGTCTATTTCGTTCA
TCCATAGTTGCCTGACTCCCCGTCGTGTAGATAACTACGATACGGGAGGGCTTACCATCTGGCC
CCAGTGCTGCAATGATACCGCGAGACCCACGCTCACCGGCTCCAGATTTATCAGCAATAAACCA
GCCAGCCGGAAGGGCCGAGCGCAGAAGTGGTCCTGCAACTTTATCCGCCTCCATCCAGTCTATT
AATTGTTGCCGGGAAGCTAGAGTAAGTAGTTCGCCAGTTAATAGTTTGCGCAACGTTGTTGCCA
TTGCTACAGGCATCGTGGTGTCACGCTCGTCGTTTGGTATGGCTTCATTCAGCTCCGGTTCCCA
ACGATCAAGGCGAGTTACATGATCCCCCATGTTGTGCAAAAAAGCGGTTAGCTCCTTCGGTCCT
CCGATCGTTGTCAGAAGTAAGTTGGCCGCAGTGTTATCACTCATGGTTATGGCAGCACTGCATA
ATTCTCTTACTGTCATGCCATCCGTAAGATGCTTTTCTGTGACTGGTGAGTACTCAACCAAGTC
ATTCTGAGAATAGTGTATGCGGCGACCGAGTTGCTCTTGCCCGGCGTCAATACGGGATAATACC
GCGCCACATAGCAGAACTTTAAAAGTGCTCATCATTGGAAAACGTTCTTCGGGGCGAAAACTCT
CAAGGATCTTACCGCTGTTGAGATCCAGTTCGATGTAACCCACTCGTGCACCCAACTGATCTTC
AGCATCTTTTACTTTCACCAGCGTTTCTGGGTGAGCAAAAACAGGAAGGCAAAATGCCGCAAAA
AAGGGAATAAGGGCGACACGGAAATGTTGAATACTCATACTCTTCCTTTTTCAATATTATTGAA
GCATTTATCAGGGTTATTGTCTCATGAGCGGATACATATTTGAATGTATTTAGAAAAATAAACA
AATAGGGGTTCCGCGCACATTTCCCCGA
```

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of producing an exogenous protein in a bird egg, the method comprising:
    identifying a target genomic DNA sequence of a bird;
    identifying an insertion site in the target genomic DNA sequence and inserting a donor DNA sequence at the insertion site, wherein the donor DNA sequence encoding the exogenous protein and inserted in the insertion site is under transcriptional control of a regulatory element that directs liver-specific expression and secretion of the exogenous protein resulting in localization of the exogenous protein in an egg yolk of the bird;
    providing transfected avian primordial germ cells by introducing into the avian primordial germ cells: 1) a clustered, regularly interspaced, short palindromic repeats (CRISPR)-associated protein (Cas protein) or nucleic acid sequence encoding the Cas protein, 2) guide nucleotide sequence or nucleic acid sequence encoding the guide nucleotide sequence; and 3) the donor DNA sequence encoding the exogenous protein, thereby forming a complex of the Cas protein and guide nucleotide sequence in the avian primordial germ cells, wherein the complex specifically binds to, and cleaves, the target genomic DNA sequence producing the insertion site, whereby the donor DNA sequence is inserted into genomic DNA of the avian primordial germ cells in the insertion site;
    introducing the transfected avian primordial germ cells into a population of recipient bird embryos and incubating the recipient bird embryos, generating germline chimera birds;
    obtaining a heterozygote and/or homozygote transgenic bird by breeding the germline chimera bird; and
    isolating the exogenous protein from an egg laid by a female transgenic bird.

2. The method of claim 1, further comprising introducing a transfection marker into the avian germ cells and identifying transfected avian primordial germ cells by presence of the transfection marker.

3. The method of claim 2, wherein DNA encoding the transfection marker is not integrated into the genomic DNA of the avian primordial germ cells and is not present in the germline chimera birds or transgenic bird.

4. The method of claim 2, wherein the transfection marker is a puromycin resistance gene and identifying transfected avian primordial germ cells by presence of the transfection marker comprises incubating putatively transfected avian primordial germ cells with puromycin.

5. The method of claim 1, wherein the guide nucleotide sequence includes a cRNA and a trace RNA are combined in a single guide RNA molecule (gRNA).

6. The method of claim 1, wherein the donor DNA sequence comprises a first region homologous to the target sequence disposed 5' relative to the nucleotide sequence encoding the exogenous protein and second region homologous to the target sequence disposed 3' relative to the nucleotide sequence encoding the exogenous protein and the donor DNA sequence is inserted into the genome at the insertion site by homologous recombination.

7. The method of claim 6, wherein the donor DNA sequence comprises a first region homologous to the target sequence disposed upstream (5') relative to the nucleotide sequence encoding the exogenous protein and second region homologous to the target sequence disposed downstream (3') relative to the nucleotide sequence encoding the exogenous protein and the donor DNA sequence is inserted into the genuine at the insertion site by homologous recombination and wherein a selection gene encoding a selection marker is positioned upstream (5') relative to the first region or downstream (3') relative to the second region.

8. The method of claim 7, further comprising exposing the transfected avian primordial germ cells to a selection agent toxic to cells which do not express the selection marker, wherein the concentration of the selection agent and/or the amount of time of exposure of the cells to the selection agent produces a population of transfected PGCs wherein the donor DNA sequence encoding the exogenous protein and inserted in the insertion site is under transcriptional control of a regulatory element that directs tissue-specific expression of the exogenous protein resulting in localization of the exogenous protein in an egg of the bird and wherein the selection gene encoding a selection marker is not present in the genome of the transfected PGCs.

9. The method of claim 1, wherein the donor sequence is inserted into the genome at the insertion site by non-homologous end joining.

10. The method of claim 1, wherein introducing the transfected avian primordial germ cells into a population of recipient bird embryos comprises administration of the transfected avian primordial germ cells into a subgerminal cavity of the recipient bird embryos.

11. The method of claim 1, wherein introducing the transfected avian primordial germ cells into a population of recipient bird embryos comprises intravenous administration of the transfected avian primordial germ cells into the recipient bird embryos.

12. The method of claim 1, wherein the bird is a chicken and the avian primordial germ cells are chicken primordial germ cells.

13. The method of claim 1, wherein the bird is a quail and the avian primordial germ cells are quail primordial germ cells.

14. The method of claim 1, wherein the nucleic acid sequence encoding the Cas9 protein is a DNA or mRNA molecule.

15. The method of claim 1, wherein the guide nucleotide sequence includes a crRNA and a tracr RNA and the crRNA and tracr RNA are introduced into the avian primordial germ cells as two RNA molecules, a single RNA molecule (gRNA), two DNA molecules encoding, the crRNA and tracer RNA or a single DNA molecule encoding the gRNA.

16. The method of claim 1, wherein the regulatory element is a vitellogenin promoter.

17. The method of claim 1, wherein insertion of the donor DNA sequence at the insertion site destroys the target genomic DNA sequence, thereby avoiding re-cleavage by the complex of the Cas protein and guide nucleotide sequence and thereby enhancing knock-in success.

\* \* \* \* \*